(12) United States Patent
Edwards et al.

(10) Patent No.: US 9,522,235 B2
(45) Date of Patent: Dec. 20, 2016

(54) DEVICES AND METHODS FOR DELIVERING MEDICAMENTS FROM A MULTI-CHAMBER CONTAINER

(71) Applicant: kaleo, Inc., Richmond, VA (US)

(72) Inventors: Eric S. Edwards, Moseley, VA (US); Evan T. Edwards, Gordonsville, VA (US); Mark J. Licata, Doswell, VA (US); Paul F. Meyers, Fishers, IN (US); Frank E. Blondino, Henrico, VA (US)

(73) Assignee: kaleo, Inc., Richmond, VA (US)

( * ) Notice: Subject to any disclaimer, the term of this patent is extended or adjusted under 35 U.S.C. 154(b) by 514 days.

(21) Appl. No.: 13/827,582

(22) Filed: Mar. 14, 2013

(65) Prior Publication Data

US 2013/0317477 A1    Nov. 28, 2013

Related U.S. Application Data

(60) Provisional application No. 61/650,196, filed on May 22, 2012.

(51) Int. Cl.
*A61M 37/00* (2006.01)
*A61M 5/20* (2006.01)
(Continued)

(52) U.S. Cl.
CPC ............ *A61M 5/2066* (2013.01); *A61M 5/19* (2013.01); *A61M 5/2448* (2013.01); *A61M 2005/3132* (2013.01)

(58) Field of Classification Search
CPC ............ A61M 2005/31598; A61M 5/2066; A61M 5/2448; A61M 5/284; A61M 2005/3132
See application file for complete search history.

(56) References Cited

U.S. PATENT DOCUMENTS 2,960,087 A    11/1960 Uytenbogaart
3,055,362 A    9/1962 Uytenbogaart
(Continued)

FOREIGN PATENT DOCUMENTS

DE    20 2009 003 009    7/2009
EP    1287840 A1    3/2003
(Continued)

OTHER PUBLICATIONS

Office Action for Chinese Patent Application No. 201280015406.6, mailed Dec. 2, 2014.
(Continued)

*Primary Examiner* — Emily Schmidt

(57) ABSTRACT

An apparatus includes a medicament container, a first elastomeric member, a second elastomeric member and a stopper. The first and second elastomeric members are disposed within the medicament container. The first elastomeric member, a first portion of the medicament container and the second elastomeric member collectively define a medicament volume. The stopper is coupled to a distal end portion of the medicament container. The second elastomeric member, a second portion of the medicament container and the stopper collectively define a vent volume. A first retainer of the stopper is configured to engage a first portion of a carrier to limit movement of the medicament container when in a first position. A second retainer of the stopper is configured to engage a second portion of the carrier to limit movement of the medicament container when in a second position.

16 Claims, 36 Drawing Sheets

(51) Int. Cl.
*A61M 5/19* (2006.01)
*A61M 5/24* (2006.01)
*A61M 5/31* (2006.01)

(56) References Cited

U.S. PATENT DOCUMENTS

| | | | |
|---|---|---|---|
| 3,115,133 A | 12/1963 | Morando | |
| 3,426,448 A | 2/1969 | Sarnoff | |
| 3,563,373 A * | 2/1971 | Paulson | A61J 1/2093 |
| | | | 206/229 |
| 3,688,765 A | 9/1972 | Gasaway | |
| 3,768,472 A | 10/1973 | Hodosh et al. | |
| 3,795,061 A | 3/1974 | Sarnoff et al. | |
| 3,945,379 A | 3/1976 | Pritz et al. | |
| 4,108,177 A | 8/1978 | Pistor | |
| 4,124,024 A | 11/1978 | Schwebel et al. | |
| 4,226,235 A | 10/1980 | Sarnoff et al. | |
| 4,258,713 A | 3/1981 | Wardlaw | |
| 4,360,019 A | 11/1982 | Portner et al. | |
| 4,394,863 A | 7/1983 | Bartner | |
| 4,424,057 A | 1/1984 | House | |
| 4,441,629 A | 4/1984 | Mackal | |
| 4,484,910 A | 11/1984 | Sarnoff | |
| 4,573,976 A | 3/1986 | Sampson et al. | |
| 4,596,556 A | 6/1986 | Morrow et al. | |
| 4,610,666 A | 9/1986 | Pizzino | |
| 4,617,557 A | 10/1986 | Gordon | |
| 4,624,660 A | 11/1986 | Mijers et al. | |
| 4,640,686 A | 2/1987 | Dalling et al. | |
| 4,643,721 A | 2/1987 | Brunet | |
| 4,666,430 A | 5/1987 | Brown et al. | |
| 4,673,657 A | 6/1987 | Christian | |
| 4,689,042 A | 8/1987 | Sarnoff et al. | |
| 4,693,708 A | 9/1987 | Wanderer et al. | |
| 4,755,169 A | 7/1988 | Sarnoff et al. | |
| 4,781,697 A | 11/1988 | Slaughter | |
| 4,782,841 A | 11/1988 | Lopez | |
| 4,784,652 A | 11/1988 | Wikström | |
| 4,795,433 A | 1/1989 | Sarnoff | |
| 4,820,286 A | 4/1989 | van der Wal | |
| 4,822,340 A * | 4/1989 | Kamstra | A61M 5/2066 |
| | | | 604/135 |
| 4,826,489 A * | 5/1989 | Haber | A61M 5/24 |
| | | | 604/195 |
| 4,853,521 A | 8/1989 | Claeys et al. | |
| 4,874,381 A | 10/1989 | Vetter | |
| 4,874,382 A | 10/1989 | Lindemann et al. | |
| 4,894,054 A | 1/1990 | Miskinyar | |
| 4,906,235 A | 3/1990 | Roberts | |
| 4,915,695 A | 4/1990 | Koobs | |
| 4,941,880 A | 7/1990 | Burns | |
| 4,959,056 A | 9/1990 | Dombrowski et al. | |
| 4,968,302 A | 11/1990 | Schluter et al. | |
| 4,983,164 A | 1/1991 | Hook et al. | |
| 5,000,736 A | 3/1991 | Kaufhold, Jr. et al. | |
| 5,024,656 A | 6/1991 | Gasaway et al. | |
| 5,037,306 A | 8/1991 | van Schoonhoven | |
| 5,038,023 A | 8/1991 | Saliga | |
| 5,041,088 A | 8/1991 | Ritson et al. | |
| 5,042,977 A | 8/1991 | Bechtold et al. | |
| 5,062,603 A | 11/1991 | Smith et al. | |
| 5,064,413 A | 11/1991 | McKinnon et al. | |
| 5,071,353 A | 12/1991 | van der Wal | |
| 5,080,649 A | 1/1992 | Vetter | |
| 5,085,642 A | 2/1992 | Sarnoff et al. | |
| 5,092,843 A | 3/1992 | Monroe et al. | |
| 5,104,380 A | 4/1992 | Holman et al. | |
| 5,125,898 A | 6/1992 | Kaufhold, Jr. et al. | |
| 5,139,490 A | 8/1992 | Vetter et al. | |
| 5,167,641 A | 12/1992 | Schmitz | |
| 5,199,949 A | 4/1993 | Haber et al. | |
| 5,224,936 A | 7/1993 | Gallagher | |
| 5,240,146 A | 8/1993 | Smedley et al. | |
| 5,244,465 A | 9/1993 | Michel | |
| 5,271,527 A | 12/1993 | Haber et al. | |
| 5,281,198 A | 1/1994 | Haber et al. |
| 5,286,258 A | 2/1994 | Haber et al. |
| 5,298,023 A | 3/1994 | Haber et al. |
| 5,298,024 A | 3/1994 | Richmond |
| 5,312,326 A | 5/1994 | Myers et al. |
| 5,314,412 A | 5/1994 | Rex |
| 5,320,603 A | 6/1994 | Vetter et al. |
| 5,343,519 A | 8/1994 | Feldman |
| 5,344,407 A | 9/1994 | Ryan |
| 5,354,284 A | 10/1994 | Haber et al. |
| 5,356,376 A | 10/1994 | Milijasevic et al. |
| 5,363,842 A | 11/1994 | Mishelevich et al. |
| 5,380,281 A | 1/1995 | Tomellini et al. |
| 5,383,851 A | 1/1995 | McKinnon, Jr. et al. |
| 5,383,864 A | 1/1995 | van den Heuvel |
| 5,394,866 A | 3/1995 | Ritson et al. |
| 5,399,163 A | 3/1995 | Peterson et al. |
| 5,417,660 A | 5/1995 | Martin |
| 5,466,217 A | 11/1995 | Myers et al. |
| 5,514,097 A | 5/1996 | Knauer |
| 5,514,135 A | 5/1996 | Earle |
| 5,558,679 A | 9/1996 | Tuttle |
| 5,567,160 A | 10/1996 | Massino |
| 5,568,555 A | 10/1996 | Shamir |
| 5,569,192 A | 10/1996 | van der Wal |
| 5,584,815 A | 12/1996 | Pawelka et al. |
| 5,615,771 A | 4/1997 | Hollister |
| 5,616,132 A | 4/1997 | Newman |
| 5,645,534 A | 7/1997 | Chanoch |
| 5,662,612 A | 9/1997 | Niehoff |
| 5,681,291 A | 10/1997 | Galli |
| 5,692,492 A | 12/1997 | Bruna et al. |
| 5,695,476 A | 12/1997 | Harris |
| 5,697,916 A | 12/1997 | Schraga |
| 5,716,338 A | 2/1998 | Hjertman et al. |
| 5,728,074 A | 3/1998 | Castellano et al. |
| 5,743,886 A | 4/1998 | Lynn et al. |
| 5,772,635 A | 6/1998 | Dastur et al. |
| 5,792,190 A | 8/1998 | Olson et al. |
| 5,800,397 A | 9/1998 | Wilson et al. |
| 5,805,423 A | 9/1998 | Wever et al. |
| 5,809,997 A | 9/1998 | Wolf |
| 5,813,397 A | 9/1998 | Goodman et al. |
| 5,814,020 A | 9/1998 | Gross |
| 5,823,346 A | 10/1998 | Weiner |
| 5,832,488 A | 11/1998 | Eberhardt |
| 5,837,546 A | 11/1998 | Allen et al. |
| RE35,986 E | 12/1998 | Ritson et al. |
| 5,846,089 A | 12/1998 | Weiss et al. |
| 5,848,988 A | 12/1998 | Davis |
| 5,852,590 A | 12/1998 | de la Huerga |
| 5,853,292 A | 12/1998 | Eggert et al. |
| 5,858,001 A | 1/1999 | Tsals et al. |
| 5,865,795 A | 2/1999 | Schiff et al. |
| 5,868,713 A | 2/1999 | Klippenstein |
| 5,868,721 A | 2/1999 | Marinacci |
| D407,487 S | 3/1999 | Greubel et al. |
| 5,925,021 A | 7/1999 | Castellano et al. |
| 5,928,195 A | 7/1999 | Malamud |
| 5,941,857 A | 8/1999 | Nguyen et al. |
| 5,964,739 A | 10/1999 | Champ |
| 5,970,457 A | 10/1999 | Brant et al. |
| 5,971,953 A | 10/1999 | Bachynsky |
| 6,015,438 A | 1/2000 | Shaw |
| 6,030,363 A | 2/2000 | Kriesel |
| 6,039,713 A | 3/2000 | Botich et al. |
| 6,045,534 A | 4/2000 | Jacobsen et al. |
| 6,056,728 A | 5/2000 | von Schuckmann |
| 6,062,901 A | 5/2000 | Liu et al. |
| 6,063,053 A | 5/2000 | Castellano et al. |
| 6,074,213 A | 6/2000 | Hon |
| 6,077,106 A | 6/2000 | Mish |
| 6,083,199 A | 7/2000 | Thorley et al. |
| 6,084,526 A | 7/2000 | Blotky et al. |
| 6,086,562 A | 7/2000 | Jacobsen et al. |
| 6,096,002 A | 8/2000 | Landau |
| 6,099,504 A | 8/2000 | Gross et al. |
| 6,102,896 A | 8/2000 | Roser |
| 6,119,684 A | 9/2000 | Nöhl et al. |

(56) References Cited

U.S. PATENT DOCUMENTS

| | | |
|---|---|---|
| 6,149,626 A | 11/2000 | Rachynsky et al. |
| 6,158,613 A | 12/2000 | Novosel et al. |
| 6,161,281 A | 12/2000 | Dando et al. |
| 6,165,155 A | 12/2000 | Jacobsen et al. |
| 6,179,812 B1 | 1/2001 | Botich et al. |
| 6,192,891 B1 | 2/2001 | Gravel et al. |
| 6,193,695 B1 | 2/2001 | Rippstein, Jr. |
| 6,202,642 B1 | 3/2001 | McKinnon et al. |
| 6,210,359 B1 | 4/2001 | Patel et al. |
| 6,210,369 B1 | 4/2001 | Wilmot et al. |
| 6,219,587 B1 | 4/2001 | Ahlin et al. |
| 6,221,045 B1 | 4/2001 | Duchon et al. |
| 6,221,055 B1 | 4/2001 | Shaw et al. |
| 6,245,046 B1 | 6/2001 | Sibbitt |
| 6,258,063 B1 | 7/2001 | Haar et al. |
| 6,259,654 B1 | 7/2001 | de la Huerga |
| 6,264,629 B1 | 7/2001 | Landau |
| 6,312,412 B1 | 11/2001 | Saied et al. |
| 6,317,630 B1 | 11/2001 | Gross et al. |
| 6,334,070 B1 | 12/2001 | Nova et al. |
| 6,364,866 B1 | 4/2002 | Furr et al. |
| 6,371,939 B2 | 4/2002 | Bergens et al. |
| 6,387,078 B1 | 5/2002 | Gillespie, III |
| 6,405,912 B2 | 6/2002 | Giannou |
| 6,406,455 B1 | 6/2002 | Willis et al. |
| 6,411,567 B1 | 6/2002 | Niemiec et al. |
| 6,413,236 B1 | 7/2002 | Van Dyke |
| 6,419,656 B1 | 7/2002 | Vetter et al. |
| 6,425,897 B2 | 7/2002 | Overes et al. |
| 6,428,517 B1 | 8/2002 | Hochman et al. |
| 6,428,528 B2 | 8/2002 | Sadowski |
| 6,454,746 B1 | 9/2002 | Bydlon et al. |
| 6,475,181 B1 | 11/2002 | Potter et al. |
| 6,478,769 B1 | 11/2002 | Parker |
| 6,478,771 B1 | 11/2002 | Lavi et al. |
| 6,482,185 B1 | 11/2002 | Hartmann |
| 6,482,186 B1 | 11/2002 | Douglas et al. |
| 6,494,863 B1 | 12/2002 | Shaw et al. |
| 6,500,150 B1 | 12/2002 | Gross et al. |
| 6,514,230 B1 | 2/2003 | Munk et al. |
| 6,529,446 B1 | 3/2003 | de la Huerga |
| 6,530,900 B1 | 3/2003 | Dailey et al. |
| 6,530,904 B1 | 3/2003 | Edwards et al. |
| 6,535,714 B2 | 3/2003 | Melker et al. |
| 6,540,672 B1 | 4/2003 | Simonsen et al. |
| 6,540,675 B2 | 4/2003 | Aceti et al. |
| 6,544,233 B1 | 4/2003 | Fukui et al. |
| 6,544,234 B1 | 4/2003 | Gabriel |
| 6,551,276 B1 | 4/2003 | Mann et al. |
| 6,551,298 B1 | 4/2003 | Zhang |
| 6,554,798 B1 | 4/2003 | Mann et al. |
| 6,558,320 B1 | 5/2003 | Causey, III et al. |
| 6,560,471 B1 | 5/2003 | Heller |
| 6,565,533 B1 | 5/2003 | Smith et al. |
| 6,569,123 B2 | 5/2003 | Alchas |
| 6,572,584 B1 | 6/2003 | Shaw et al. |
| 6,574,166 B2 | 6/2003 | Niemiec |
| 6,575,939 B1 | 6/2003 | Brunel |
| RE38,189 E | 7/2003 | Walker et al. |
| 6,585,685 B2 | 7/2003 | Staylor et al. |
| 6,585,698 B1 | 7/2003 | Packman et al. |
| 6,589,158 B2 | 7/2003 | Winkler |
| 6,595,956 B1 | 7/2003 | Gross et al. |
| 6,599,272 B1 | 7/2003 | Hjertman et al. |
| 6,616,627 B2 | 9/2003 | Willis et al. |
| 6,633,796 B1 | 10/2003 | Pool et al. |
| 6,641,566 B2 | 11/2003 | Douglas et al. |
| 6,645,171 B1 | 11/2003 | Robinson et al. |
| 6,645,181 B1 | 11/2003 | Lavi et al. |
| 6,648,850 B2 | 11/2003 | Landau |
| 6,656,150 B2 | 12/2003 | Hill et al. |
| 6,659,980 B2 | 12/2003 | Moberg et al. |
| 6,676,630 B2 | 1/2004 | Landau et al. |
| 6,679,862 B2 | 1/2004 | Diaz et al. |
| 6,689,093 B2 | 2/2004 | Landau |
| 6,702,778 B2 | 3/2004 | Hill et al. |
| 6,707,763 B2 | 3/2004 | Osberg et al. |
| 6,708,050 B2 | 3/2004 | Carim |
| 6,722,916 B2 | 4/2004 | Buccinna et al. |
| 6,723,077 B2 | 4/2004 | Pickup et al. |
| 6,726,661 B2 | 4/2004 | Munk et al. |
| 6,736,796 B2 | 5/2004 | Shekalim |
| 6,743,635 B2 | 6/2004 | Neel et al. |
| 6,749,437 B2 | 6/2004 | Chan |
| 6,752,781 B2 | 6/2004 | Landau et al. |
| 6,764,469 B2 | 7/2004 | Broselow |
| 6,767,336 B1 | 7/2004 | Kaplan |
| 6,770,052 B2 | 8/2004 | Hill et al. |
| 6,770,056 B2 | 8/2004 | Price et al. |
| 6,783,509 B1 | 8/2004 | Landau et al. |
| 6,786,875 B2 | 9/2004 | Barker et al. |
| 6,786,885 B2 | 9/2004 | Hochman et al. |
| 6,793,646 B1 | 9/2004 | Giambattista et al. |
| 6,803,856 B1 | 10/2004 | Murphy et al. |
| 6,808,514 B2 | 10/2004 | Schneider et al. |
| 6,809,653 B1 | 10/2004 | Mann et al. |
| 6,817,986 B2 | 11/2004 | Slate et al. |
| 6,817,987 B2 | 11/2004 | Vetter et al. |
| 6,830,560 B1 | 12/2004 | Gross et al. |
| 6,839,304 B2 | 1/2005 | Niemiec et al. |
| 6,872,200 B2 | 3/2005 | Mann et al. |
| 6,875,195 B2 | 4/2005 | Choi |
| 6,883,222 B2 | 4/2005 | Landau |
| 6,893,420 B2 | 5/2005 | Arnisolle |
| 6,923,764 B2 | 8/2005 | Aceti et al. |
| 6,936,029 B2 | 8/2005 | Mann et al. |
| 6,936,032 B1 | 8/2005 | Bush, Jr. et al. |
| 6,937,150 B2 | 8/2005 | Medema et al. |
| 6,942,646 B2 | 9/2005 | Langley et al. |
| 6,946,299 B2 | 9/2005 | Neel et al. |
| 6,949,082 B2 | 9/2005 | Langley et al. |
| 6,952,604 B2 | 10/2005 | DeNuzzio et al. |
| 6,953,445 B2 | 10/2005 | Wilmot et al. |
| 6,953,693 B2 | 10/2005 | Neel et al. |
| 6,958,691 B1 | 10/2005 | Anderson et al. |
| 6,959,247 B2 | 10/2005 | Neel et al. |
| 6,961,285 B2 | 11/2005 | Niemiec et al. |
| 6,964,650 B2 | 11/2005 | Alexandre et al. |
| 6,969,259 B2 | 11/2005 | Pastrick et al. |
| 6,979,316 B1 | 12/2005 | Rubin et al. |
| 6,979,326 B2 | 12/2005 | Mann et al. |
| 6,985,870 B2 | 1/2006 | Martucci et al. |
| 6,997,911 B2 | 2/2006 | Klitmose |
| 7,014,470 B2 | 3/2006 | Vann |
| 7,077,835 B2 | 7/2006 | Robinson et al. |
| 7,104,972 B2 | 9/2006 | Moller et al. |
| 7,113,101 B2 | 9/2006 | Peterson et al. |
| 7,116,233 B2 | 10/2006 | Zhurin |
| 7,118,553 B2 | 10/2006 | Scherer |
| 7,126,879 B2 | 10/2006 | Snyder |
| 7,158,011 B2 | 1/2007 | Brue |
| 7,191,916 B2 | 3/2007 | Clifford et al. |
| 7,278,983 B2 | 10/2007 | Ireland et al. |
| 7,299,981 B2 | 11/2007 | Hickle et al. |
| 7,351,223 B2 | 4/2008 | Call |
| 7,416,540 B2 | 8/2008 | Edwards et al. |
| 7,500,963 B2 | 3/2009 | Westbye et al. |
| 7,500,967 B2 | 3/2009 | Thorley et al. |
| 7,503,907 B1 | 3/2009 | Lesch, Jr. |
| 7,544,188 B2 | 6/2009 | Edwards et al. |
| 7,648,482 B2 | 1/2010 | Edwards et al. |
| 7,648,483 B2 | 1/2010 | Edwards et al. |
| 7,678,073 B2 | 3/2010 | Griffiths et al. |
| 7,708,719 B2 | 5/2010 | Wilmot et al. |
| 7,731,686 B2 | 6/2010 | Edwards et al. |
| 7,749,194 B2 | 7/2010 | Edwards et al. |
| 7,758,550 B2 | 7/2010 | Bollenbach et al. |
| 7,806,866 B2 | 10/2010 | Hommann et al. |
| 7,850,662 B2 | 12/2010 | Veasey et al. |
| 7,871,393 B2 | 1/2011 | Monroe |
| 7,918,823 B2 | 4/2011 | Edwards et al. |
| 7,918,832 B2 | 4/2011 | Veasey et al. |
| 7,938,802 B2 | 5/2011 | Bicknell et al. |
| 7,947,017 B2 | 5/2011 | Edwards et al. |

(56) References Cited

U.S. PATENT DOCUMENTS

| | | |
|---|---|---|
| 8,016,788 B2 | 9/2011 | Edwards et al. |
| 8,021,335 B2 | 9/2011 | Lesch, Jr. |
| 8,105,281 B2 | 1/2012 | Edwards et al. |
| 8,123,719 B2 | 2/2012 | Edwards et al. |
| 8,162,886 B2 | 4/2012 | Sadowski et al. |
| 8,172,082 B2 | 5/2012 | Edwards et al. |
| 8,177,749 B2 | 5/2012 | Slate et al. |
| 8,206,360 B2 | 6/2012 | Edwards et al. |
| 8,231,573 B2 | 7/2012 | Edwards et al. |
| 8,251,947 B2 | 8/2012 | Kramer et al. |
| 8,276,583 B2 | 10/2012 | Farieta et al. |
| 8,313,466 B2 | 11/2012 | Edwards et al. |
| 8,361,029 B2 | 1/2013 | Edwards et al. |
| 8,361,035 B2 | 1/2013 | Thorley et al. |
| 8,425,462 B2 | 4/2013 | Edwards et al. |
| 8,574,214 B2 | 11/2013 | Kühn et al. |
| 8,608,698 B2 | 12/2013 | Edwards et al. |
| 8,613,720 B2 | 12/2013 | Bendek et al. |
| 8,627,816 B2 | 1/2014 | Edwards et al. |
| 8,708,968 B2 | 4/2014 | Julian et al. |
| 8,734,394 B2 | 5/2014 | Adams et al. |
| 8,920,377 B2 | 12/2014 | Edwards et al. |
| 8,939,943 B2 | 1/2015 | Edwards et al. |
| 8,961,455 B2 | 2/2015 | Holmqvist et al. |
| 9,056,170 B2 | 6/2015 | Edwards et al. |
| 2002/0016567 A1 | 2/2002 | Hochman et al. |
| 2002/0042596 A1 | 4/2002 | Hartlaub et al. |
| 2002/0074345 A1 | 6/2002 | Schneider et al. |
| 2002/0076679 A1 | 6/2002 | Aman |
| 2002/0090601 A1 | 7/2002 | Strupat et al. |
| 2002/0096543 A1 | 7/2002 | Juselius |
| 2003/0028145 A1 | 2/2003 | Duchon et al. |
| 2003/0040717 A1 | 2/2003 | Saulenas et al. |
| 2003/0105430 A1 | 6/2003 | Lavi et al. |
| 2003/0106824 A1 | 6/2003 | Wilmot et al. |
| 2003/0120222 A1 | 6/2003 | Vaillancourt |
| 2003/0135388 A1 | 7/2003 | Martucci et al. |
| 2004/0015125 A1 | 1/2004 | Alexandre et al. |
| 2004/0019326 A1 | 1/2004 | Gilbert et al. |
| 2004/0024361 A1 | 2/2004 | Fago et al. |
| 2004/0039336 A1 | 2/2004 | Amark et al. |
| 2004/0039337 A1 | 2/2004 | Letzing |
| 2004/0039368 A1 | 2/2004 | Reilly et al. |
| 2004/0054327 A1 | 3/2004 | Gillespie, III |
| 2004/0092874 A1 | 5/2004 | Mazidji |
| 2004/0116854 A1 | 6/2004 | Abulhaj et al. |
| 2004/0138611 A1 | 7/2004 | Griffiths et al. |
| 2004/0143298 A1 | 7/2004 | Nova et al. |
| 2004/0159364 A1 | 8/2004 | Landau et al. |
| 2004/0210199 A1 | 10/2004 | Atterbury et al. |
| 2004/0220524 A1 | 11/2004 | Sadowski et al. |
| 2004/0249358 A1 | 12/2004 | McWethy et al. |
| 2004/0267204 A1 | 12/2004 | Brustowicz |
| 2005/0027255 A1 | 2/2005 | Lavi et al. |
| 2005/0033234 A1 | 2/2005 | Sadowski et al. |
| 2005/0033386 A1 | 2/2005 | Osborn et al. |
| 2005/0062603 A1 | 3/2005 | Fuerst et al. |
| 2005/0090781 A1 | 4/2005 | Baba et al. |
| 2005/0090782 A1 | 4/2005 | Marshall et al. |
| 2005/0096588 A1 | 5/2005 | Hagmann et al. |
| 2005/0101912 A1 | 5/2005 | Faust et al. |
| 2005/0134433 A1 | 6/2005 | Sweeney, II |
| 2005/0148931 A1 | 7/2005 | Juhasz |
| 2005/0148945 A1 | 7/2005 | Chen |
| 2005/0159705 A1 | 7/2005 | Crawford et al. |
| 2005/0165360 A1 | 7/2005 | Stamp |
| 2005/0168337 A1 | 8/2005 | Mahoney |
| 2005/0171477 A1 | 8/2005 | Rubin et al. |
| 2005/0182358 A1 | 8/2005 | Veit et al. |
| 2005/0183982 A1 | 8/2005 | Giewercer |
| 2005/0186221 A1 | 8/2005 | Reynolds et al. |
| 2005/0192530 A1 | 9/2005 | Castellano |
| 2005/0197654 A1 | 9/2005 | Edman et al. |
| 2005/0203466 A1 | 9/2005 | Hommann et al. |
| 2005/0261742 A1 | 11/2005 | Nova et al. |
| 2005/0267403 A1 | 12/2005 | Landau et al. |
| 2005/0277891 A1 | 12/2005 | Sibbitt |
| 2006/0030819 A1 | 2/2006 | Young et al. |
| 2006/0053036 A1 | 3/2006 | Coffman et al. |
| 2006/0058848 A1 | 3/2006 | Piraino et al. |
| 2006/0069350 A1 | 3/2006 | Buenger et al. |
| 2006/0111666 A1 | 5/2006 | Hommann et al. |
| 2006/0111671 A1 | 5/2006 | Klippenstein |
| 2006/0116639 A1 | 6/2006 | Russell |
| 2006/0129089 A1 | 6/2006 | Stamp |
| 2006/0129090 A1 | 6/2006 | Moberg et al. |
| 2006/0189938 A1 | 8/2006 | Hommann et al. |
| 2006/0200077 A1 | 9/2006 | Righi et al. |
| 2006/0235354 A1 | 10/2006 | Kaal et al. |
| 2006/0247578 A1 | 11/2006 | Arguedas et al. |
| 2006/0247579 A1 | 11/2006 | Friedman |
| 2006/0265186 A1 | 11/2006 | Holland et al. |
| 2007/0008113 A1 | 1/2007 | Spoonhower et al. |
| 2007/0074722 A1 | 4/2007 | Giroux et al. |
| 2007/0100288 A1 | 5/2007 | Bozeman et al. |
| 2007/0129686 A1 | 6/2007 | Daily et al. |
| 2007/0173772 A1 | 7/2007 | Liversidge |
| 2007/0184847 A1 | 8/2007 | Hansen et al. |
| 2007/0203247 A1 | 8/2007 | Phillips et al. |
| 2007/0210147 A1 | 9/2007 | Morrone et al. |
| 2007/0213598 A1 | 9/2007 | Howard et al. |
| 2007/0233001 A1 | 10/2007 | Burroughs et al. |
| 2008/0059133 A1 | 3/2008 | Edwards et al. |
| 2008/0111685 A1 | 5/2008 | Olson et al. |
| 2008/0160492 A1 | 7/2008 | Campbell et al. |
| 2008/0171995 A1 | 7/2008 | Vitullo et al. |
| 2008/0188798 A1 | 8/2008 | Weber |
| 2008/0249468 A1 | 10/2008 | Edwards et al. |
| 2008/0255513 A1 | 10/2008 | Kaal et al. |
| 2009/0005735 A1 | 1/2009 | Wikner et al. |
| 2009/0093759 A1 | 4/2009 | Judd et al. |
| 2009/0221962 A1 | 9/2009 | Kaal et al. |
| 2009/0240200 A1 | 9/2009 | Heneveld et al. |
| 2010/0107783 A1 | 5/2010 | Maeda |
| 2010/0160894 A1 | 6/2010 | Julian et al. |
| 2010/0318035 A1 | 12/2010 | Edwards et al. |
| 2011/0060274 A1 | 3/2011 | Kuhn |
| 2011/0201999 A1* | 8/2011 | Cronenberg ........ A61M 5/2066 604/89 |
| 2012/0016296 A1 | 1/2012 | Charles |
| 2012/0046613 A1 | 2/2012 | Plumptre |
| 2012/0079718 A1 | 4/2012 | Singer et al. |
| 2012/0116318 A1 | 5/2012 | Edwards et al. |
| 2012/0125951 A1 | 5/2012 | Leak et al. |
| 2012/0136298 A1 | 5/2012 | Bendix et al. |
| 2012/0136316 A1 | 5/2012 | Davies et al. |
| 2012/0172804 A1 | 7/2012 | Plumptre |
| 2012/0172817 A1 | 7/2012 | Bruggemann et al. |
| 2012/0191049 A1 | 7/2012 | Harms et al. |
| 2012/0191066 A1 | 7/2012 | Schabbach et al. |
| 2012/0197210 A1 | 8/2012 | Kuhn et al. |
| 2012/0209200 A1 | 8/2012 | Jones et al. |
| 2012/0220949 A1 | 8/2012 | Davies et al. |
| 2012/0226238 A1 | 9/2012 | Davies et al. |
| 2012/0238960 A1 | 9/2012 | Smith et al. |
| 2012/0253288 A1 | 10/2012 | Dasbach et al. |
| 2012/0259285 A1 | 10/2012 | Schabbach et al. |
| 2012/0271243 A1 | 10/2012 | Plumptre |
| 2012/0283648 A1 | 11/2012 | Veasey et al. |
| 2012/0283651 A1 | 11/2012 | Veasey et al. |
| 2012/0283662 A1 | 11/2012 | MacDonald et al. |
| 2012/0289906 A1 | 11/2012 | Jones et al. |
| 2012/0289929 A1 | 11/2012 | Boyd et al. |
| 2012/0310168 A1 | 12/2012 | Plumptre et al. |
| 2012/0310206 A1 | 12/2012 | Kouyoumjian et al. |
| 2012/0325865 A1 | 12/2012 | Forstreuter et al. |
| 2012/0330244 A1 | 12/2012 | Helmer et al. |
| 2013/0023822 A1 | 1/2013 | Edwards et al. |
| 2013/0023825 A1 | 1/2013 | Edwards et al. |
| 2013/0035664 A1 | 2/2013 | Mojdehbakhsh et al. |
| 2013/0060231 A1 | 3/2013 | Adlon et al. |
| 2013/0060232 A1 | 3/2013 | Adlon et al. |
| 2013/0090604 A1 | 4/2013 | Davies et al. |
| 2013/0102973 A1 | 4/2013 | Thorley et al. |

(56) References Cited

U.S. PATENT DOCUMENTS

| | | |
|---|---|---|
| 2013/0110050 A1 | 5/2013 | Boyd et al. |
| 2013/0178823 A1 | 7/2013 | Buchine et al. |
| 2013/0226084 A1 | 8/2013 | Samandi et al. |
| 2013/0226134 A1 | 8/2013 | Schabbach et al. |
| 2013/0237924 A1 | 9/2013 | Leak et al. |
| 2013/0237932 A1 | 9/2013 | Thueer et al. |
| 2013/0245562 A1 | 9/2013 | Kouyoumjian et al. |
| 2013/0266919 A1 | 10/2013 | Baker et al. |
| 2013/0274707 A1 | 10/2013 | Wilmot et al. |
| 2014/0031789 A1 | 1/2014 | Edwards et al. |
| 2014/0081234 A1 | 3/2014 | Eggert et al. |
| 2014/0114258 A1 | 4/2014 | Day |
| 2014/0188075 A1 | 7/2014 | Eggert et al. |
| 2014/0276414 A1 | 9/2014 | Baker et al. |
| 2014/0336586 A1 | 11/2014 | Bengtsson et al. |
| 2014/0336610 A1 | 11/2014 | Michel et al. |
| 2015/0174323 A1 | 6/2015 | Edwards et al. |

FOREIGN PATENT DOCUMENTS

| | | |
|---|---|---|
| EP | 1462134 A1 | 9/2004 |
| EP | 1518575 A1 | 3/2005 |
| EP | 1712178 A2 | 10/2006 |
| EP | 1095668 B1 | 4/2007 |
| FR | 2506161 | 11/1982 |
| FR | 2 509 615 | 1/1983 |
| JP | 51-021295 | 2/1976 |
| JP | 55-75335 | 8/2014 |
| MX | PA04009276 | 1/2005 |
| WO | WO 86/06967 | 12/1986 |
| WO | WO 91/04760 A1 | 4/1991 |
| WO | WO 92/18176 | 10/1992 |
| WO | WO93/02720 | 2/1993 |
| WO | WO 94/06487 | 3/1994 |
| WO | WO 95/26009 | 9/1995 |
| WO | WO 95/35126 | 12/1995 |
| WO | WO 98/52632 | 11/1998 |
| WO | WO 99/10031 | 3/1999 |
| WO | WO 01/24690 A2 | 4/2001 |
| WO | WO 01/26020 A1 | 4/2001 |
| WO | WO 01/41849 A2 | 6/2001 |
| WO | WO 01/88828 | 11/2001 |
| WO | WO 01/93926 A2 | 12/2001 |
| WO | WO 03/095001 A1 | 11/2003 |
| WO | WO 03/097133 A1 | 11/2003 |
| WO | WO 2004/054644 | 7/2004 |
| WO | WO 2005/050526 A2 | 6/2005 |
| WO | WO 2005/077441 | 8/2005 |
| WO | WO 2006/045525 A1 | 5/2006 |
| WO | WO 2006/109778 A1 | 10/2006 |
| WO | WO 2006/125692 | 11/2006 |
| WO | WO 2007/075839 A2 | 7/2007 |
| WO | WO 2008/005315 | 1/2008 |
| WO | WO 2008/082704 A2 | 7/2008 |
| WO | WO 2008/148864 | 12/2008 |
| WO | WO 2010/033806 | 3/2010 |
| WO | WO2013/044172 | 3/2013 |
| WO | WO 2013/086292 A1 | 6/2013 |
| WO | WO 2013/119591 A1 | 8/2013 |
| WO | WO 2014/085118 A1 | 6/2014 |

OTHER PUBLICATIONS

Supplementary Search Report for European Patent Application No. 12739882.4, mailed Aug. 5, 2014, 7 pages.
"Solutions for Medical Devices," 3M Brochure, © 3M 2006 80-6201-3490-0.
Merle Tingelstad, "Revolutionary Medical Technology Increases Demand for Flexible Interconnects," [online] May 15, 2006 [retrieved on Nov. 15, 2006] Retrieved from the Internet <URL: http://www.ecnmag.com/index.asp?layout=artielePrint&ArticleID=CA6332947 >.
"Flexible circuits / Flex circuits / Flexible Technology Ltd.," Flexible Technology Limited [online] [retrieved on Aug. 28, 2006] Retrieved from the Internet <URL: http://www.flexibletechnology.com/>.
"Flexible circuits capabilities of Flexible Technology Limited," Our Flexible Circuits Capabilities [online] [retrieved on Aug. 28, 2006] Retrieved from the Internet <URL: http://www.flexibletechnology.com/Flexible circuits Capability.htm >.
"Flex Circuits/flexible circuits design guide," [online] [retrieved on Aug. 28, 2006] Retrieved from the Internet <URL: http://flexiblecircuit.co.uk/Flex Circuits Design Guide.htm >.
"Insect Stings Auto-injector Pouches and Carry Cases," The Insect Stings On-Line Shop, [online] [retrieved on Jan. 24, 2007] Retrieved from the Internet <URL: http://www.insectstings.co.uk/acatalog/Auto Injector Pouches.html >.
"Anaphylaxis Canada Product Catalogue," Anaphylaxis Canada > Living with Anaphylaxis > Tools and Resources [online] [retrieved on Jan. 24, 2007] Retrieved from the Internet <URL: http://anaphylaxis.org/content/livingwith/productcatalogue.asp >.
"Microfluidics Device Provides Programmed, Long-Term Drug Dosing," nano techwire.com [online] [retrieved on Nov. 28, 2006] Retrieved from the Internet <URL: http://nanotechwire.com/news.asp?nid=3141&ntid-124&pg=1 >.
Roger Allan, "Medical Electronics: Technology Advances Will Revolutionize Healthcare," Sep. 30, 2002 [online] [retrieved on Nov. 28, 2006] Retrieved from the Internet <URL: http://www.elecdesign.com/Articles/Index.cfm?AD=1&ArticleID=2041>.
RFID Gazette, "Smart Labels in Healthcare," Sep. 29, 2005 [online] [retrieved on Nov. 28, 2006] Retrieved from the Internet <URL: http://www.rfidagazeete.org/2005/09/smart labels in.html >.
"Merck Serono Launches easypod(R), First Electronic Growth Hormone Injection Device," Jan. 30, 2007 [online] [retrieved on Feb. 5, 2007] Retrieved from the Internet <URL: http://www.biz.yahoo.com/prnews/070130/ukm028.html?.v=8.
Dr. Oliver Scholz, "Drug depot in a tooth," [online] [retrieved on Feb. 6, 2007] Retrieved from the Internet <URL: http://www.fraunhofer.de/fhg/EN/press/pi/2007/02Mediendienst22007Thema2.jsp?print=true.
Heartsine Technology, samaritan™ PAD ACCESSORIES [online] [retrieved on Jun. 1, 2007] Retrieved from the Internet <URL: http://www.heartsine.com/aboutsam-accessories.htm>.
CliniSense Corporation, "Drug delivery devices A potentially harsh environment for drugs," Stability [online] [retrieved on Jun. 1, 2007] Retrieved from the Internet <URL: http://www.clinisense.com/devices.htm>.
CliniSense Corporation, "LifeTrack Technology A new method to detect improper storage." Stability [online] [retrieved on Jun. 1, 2007] Retrieved from the Internet <URL: http://www.clinisense.com/tech.htm>.
AED Professionals™ Brochure [online] [retrieved on Jun. 1, 2007] Retrieved from the Internet <URL: http://www.aedprofessionals.com/>.
Daniel Ruppar, "Implant Technologies Expected to Remain a Niche but Effective Method of Drug Delivery," Drug Delivery Technology, Feb. 2007, vol. 7, No. 2 [online] [retrieved on Jun. 1, 2007] Retrieved from the Internet <URL: http://www.drugdeliverytech-online.com/drugdelivery/200702/templates/pageviewer_print?pg=44&pm=8 >.
Search Report and Written Opinion for International Patent Application No. PCT/US06/03415 mailed Jul. 13, 2006, 10 pages.
Search Report and Written Opinion for International Patent Application No. PCT/US07/84891 mailed Sep. 15, 2008, 7 pages.
Search Report and Written Opinion for International Patent Application No. PCT/US07/007626 mailed Sep. 29, 2008.
Examination Report for British Patent Application No. GB 0708523.6, mailed Dec. 8, 2008.
Combined Search and Examination Report for British Patent Application No. GB 0713202.0, mailed Dec. 1, 2008.
Examination Report for British Patent Application No. GB 0822532.8, mailed Jan. 21, 2009.
Office Action for U.S. Appl. No. 11/562,061, mailed Feb. 3, 2009.
Examination Report for British Patent Application No. GB 0822532.8, mailed May 21, 2009.

(56) References Cited

OTHER PUBLICATIONS

Examination Report for New Zealand Patent Application No. NZ 589864, mailed Dec. 14, 2010.
Search and Examination Report for British Patent Application No. 1105021.8, mailed May 18, 2011.
Office Action for U.S. Appl. No. 11/692,359, mailed Jul. 18, 2011.
International Search Report and Written Opinion for International Application No. PCT/US2012/022698, mailed May 25, 2012.
Office Action for U.S. Appl. No. 13/053,451, mailed Nov. 15, 2012.
English Translation of Office Action for Japanese Patent Application No. 2011-257810, mailed Mar. 13, 2013.
Office Action for Canadian Patent Application No. 2,669,616 mailed Dec. 23, 2013.
Office Action for Japanese Patent Application No. JP2007-553358, mailed Feb. 24, 2010.
Examination Report for Australian Patent Application No. 2012211320, mailed Jan. 28, 2014.
Office Action for Japanese Patent Application No. 2013-551328, mailed Jan. 13, 2016.
Invitation to Pay Additional Fees and, Where Applicable, Protest Fee, PCT Application No. PCT/US2016/023995, dated May 17, 2016.

\* cited by examiner

DEVICES AND METHODS FOR DELIVERING MEDICAMENTS FROM A MULTI-CHAMBER CONTAINER

CROSS-REFERENCE TO RELATED APPLICATIONS

This application claims priority to U.S. Provisional Application Ser. No. 61/650,196, entitled "Devices and Methods for Delivering Medicaments from a Multi-Chamber Container," filed May, 22, 2012, which is incorporated herein by reference in its entirety.

BACKGROUND

The embodiments described herein relate generally to an injector, and more particularly to a medicament delivery device for mixing a medicament and delivering the medicament into a body of a patient.

Exposure to certain substances, such as, for example, peanuts, shellfish, bee venom, certain drugs, toxins, and the like, can cause allergic reactions in some individuals. Such allergic reactions can, at times, lead to anaphylactic shock, which can cause a sharp drop in blood pressure, hives, and/or severe airway constriction. Accordingly, responding rapidly to mitigate the effects from such exposures can prevent injury and/or death. For example, in certain situations, an injection of epinephrine (i.e., adrenaline) can provide substantial and/or complete relief from the allergic reaction. In other situations, for example, an injection of an antidote to a toxin can greatly reduce and/or eliminate the harm potentially caused by the exposure. Similarly, an injection of glucagon can reduce and/or eliminate the harm potentially caused by reduced blood glucose levels in individuals who suffer from hypoglycemia.

Because emergency medical facilities are not always available when an individual is suffering from a medical condition, some individuals carry an auto-injector to rapidly self-administer a medicament in response to such medical conditions. Some known auto-injectors include a vial containing a liquid medicament and a spring loaded needle to automatically penetrate the user's skin and inject the medicament. The storage of certain medicaments in a liquid form, however, can result in a shorter shelf life and/or an unstable medicament. Accordingly, some known auto-injectors include a vial containing a first medicament that is separated from a second medicament. Such auto-injectors are often referred to as "wet/dry" auto-injectors, because one medicament is often a liquid (e.g., water or another diluent) and the other medicament can be substantially solid or dry (e.g., glucagon powder). In use, the first medicament and the second medicament must be mixed prior to injection.

Some known wet/dry injectors, however, require that the user manually actuate a mixing mechanism prior to injection (e.g., by twisting a portion of the device to complete the mixing step). Such configurations can, however, result in incomplete mixing and/or an injection occurring without mixing. In addition, the operation of some known wet/dry delivery systems includes manually inserting the needle into the skin prior to activation and subsequent medicament delivery. The operation of such configurations may also include separately attaching a needle to prepare the device for injection, resulting in a delay in delivery of the medicament. Moreover, such configurations can be complicated, making them difficult for a user to operate during an emergency situation or by an individual without medical training.

Some known wet/dry injectors employ a single mechanism to automatically mix and inject the medicaments contained therein. Because the mixing operation is not independent from the injection operation in such configurations, however, the medicament can be injected prior to the completion of the mixing operation and/or prior to the injector being properly positioned for the injection operation.

Some known wet/dry injectors are configured such that a user can manually vent and/or purge a portion of air included in the medicament container (e.g., mixed with or a part of the glucagon powder). In some embodiments, such known injectors are generally oriented in a predetermined manner (e.g., with the needle end facing upward) to facilitate the venting process. Therefore, the venting process can be performed incorrectly or incompletely.

Thus, a need exists for an improved auto-injector that can separately store two or more medicaments and that can vent, mix and inject the medicaments in distinct operations. A need also exists for improved methods of filling medicament containers used in such devices.

SUMMARY

Medicament delivery devices for mixing a medicament and delivering the medicament and/or multi-stages of actuation are described herein. In some embodiments, an apparatus includes a medicament container, a first elastomeric member, a second elastomeric member and a stopper. The medicament container is configured to be movably coupled to a carrier of a medicament delivery device. The carrier includes a needle. The first elastomeric member is disposed within a proximal end portion of the medicament container. The second elastomeric member is disposed within the medicament container. The first elastomeric member, a first portion of the medicament container and the second elastomeric member collectively define, at least in part, a medicament volume. The stopper is coupled to a distal end portion of the medicament container. The second elastomeric member, a second portion of the medicament container and the stopper collectively define, at least in part, a vent volume. The stopper has a first retention portion and a second retention portion. The first retention portion is configured to engage a first portion of the carrier to limit movement of the medicament container relative to the carrier when the medicament container is in a first position relative to the carrier. The second retention portion is configured to engage a second portion of the carrier to limit movement of the medicament container relative to the carrier when the medicament container is in a second position relative to the carrier.

BRIEF DESCRIPTION OF THE DRAWINGS

FIGS. 31-35 are cross-sectional views of the medical injector taken along the line $X_3$-$X_3$ in FIG. 28, in a third, fourth, fifth, and sixth configuration, respectively.

DETAILED DESCRIPTION

Figure 1:
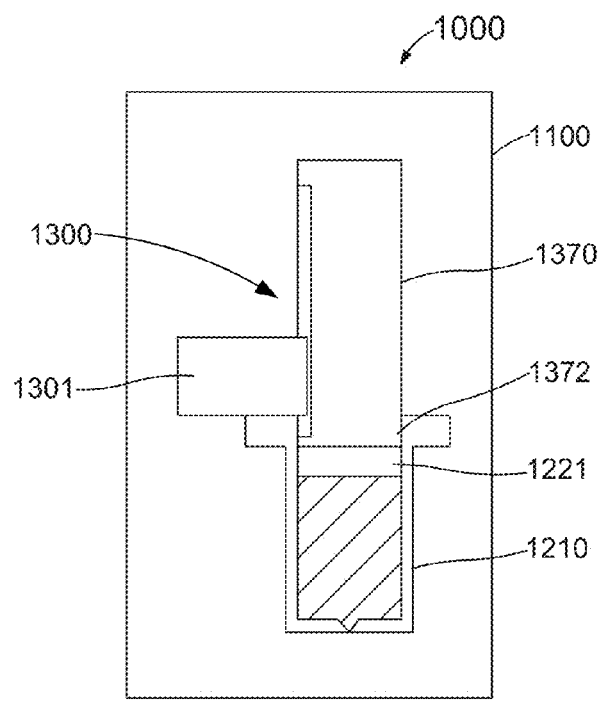
FIGS. 1-4 are schematic illustrations of a medicament delivery device according to an embodiment, in a first, second, third, and fourth configuration, respectively.

Medicament delivery devices for mixing and/or delivering a medicament are described herein. In some embodiments, an apparatus includes a medicament container, a first elastomeric member, a second elastomeric member and a stopper. The medicament container is configured to be movably coupled to a carrier of a medicament delivery device. The carrier includes a needle. The first elastomeric member is disposed within a proximal end portion of the medicament container. The second elastomeric member is disposed within the medicament container. The first elastomeric member, a first portion of the medicament container and the second elastomeric member collectively define, at least in part, a medicament volume. The stopper is coupled to a distal end portion of the medicament container. The second elastomeric member, a second portion of the medicament container and the stopper collectively define, at least in part, a vent volume. The stopper has a first retention portion and a second retention portion. The first retention portion is configured to engage a first portion of the carrier to limit movement of the medicament container relative to the carrier when the medicament container is in a first position relative to the carrier. The second retention portion is configured to engage a second portion of the carrier to limit movement of the medicament container relative to the carrier when the medicament container is in a second position relative to the carrier.

In some embodiments, an apparatus includes a housing, a medicament container, and a movable assembly. The movable assembly includes a first movable member and a second movable member. The second movable member is configured to move relative to the first movable member to change the movable assembly from a first configuration to a second configuration. A distal end portion of the second movable member is configured to move a plunger disposed within the medicament container in a distal direction when the movable assembly is changed to the second configuration. The movable assembly is configured to move between a first position and a second position to move the medicament container within the housing between a first container position and a second container position.

In some embodiments, a medicament delivery device includes a housing, a medicament container, and a movable assembly. The movable assembly is configured to increase in length when moved from a first configuration to a second configuration to move a plunger disposed within the medicament container a first distance. The movable assembly is configured to move between a first position and a second position within the housing to move the plunger a second distance.

In some embodiments, a medicament delivery device includes a housing, a medicament container, a movable member, and a release member. The movable member is configured to move a plunger disposed within the medicament container. The release member includes a first end portion and a second end portion. The second end portion is configured to move between a first position and a second position. In the first position, the second end portion of the release member is configured to limit the movement of the movable member. The second end portion is configured such that when the first end portion is moved in a first direction, the second end portion is moved in a second direction, substantially different from the first, from the first position to the second position.

As used in this specification and the appended claims, the term "medicament" includes any constituent of a therapeutic substance. A medicament can include such constituents regardless of their state of matter (e.g., solid, liquid or gas). Moreover, a medicament can include the multiple constituents that can be included in a therapeutic substance in a mixed state, in an unmixed state and/or in a partially mixed state. A medicament can include both the active constituents and inert constituents of a therapeutic substance. Accordingly, as used herein, a medicament can include non-active constituents such as, water, colorant or the like.

As used herein, the words "proximal" and "distal" refer to direction closer to and away from, respectively, an operator of the medical device. Thus, for example, the end of the medicament delivery device contacting the patient's body would be the distal end of the medicament delivery device, while the end opposite the distal end would be the proximal end of the medicament delivery device.

FIGS. 1-4 are schematic illustrations of a medicament delivery device 1000 according to an embodiment in a first, second, third and fourth configuration, respectively. The medicament delivery device 1000 includes a housing 1100, a medicament container 1210, and a movable assembly 1300. The housing 1100 can be any suitable size, shape, or configuration and can be made of any suitable material. For example, in some embodiments, the housing 1100 is an assembly of multiple parts formed from a plastic material and defines a substantially rectangular shape when assembled.

The medicament container 1210 is disposed within the housing 1100, and contains (i.e., is filled or partially filled with) a medicament. The medicament container 1210 includes a proximal end portion and a distal end portion that can be coupled to a delivery member, such as a tube, a needle or the like (not shown in FIGS. 1-4). The medicament container 1210 further includes an elastomeric member 1221 (also referred to herein as a "plunger"). The elastomeric member 1221 is formulated to be compatible with the medicament housed within the medicament container 1210. Similarly stated, the elastomeric member 1221 is formulated to minimize any reduction in the efficacy of the medicament that may result from contact (either direct or indirect) between the elastomeric member 1221 and the medicament. For example, in some embodiments, the elastomeric member 1221 can be formulated to minimize any leaching or out-gassing of compositions that may have an undesired effect on the medicament. In some embodiments, the elastomeric member 1221 can be disposed within the medicament container 1210 to seal the proximal end portion of the medicament container 1210. In some embodiments, the elastomeric member 1221 can be formulated to maintain its chemical stability, flexibility and/or sealing properties when in contact (either direct or indirect) with a medicament over a long period of time (e.g., for up to six months, one year, two years, five years or longer). The medicament container 1210 can be any container suitable for storing the medicament.

The movable assembly 1300 includes a first movable member 1301 and a second movable member 1370 and is movable between a first configuration and a second configuration. The first movable member 1301 and the second movable member 1370 are movably coupled together such that the second movable member 1370 can move with and/or relative to the first movable member 1301. For example, in some embodiments, the second movable member 1370 can include a channel that receives a protrusion included in the first movable member 1301. In this manner, the protrusion of the first movable member 1301 can move within the channel of the second movable member 1370 such that the second movable member 1370 can move relative to the first movable member 1301 while remaining coupled to the first movable member 1370.

Figure 2:
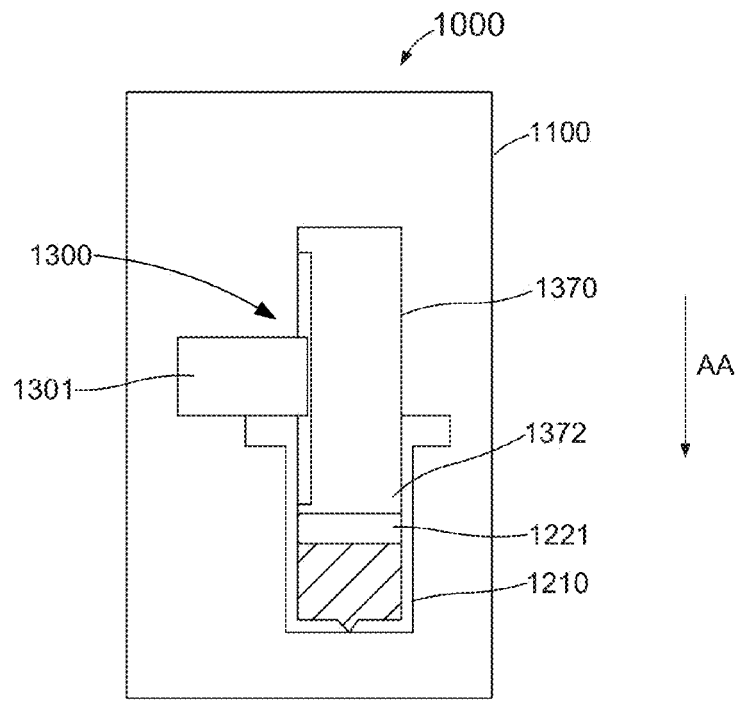

As shown in FIG. 1, the second movable member 1370 includes a distal portion 1372 that engages the plunger 1221 disposed within the medicament container 1210. In some embodiments, the distal end portion 1372 of the second movable member 1370 can be spaced apart from the plunger 1221 when the movable assembly 1300 is in a first configuration (e.g., FIG. 1). The second movable member 1370 can be any suitable mechanism for contacting and/or moving the plunger 1221. For example, in some embodiments, the second movable member 1370 can be a piston that includes a base disposed at the distal end portion 1372 that engages the plunger 1221. The second movable member 1370 can be moved, relative to the first movable member 1301 to move the movable assembly 1300 from the first configuration to a second configuration (FIG. 2). When the second movable member 1370 moves relative to the first movable member 1301, the distal end portion 1372 can move the plunger 1221 in the distal direction within the medicament container 1210, as shown by the arrow AA in FIG. 2. The distal motion of the plunger 1221 can facilitate, for example, a mixing of medicament constituents contained within the medicament container 1210. For example, in some embodiments, the medicament can include a first medicament portion (or constituent) and a second medicament portion (or constituent) configured to mix when pressurized. In some embodiments, the distal movement of the plunger 1221 can facilitate the release of a pressurized gas. In some embodiments, a pressurized gas can be included within the medicament container to separate a first medicament portion (or constituent) from a second medicament portion (or constituent) when the movable assembly 1300 is in the first configuration. Therefore, when the pressurized gas is released, the first medicament portion mixes with the second medicament portion. In yet other embodiments, the distal movement of the plunger 1221 can facilitate the release of gas that is undesirably contained within the medicament prior to delivery of the medicament.

In some embodiments, the second movable member 1370 can be configured to move in the direction AA (e.g., the distal direction) in response to a force exerted by a user (e.g., via direct contact, a pull tab, a slider, and/or the like). In some embodiments, the second movable member 1370 can be configured to move in the direction AA (e.g., the distal direction) in response to a force exerted by an energy storage member (not shown in FIGS. 1-4). In such embodiments, an energy storage member can be any suitable mechanism or device for storing energy. For example, the energy storage member can be a mechanical energy storage member, such as a spring, a device containing compressed gas, a device containing a vapor pressure-based propellant or the like. In other embodiments, the energy storage member can be an electrical energy storage member, such as a battery, a capacitor, a magnetic energy storage member or the like. In yet other embodiments, the energy storage member can be a chemical energy storage member, such as a container containing two substances that, when mixed, react to produce energy. By employing the energy storage member to produce the force rather than relying on a user to manually produce the delivery force, the plunger 1221 can be moved at the desired pressure and/or with the desired force. Moreover, this arrangement reduces the likelihood of partial or improper movement of the plunger 1221 (e.g., that may result if the user is interrupted or otherwise rendered unable to manually produce the force to complete the movement of the second movable member 1370).

Figure 3:
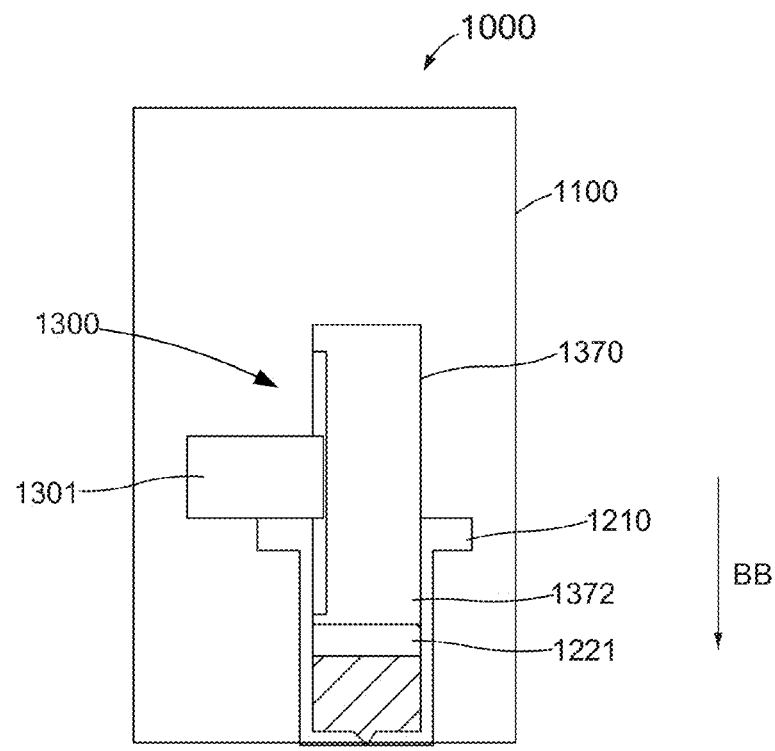
Figure 4:
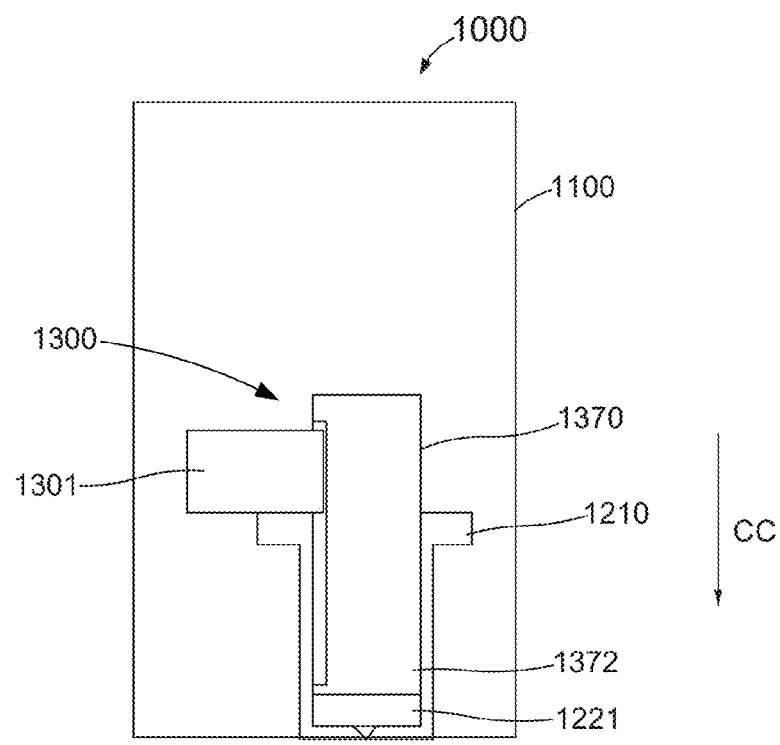

The movable assembly 1300 is configured to move from a first position (e.g., FIG. 1) to a second position (e.g., FIG. 3) within the housing 1100, as shown by the arrow BB in FIG. 3. In some embodiments, the movable assembly 1300 can move in the direction BB (e.g., the distal direction) in response to a portion of the force exerted by the energy storage member (described above). In other embodiments, the movable assembly 1300 can move in the distal direction in response to a second force exerted by the energy storage member. In other embodiments, the movable assembly 1300 can be in contact with or operably coupled to a second energy storage member (different from an energy storage member used to move the second movable member 1370) configured to exert the second force on the movable assembly 1300. In still other embodiments, the movable assembly 1300 can be manually moved to the second position (e.g., as described above).

The distal movement of the movable assembly 1300 is configured to move the medicament container 1210 within the housing 1100 from a first container position (e.g., FIG. 2) to a second container position. In some embodiments, the distal movement (e.g., in the direction of the arrow BB shown in FIG. 3) can facilitate the insertion of a needle, disposed at the distal end portion of the medicament container 1210, into a target location (e.g., the body of a patient). Furthermore, with the medicament container 1210 in the second container position within the housing 1100, the second movable member 1370 can continue to move in the distal direction, as shown by the arrow CC in FIG. 4. In this manner, the second movable member 1370 can move relative to the first movable member 1301 to move the plunger 1221 within the medicament container 1210 such that the medicament disposed therein is delivered to a volume substantially outside the medicament container 1210 (e.g., into the body of the patient via the needle).

Although the length of the movable assembly 1300, as measured along a longitudinal axis thereof, is substantially constant when the movable assembly 1300 is changed from the first configuration (FIG. 1) to the second configuration (FIG. 2) and/or to the third configuration (FIG. 4), in other embodiments, the length of the movable assembly 1300 can change when the movable assembly 1300 changes between various configurations. Similarly stated, although the overall length of the movable assembly 1300 is the same as the length of the second movable member 1370, and remains the same in the configurations shown in FIGS. 1-4, in other embodiments, the overall length of the movable assembly 1300 can change when the movable assembly 1300 when the movable assembly 1300 changes between various configurations. Furthermore, while the medicament containers described above include a single plunger, in some embodiments, any of the medicament containers described herein can include any number of plungers and/or can define multiple volumes therein that contain different medicament constituents. For example, as shown in FIGS. 5-8, a medicament delivery device 2000 includes a housing 2100, a medicament container 2210, and a movable assembly 2300. The housing 2100 can be any suitable size, shape, or configuration and can be made of any suitable material. For example, in some embodiments, the housing 2100 is an assembly of multiple parts formed from a plastic material and defines a substantially rectangular shape when assembled.

The medicament container 2210 is disposed within the housing 2100, and includes a first plunger 2221, a second plunger 2225, and a bypass 2220. The medicament container 2210 defines a first volume 2236, and a second volume 2237. Expanding further, the first volume 2236 is defined between a distal end surface of the first plunger 2221, a portion of the medicament container 2120 and a proximal end surface of the second plunger 2225. The first volume 2236 can contain a first substance, such as any suitable diluent, as described in further detail herein. Similarly, the second volume 2237 is defined between a distal end surface of the second plunger and a distal end portion of the medicament container 2210. The second volume 2237 can contain a second substance, such as any suitable medicament (e.g., a lyophilized medicament). In this manner, the diluent contained within the first volume 2236 can be stored separately from with the medicament within the second volume 2237. Upon actuation the diluent can be mixed with the medicament such that the combination of the diluents and the medicament reconstitute the medicament for delivery into, for example, the body of a patient.

The movable assembly 2300 includes a first movable member 2301 and a second movable member 2370, and is movable between a first configuration, a second configuration, and a third configuration. The first movable member 2301 and the second movable member 2370 are movably coupled such that the second movable member 2370 can move with and/or relative to the first movable member 2301. As shown, in some embodiments, the second movable member 2370 can substantially surround the first movable member 2301. In some embodiments, the second movable member 2370 can define a substantially annular and/or cylindrical shape such that at least a portion of the first movable member 2301 is disposed therein.

Figure 5:
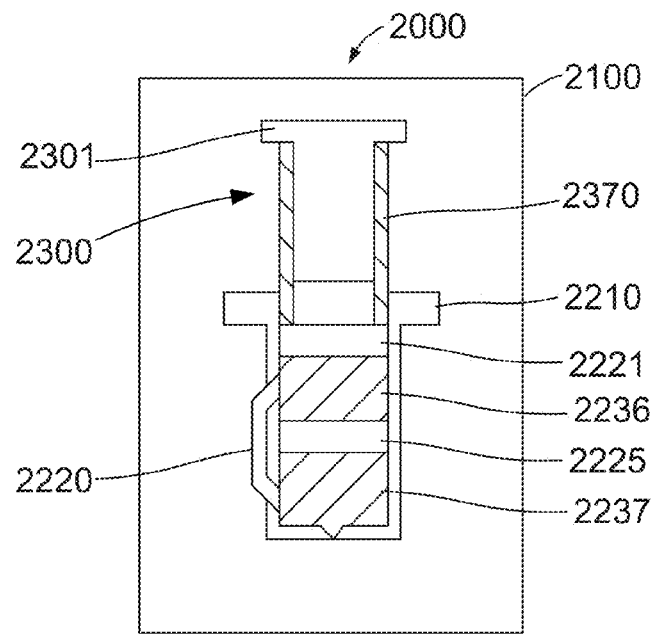
FIGS. 5-8 are schematic illustrations of a medicament delivery device according to an embodiment, in a first, second, and third configuration, respectively.
Figure 6:
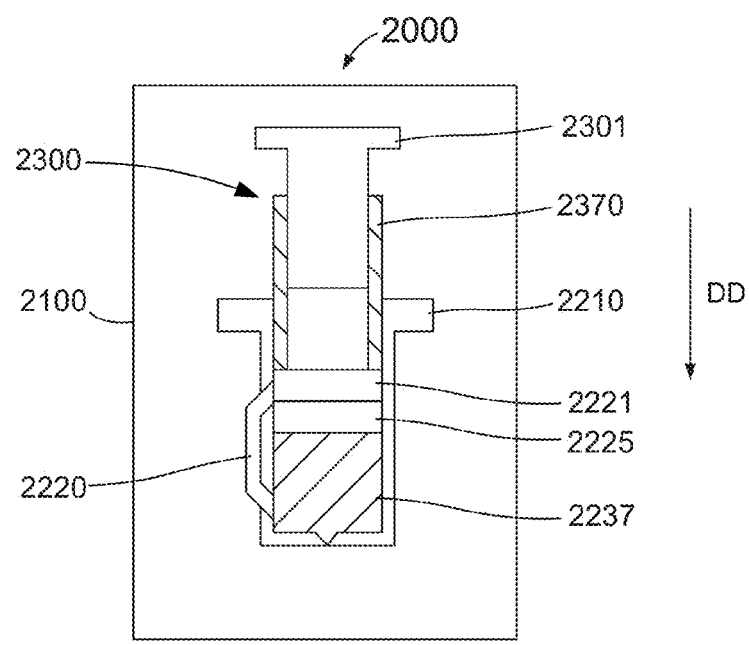

As shown in FIG. 5, the second movable member 2370 engages the first plunger 2221 disposed within the medicament container 2210 and when the movable assembly 2300 is in the first configuration. In other embodiments, the second movable member 2370 can be spaced apart from the plunger 2221 when the movable assembly 2300 is in the first configuration. The second movable member 2370 can be moved, relative to the first movable member 2301 to move the movable assembly 2300 from the first configuration to the second configuration. For example, in some embodiments, the second movable member 2370 can be moved by a force exerted by an energy storage member (e.g., such as those described herein). When the second movable member 2370 moves relative to the first movable member 2301, a distal end portion of the second movable member 2370 moves the first plunger 2221 in the distal direction within the medicament container 2210, as shown by the arrow DD in FIG. 6. The distal motion of the plunger 2221 can facilitate, for example, a mixing of diluents and the medicament contained within the medicament container 2210. For example, in some embodiments, the distal movement of the first plunger 2221 can cause the second plunger 2225 to move past the bypass 2220 and urge the diluent, contained within the first volume 2236 to move within the bypass 2220 and enter the second volume 2237.

The bypass 2220 can be any suitable bypass (external or internal) configured to define a pathway between the first volume 2236 and the second volume 2237. In some embodiments, the bypass 2220 can include a one way valve such that when a pressure within the first volume 2236 increases (e.g., as induced by the distal movement of the first plunger 2221), the one way valve opens to allow a flow of the diluent through the bypass 2220 to the mixing volume 2237. In other embodiments, the bypass 2220 can include a frangible seal configured to break under the increase pressure. In this manner, when first plunger 2221 is moved, the first volume 2236 is reduced and the distal end surface of the first plunger 2221 can contact the proximal end surface of the second plunger 2255. Accordingly, as the volume defined by the first volume 2236 is reduced, the volume of the second volume 2237 increases. In this manner, the distal end surface of the first plunger 2221 contacts the proximal end surface of the second plunger 2225 at a position within the medicament container 2210 such that the first plunger 2221 of the second plunger 2225 substantially seals an opening of the bypass 2220, thereby preventing potential backflow.

Figure 7:
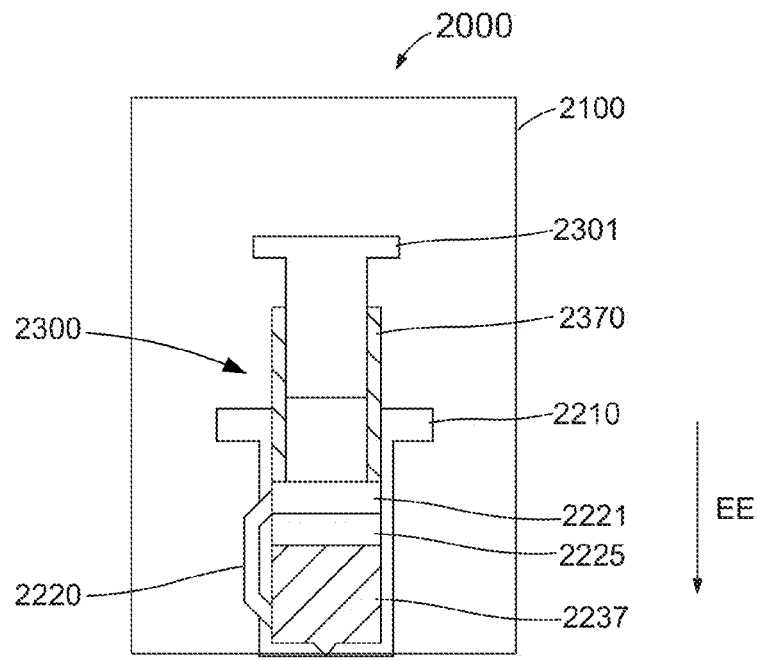
Figure 8:
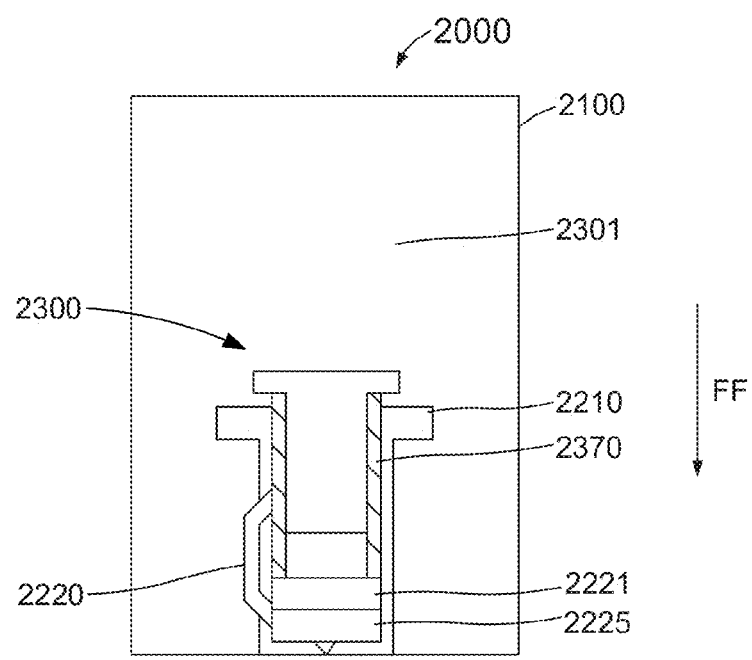

The movable assembly 2300 is configured to move from a first position (e.g., FIG. 14) to a second position within the housing 2100, as shown by the arrow EE in FIG. 7. In some embodiments, the movable assembly 2300 can move in the direction EE (e.g., the distal direction) in response to a portion of a force exerted, for example, by the energy storage member (described above). The distal movement of the movable assembly 2300 moves the medicament container 2210 within the housing 2100 from a first container position (e.g., FIG. 15) to a second container position (e.g., FIG. 7). In some embodiments, the distal movement (e.g., in the direction of the arrow EE shown in FIG. 16) can facilitate the insertion of a needle (not shown in FIGS. 5-8), disposed at the distal end portion of the medicament container 2210, into a target location (e.g., the body of a patient).

When the medicament container 2210 is in the second container position within the housing 2100, the first movable member 2301 moves distally to engage the second movable member 2370. In this manner, the first movable member 2301 and the second movable member 2370 can move together in the distal direction, as shown by the arrow FF in FIG. 8. Thus, the movable assembly 2300 moves in the distal direction and moves the first plunger 2221 and the second plunger 2225 within the medicament container 2210 such that the medicament disposed within the second volume 2237 is delivered to a volume substantially outside the medicament container 2210 (e.g., into the body of the patient via the needle).

Figure 9:
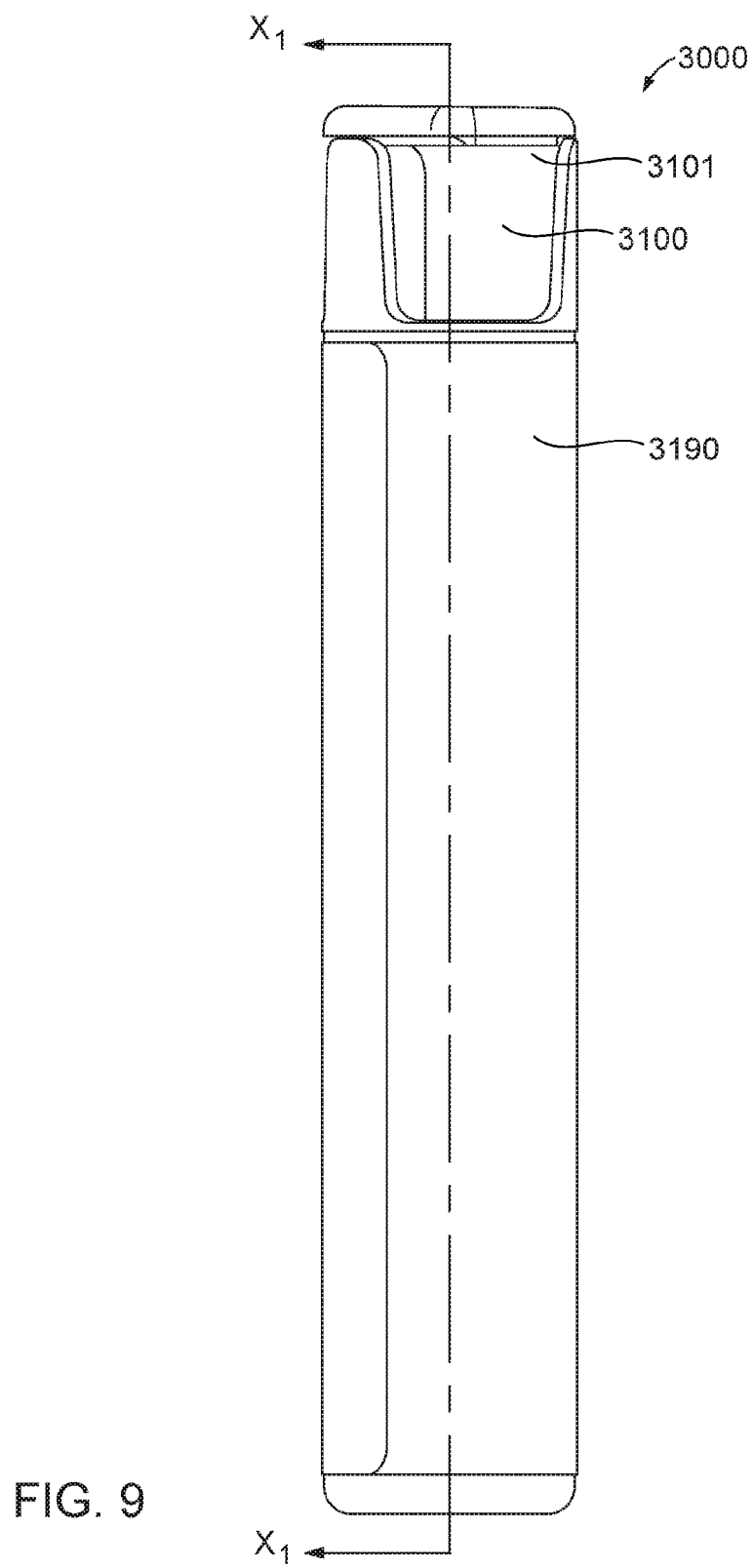
FIG. 9 is a side view of a medical injector, according to an embodiment.
Figure 10:
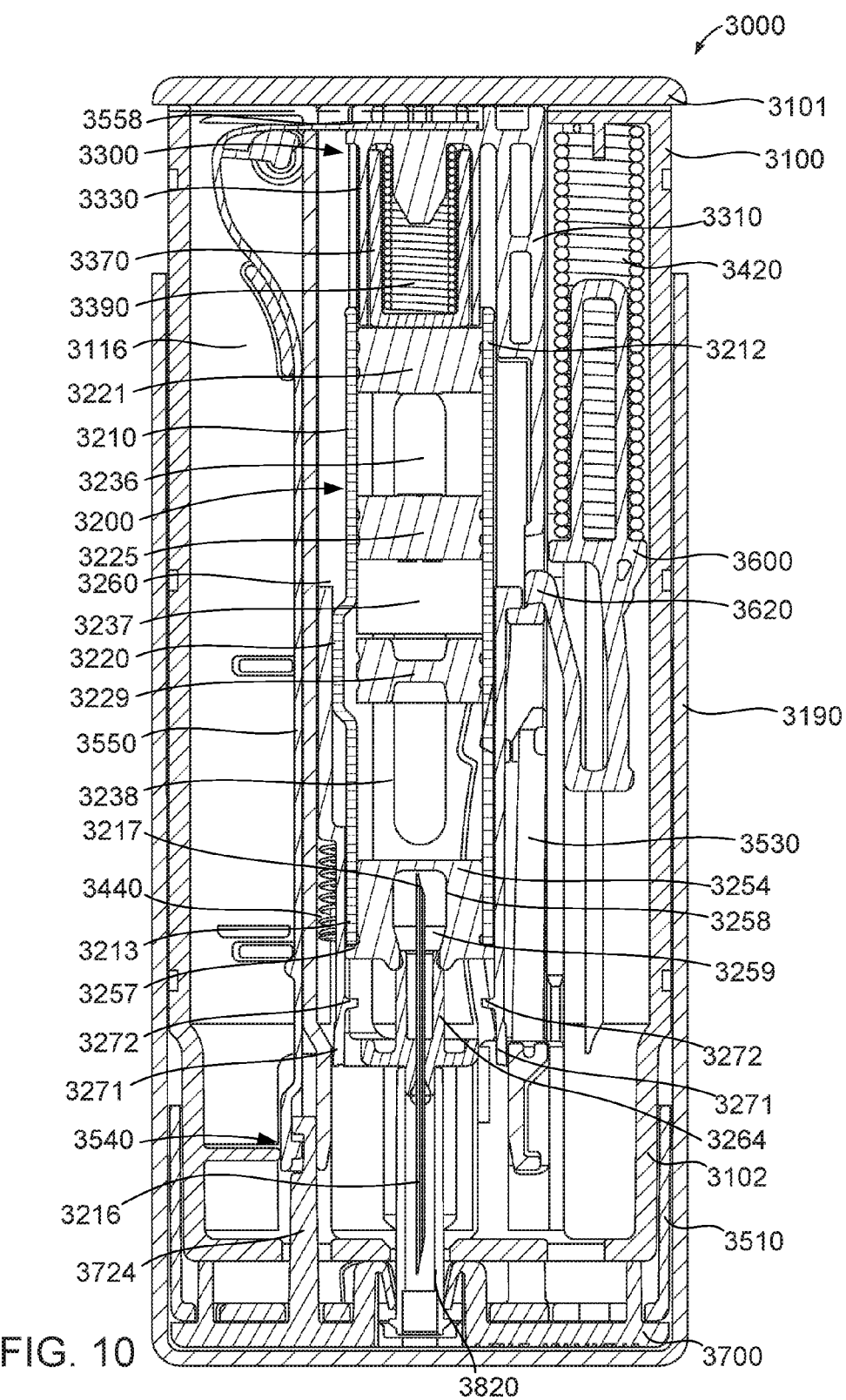
FIG. 10 is a cross-sectional view of the medical injector taken along the line $X_1$-$X_1$ in FIG. 9, in a first configuration.

In some embodiments, the medicament delivery device can be a medical injector configured to automatically vent, mix and deliver a medicament contained within a medicament container. For example, FIGS. 9-19 show various views of a medical injector 3000, according to an embodiment in various different configurations (or stages of operation). FIG. 9 is a side view of the medical injector 3000 in a first configuration. As shown in FIG. 10, the medical injector 3000 includes a housing 3100, a system actuator assembly 3500, a medicament container assembly 3200 containing a medicament 3240, a movable assembly 3300, a transfer member 3600, a cover 3190, and a safety lock 3700. In some embodiments, the medical injector 3000 can be similar in function and/or structure to any of the medical injectors discussed in U.S. patent application Ser. No. 13/357,936, entitled "Devices and Methods for Delivering Medicaments From a Multi-Chamber Container," filed on Jan. 25, 2012, which is incorporated by reference in its entirety (the '936 application).

The housing 3100 has a proximal end portion 3101 and a distal end portion 3102. The proximal end portion 3102 includes an end cap configured to substantially enclose the proximal end. The distal end portion 3103 can include any suitable feature to engage and/or otherwise receive at least a portion of the system actuator 3500 (e.g., a base 3510). For example, the distal end portion 3103 can include recesses, grooves, slots, notches, openings, protrusions and/or any other suitable feature. The housing 3100 is configured to substantially enclose and/or otherwise house at least a portion of the system actuator assembly 3500, the medicament container assembly 3200, the movable assembly 3300, the transfer assembly 3600, and the safety lock 3700. In some embodiments, the housing 3100 can be configured to further house an electronic system (not shown herein). For example, in some embodiments, the housing can enclose an electric system substantially similar to any of the electronic systems described in the '936 application.

The distal end portion 3100 of the housing 3100 is configured to receive an activator 3530 (also referred to herein as "release member 3530," and/or "rod 3530" included in the base 3510 of the system actuator assembly 3500. As described in more detail herein, the release member 3530 of the base 3510 is configured to engage a portion of the movable assembly 3300 (also referred to herein as "medicament delivery mechanism 3300") when the base 3510 is moved with respect to the housing 3100 to actuate the medical injector 3000. The housing 3100 includes an inner surface 3116 that can include any suitable feature configured to limit, guide, contact, separate, and/or otherwise engage a portion of the medicament container assembly 3200, the system actuator assembly 3500, the movable assembly 3300, the transfer assembly 3600, and the safety lock 3700. For example, the inner surface 3116 can include guides (not shown herein) configured to engage at least a portion of the medicament container assembly 3200 as the medicament container assembly 3200 moves from a proximal position, relative to the housing 3100, to a distal position, relative to the housing 3100. Furthermore, the housing 3100 define an opening (not shown herein) that receives a portion of a needle 3216 of the medicament container assembly 3200 such that the needle 3216 is disposed substantially outside the housing 3100 when the medicament container assembly 3200 is in the distal position, as described in further detail herein.

As shown in FIGS. 9 and 10, the cover 3190 is configured to be disposed about a portion of the housing 3100. Thus, when the portion of the housing 3100 is disposed within the cover 3190, the cover 3190 blocks an optical pathway between the medicament container 3210 and a region outside of the housing 3100. Similarly stated, when the portion of the housing 3100 is disposed within the cover 3190, the cover 3190 reduces the amount of light transmitted to the medicament within the medicament container 3210. In this manner, the life of the medicament can be extended by the prevention and/or reduction of degradation to the medicament that may be caused by ultra-violet radiation.

Figure 11:
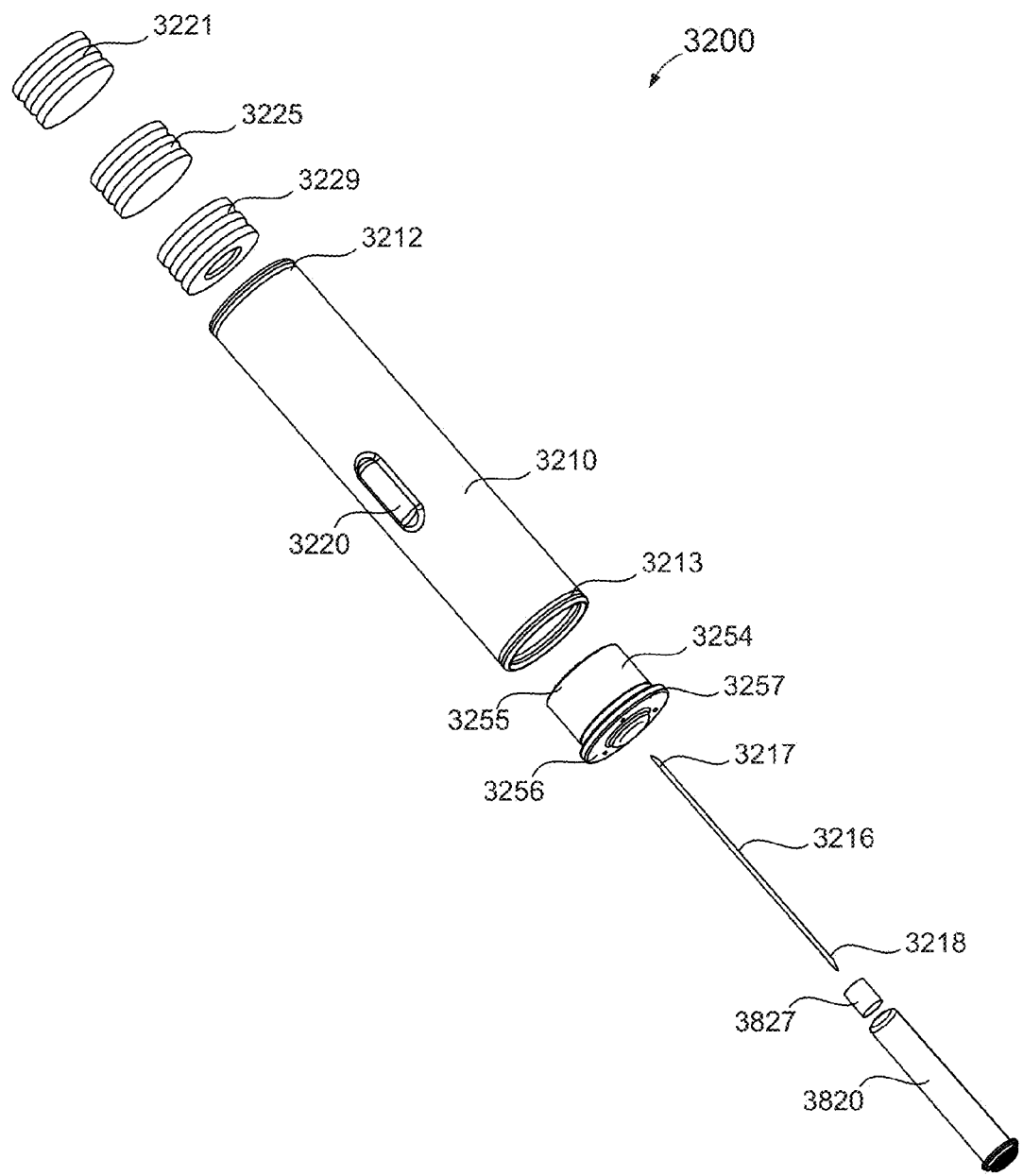
FIG. 11 is an exploded perspective view of a medicament assembly included in the medical injector of FIG. 9.
Figure 12:
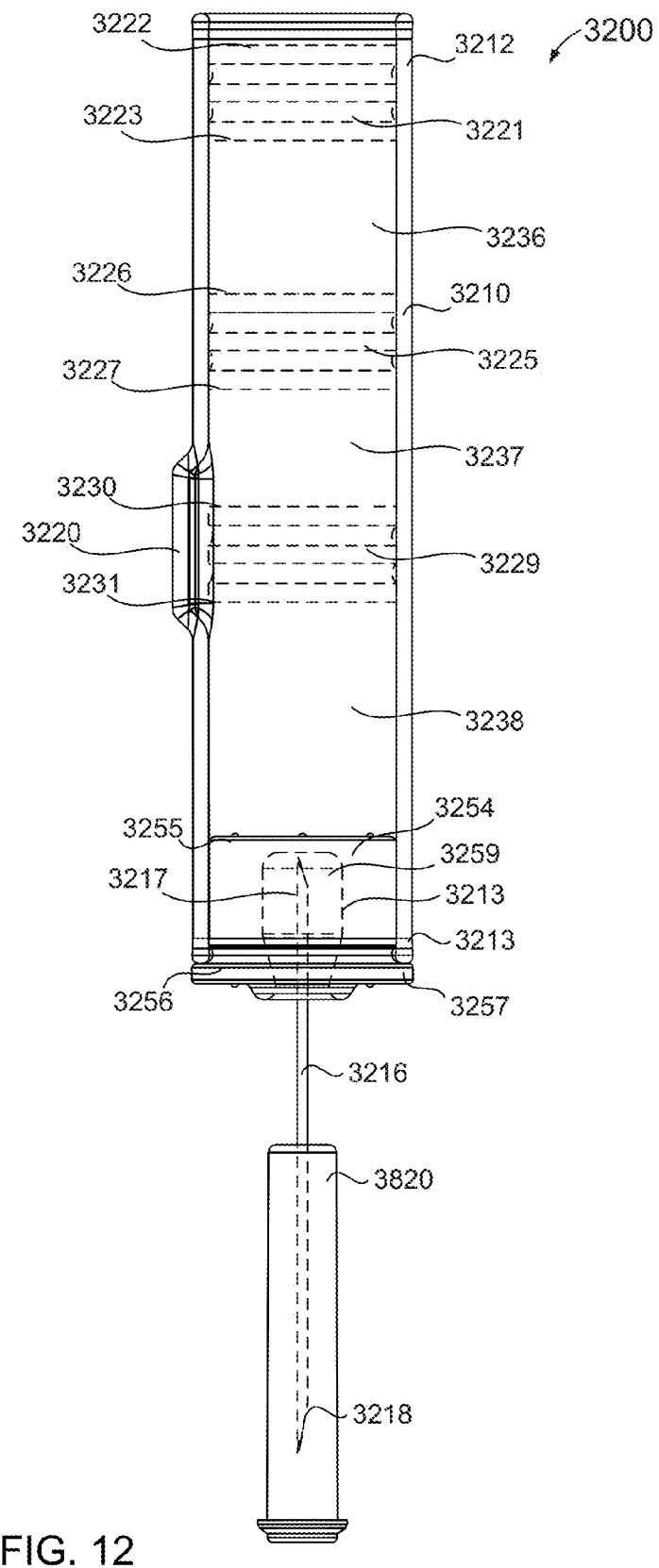
FIG. 12 is a front view of the medicament assembly of FIG. 11.
Figure 13:
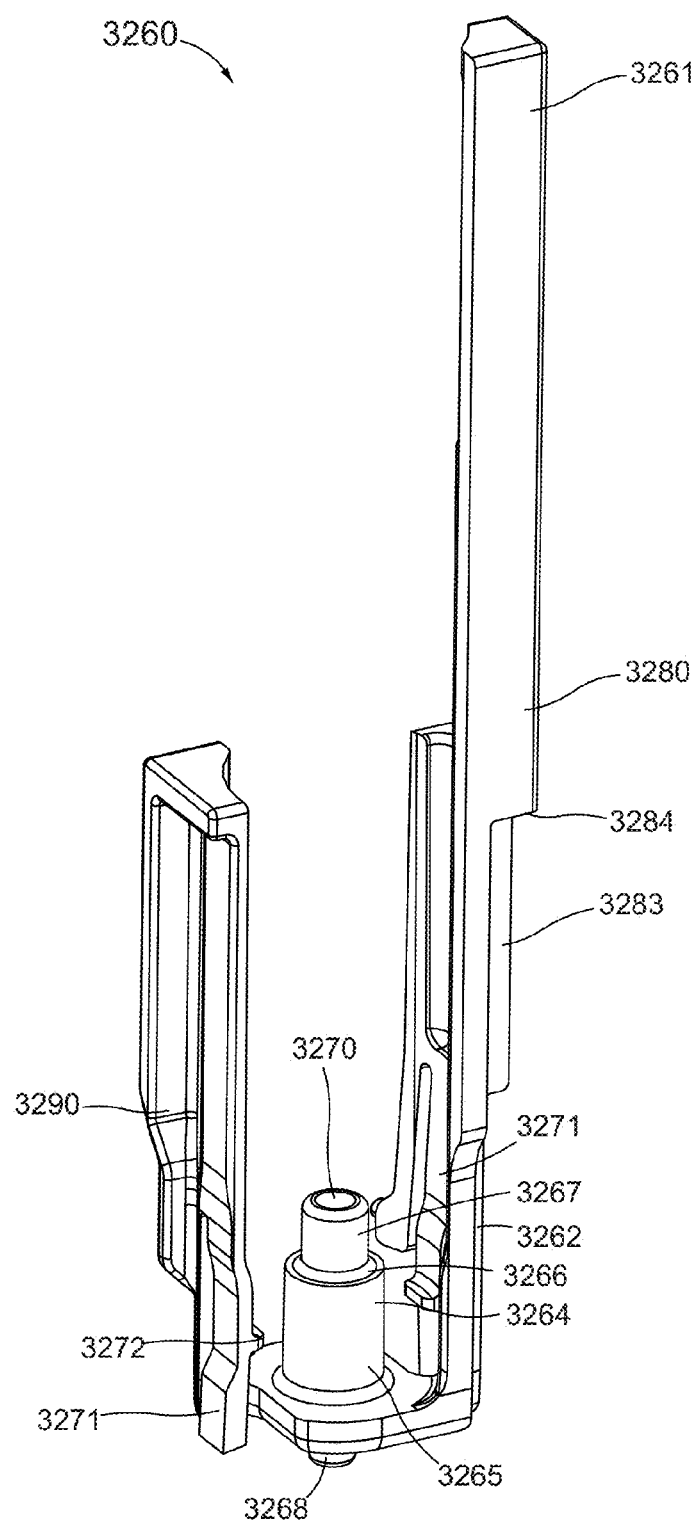
FIG. 13 is a perspective view of a carrier included in the medical injector of FIG. 9.

FIGS. 11-13 are various views of portions of the medicament container assembly 3200. The medicament container assembly 3200 includes a medicament container 3210, the needle 3216, and the carrier 3260. The medicament container 3210 includes a proximal end portion 3212, a distal end portion 3213, and a bypass 3220. The bypass 3220 can be a singular channel bypass or can define multiple channels. Although the bypass 3220 is shown in FIGS. 11 and 12 as an external bypass, in other embodiments, the bypass 3220 can be internal to the medicament container and/or a part of an elastomeric member. Said another way, in some embodiments the bypass can be configured such that the outer diameter of the medicament container 3210 is substantially constant. The bypass 3220 is configured to facilitate the venting, mixing and/or injection of a medicament contained within the medicament container 3210, as described in further detail herein. In particular, the bypass 3220 is configured to place various volumes within the medicament container 3210 in fluid communication with each other.

As shown in FIGS. 11 and 12, the distal end portion 3213 of the medicament container 3210 is configured to engage at least a portion of the carrier 3260 and the needle 3216, as described below. The distal end portion 3213 of the medicament container 3210 receives a stopper 3254. More specifically, the stopper 3254 includes a proximal end portion 3255 and a distal end portion 3256. The proximal end portion 3254 is configured to be disposed within the medicament container 3210 to define a substantially fluid tight and/or hermetic seal. Furthermore, the distal end portion 3256 of the stopper 3254 includes a flange (or second retention portion) 3257 that engages a distal surface of the medicament container 3210. As shown in FIG. 12, the stopper 3254 further includes a set of inner walls (including a first retention portion) 3258 defining an inner volume 3259. The inner volume 3259 is configured to receive a proximal end portion 3217 of the needle 3216 and a portion of the carrier 3260. As described in further detail herein, a first retention portion 3267 of the carrier 3260 can engage the first retention portion of the inner walls 3258 such that the first retention portion 3267 of the carrier 3260 and the first retention portion of the inner walls 3258 define a substantially fluid tight seal and/or hermetic seal. In this manner, the first retention portion 3267 of the carrier 3260 can be disposed within the inner volume 3259 during a manufacturing and/or fill process such that the first retention portion of the carrier 3260 and the first retention portion of the inner walls 3258 form the substantially fluid tight seal, thereby maintaining the sterility of the proximal end portion 3217 of the needle 3216.

The proximal end portion 3212 of the medicament container 3210 receives a first elastomeric member 3221, a second elastomeric member 3225, and a third elastomeric member 3229. In some embodiments, the first elastomeric member 3221, the second elastomeric member 3225, and the third elastomeric member 3229 are placed within the medicament container 3210 during the fill process, as further described herein, to define a diluent volume 3236, a dry medicament volume 3237, and a void volume 3238 (see, e.g., FIG. 12). Said another way, the diluent volume 3236 is a volume disposed within the medicament container 3210 defined between a distal surface 3223 of the first elastomeric member 3221 and a proximal surface 3226 of the second elastomeric member 3225. The dry medicament volume 3237 is a volume disposed within medicament container 3210 defined between a distal surface 3227 of second elastomeric member 3225 and a proximal surface 3230 of third elastomeric member 3229 and the void volume 3238 is a volume disposed within the medicament container 3210 defined between a distal surface 3231 of the third elastomeric member 3229 and the distal end portion 3213 of the medicament container 3210.

As shown in FIG. 12, the diluent volume 3236, the dry medicament volume 3237, and the void volume 3238 are defined by the positions of the first elastomeric member 3221, the second elastomeric member 3225, and the third elastomeric member 3229, relative to and/or within the medicament container 3210. In some embodiments, the diluent volume 3236 can contain a medicament diluent, such as, for example, water. In some embodiments, the dry medicament volume 3237 can contain a lyophilized medicament (e.g., any suitable medicament produced via any suitable lyophilizing process) including any of the formulations and/or compositions described herein.

As shown in FIG. 10, the proximal end portion 3212 of the medicament container 3210 is coupled to and/or receives a portion of the medicament delivery mechanism 3300 such that medicament delivery mechanism 3300 can move the first elastomeric member 3221, the second elastomeric member 3225, and/or the third elastomeric member 3229 to vent, mix and/or inject the medicament disposed therein. More specifically, the proximal end portion 3212 of the medicament container 3210 can receive a piston portion 3330 of a first movable member 3301 and a second movable member 3370 (also referred to herein as a "mixing piston 3370").

The medicament container 3210 can have any suitable size (e.g., length and/or diameter). Moreover, the medicament container 3210, the piston portion 3330, and/or the mixing piston 3370 can be collectively configured such that the piston portion 3330 and/or the mixing piston 3370 travels a desired distance within the medicament container 3210 (i.e., the "stroke") during an injection event. In this manner, the medicament container 3210, the diluent contained within the diluent volume 3236, the lyophilized medicament contained within the dry medicament volume 3237, the void volume 3238, the piston portion 3330, and the mixing piston 3370 can be collectively configured to provide a desired fill volume and delivery volume.

The length of the medicament container 3210 and the length of the piston portion 3330 and/or the mixing piston 3370 can be configured such that the medicament delivery mechanism 3300 can fit in the same housing 3100 regardless of the fill volume, the delivery volume and/or the ratio of the fill volume to the delivery volume. In this manner, the same housing and production tooling can be used to produce devices having various dosages of the medicament. For example, in a first embodiment (e.g., having a fill volume to delivery volume ratio of 0.4), the medicament container has a first length and the second movable member has a first length. In a second embodiment (e.g., having a fill volume to delivery volume ratio of 0.6), the medicament container has a second length shorter than the first length, and the second movable member has a second length longer than the first length. In this manner, the stroke of the device of the second embodiment is longer than that of the device of the first embodiment, thereby allowing a greater dosage. The medicament container of the device of the second embodiment, however, is shorter than the medicament container of the device of the first embodiment, thereby allowing the components of both embodiments to be disposed within the same housing and/or a housing having the same length.

The first elastomeric member 3221, the second elastomeric member 3225, and the third elastomeric member 3229 can be of any design or formulation suitable for contact with the medicament (e.g., the diluent contained in the diluent volume 3236 and/or a lyophilized medicament contained in the dry medicament volume 3237). For example, the elastomeric members 3221, 3225, and 3229 can be formulated to minimize any reduction in the efficacy of the medicament that may result from contact (either direct or indirect) between the elastomeric members 3221, 3225, and 3229 and the medicament. For example, in some embodiments, the first elastomeric member 3221, the second elastomeric member 3225, and the third elastomeric member 3229 can be formulated to minimize any leaching or out-gassing of compositions that may have an undesired effect on the medicament. In other embodiments, the elastomeric members 3221, 3225, and 3229 can be formulated to maintain its chemical stability, flexibility and/or sealing properties when in contact (either direct or indirect) with the medicament over a long period of time (e.g., for up to six months, one year, two years, five years or longer). In some embodiments, the first elastomeric member 3221, the second elastomeric member 3225, and the third elastomeric member 3229 are substantially similar to the first elastomeric member, the second elastomeric member, and the third elastomeric member, respectively, described in the '936 application In some embodiments a first elastomeric member, a second elastomeric member, and/or a third elastomeric member of an injector can be similar to first elastomeric member 3221 or third elastomeric member 3229. Said another way, in some embodiments, a medicament container can include three elastomeric members similar to the first elastomeric member 3221. In other embodiments, a medicament container can include three elastomeric members similar to the third elastomeric member 3229. For example, in such embodiments, the first elastomeric member and the second elastomeric member can define a proximal counter bore and a distal counter bore and can further control the fill volume and/or delivery volume of a diluent and/or lyophilized medicament disposed within the medicament container.

As described above, the medicament container 3210 is configured to engage and/or be coupled to the carrier 3260. Referring to FIG. 13, the carrier 3260 includes a proximal end portion 3261, a distal end portion 3262, a needle hub 3264, a first retention arm 3280, and a second retention arm 3290. The first retention arm 3280 and the second retention arm 3290 extend, in the proximal direction, from a container-mounting portion 3263 disposed at the distal end portion 3262 of the carrier 3260. The container-mounting portion 3263 is configured to selectively engage the distal end portion 3213 of the medicament container 3210 and/or the flange (or second retention portion) 3257 of the stopper 3254. More specifically, the carrier 3260 includes a set of tabs 3271 that include a container shoulder 3272 (also referred to as the second retention portion of the carrier). The set of tabs 3271 are configured to selectively engage a portion of the housing 3100 as the medicament container assembly 3200 is moved in the proximal direction during an injection event. The arrangement of the tabs 3271, the housing 3100, and the container shoulders (or second retention portion of the carrier) 3272 are such that the flange (or second retention portion) 3257 of the stopper 3254 can selectively engage the container shoulder 3272 when moving between the first container position and the second container position, as described in further detail herein The needle hub 3264 includes a base portion 3265, an upper portion 3267, and a lower needle port 3268. The base portion 3265 includes a proximal surface 3266 from which the upper portion (or first retention portion) 3267 extends in the proximal direction. The lower needle port 3268 is configured to extend from the base portion 3265 in the distal direction. The needle hub 3264 defines a needle passageway that receives a proximal end portion 3217 of the needle 3216. Expanding further, the needle passageway can include an inner surface (not shown) that includes any suitable feature to couple the needle 3216 within the needle hub 3264. For example, in some embodiments, the inner surface defining the needle passageway can include a set of protrusions configured to define a friction fit with the needle 3216. In other embodiments, an adhesive can be applied to the inner surface defining the needle passageway to couple the needle 3216 to the needle hub 3264. The needle hub 3264 is configured to selectively engage a portion of the stopper 3254 when the stopper 3254 is disposed within the medicament container 3210. More specifically, when the medicament container assembly 3200 is in the proximal position relative to the housing 3100, the upper (or first retention) portion 3267 of the needle hub 3264 is disposed within the inner volume 3259 of the stopper 3254 such that the first retention portion of the inner walls 3258 engages the upper (or first retention) portion 3267 and/or the proximal surface 3266 of the base portion 3265. As described in further detail herein, during a portion of an injection event the medicament container 3210 can move relative to the carrier 3260 such that the base portion 3265 is disposed within the inner volume 3259 of the stopper 3254.

The first retention arm 3280 defines a channel 3283 and includes a retraction spring surface 3284. The channel 3283 receives a retraction spring 3440 such that a proximal end portion of the retraction spring 3440 is in contact with the retraction spring surface 3284. In this manner, the retraction spring 3440 can exert a retraction force on the retraction spring surface 3284 to facilitate a retraction event, as described in further detail herein. Similar to the first retention arm 3280, the second retention arm 3290 engages the medicament container 3210 when the medicament container 3210 is disposed within and/or is coupled to the container-mounting portion 3263. In this manner, the container-mounting portion 3263, the first retention arm 3280, and the second retention arm 3290 act to couple the medicament container 3210 to the carrier 3260.

As shown in FIGS. 10 and 14-19, the system actuator assembly 3500 includes the base 3510, the release member 3530, and a mixing actuator assembly 3540. The release member 3530 is configured to engage a latch portion 3310 of the medicament delivery mechanism 3300 when the medical injector 3000 is in its first (or storage) configuration (FIG. 10). In this manner, the release member 3530 maintains the latch portion 3310 in contact with a portion of the housing 3100. When the portion of the housing 3100 is in contact with the latch portion 3310, the portion of the housing 3100 applies a reaction force to the latch portion 3310 in response to the force applied by a spring 3420 configured to urge the transfer member 3600 and the medicament delivery mechanism 3300 in a distal direction. Similarly stated, when the latch portion 3310 is in contact with the housing 3100, the housing 3100 limits distal movement of the latch portion 3310, and thus, the medicament delivery mechanism 3300. In this manner, when the base 3510 is in a first position (i.e., before actuation of the medical injector 3000), the release member 3530 maintains the latch portion 3310 in contact with the housing 3100 and maintains the medical injector 3000 in the first configuration. Furthermore, as shown in FIG. 10, when the medical injector 3000 is in the first configuration, at least a portion of the safety lock 3700 is disposed within a portion of the base 3510 such that the portion of the safety lock 3700 prevents the movement of the base 3510 in the proximal direction relative to the housing 3100.

The mixing actuator assembly 3540 includes the mixing actuator member 3550 and the safety lock 3700. As shown in FIG. 10, the safety lock 3700 includes the safety lock actuator 3724. The safety lock actuator 3724 is configured to selectively engage the mixing actuator member 3550. In this manner, when the safety lock 3700 is moved in the distal direction to be removed from the medical injector 3000, the safety lock actuator 3724 contacts the mixing actuator member 3550 such that the removal of the safety lock 3700 moves a portion of the mixing release member 3550 in the distal direction, as described in further detail herein.

The mixing actuator member 3550 includes a retention portion 3558 movably disposed within a portion of the first movable member 3301. The retention portion 3558 is configured to move within the portion of the first movable member 3301 between a first position (e.g., the locked position) and a second position (e.g., the mixing position). The mixing piston 3370 is disposed within the piston portion 3330 of the first movable member 3301 such that a portion of the mixing piston 3370 selectively engages the retention portion 3558 of the mixing actuator 3550. In this manner, when the mixing actuator 3550 is in the first position, the mixing piston 3370 is maintained in the first configuration. Furthermore, when the safety lock 3700 is moved in the distal direction (e.g., removed from the medical injector 3000), the retention portion 3558 is moved to the second position such that the mixing piston 3370 is actuated to urge a venting, air purging and/or mixing event, as described in further detail herein.

The medicament delivery mechanism 3300 (all or portions of which can also be referred to as a "movable assembly") includes the first movable member 3301, the second movable member 3370 (the mixing piston 3370), and a mixing spring 3390. The arrangement of the first movable member 3301, the second movable member 3370, and the mixing spring 3390 is such that the mixing spring 3390 can be actuated to move the second movable member 3370 relative to the first movable member 3301 to urge a venting and/or mixing event.

The first movable member 3310 includes a latch portion 3310 and a piston portion 3330. The latch portion 3310 of the first movable member 3301 extends in the distal direction and is configured to selectively engage a portion of the housing 3100 and the release member 3530. The latch portion 3310 is further configured to engage a latch 3620 of the transfer member 3600. More particularly, when the medical injector 3000 is in the first configuration (i.e., prior to actuation), the latch portion 3310 of the first movable member 3301 is in contact with the latch 3620 of the transfer member 3600. In this manner, the transfer member 3600 can transfer a force produced by the spring 3420 to the latch portion 3310 of the first movable member 3300 to move the medicament delivery mechanism 3300 in the distal direction when the medical injector 3000 is actuated. Similarly stated, this arrangement allows the medicament delivery mechanism 3300 and/or the first movable member 3301 to move with and/or remain coupled to the transfer member 3600 during the insertion and/or injection operation.

The piston portion 3330 is configured to receive at least a portion of the mixing spring 3390 and the mixing piston 3370. More specifically, the medicament delivery mechanism 3300 is configured such that when the medical injector 3000 is in the first configuration (e.g., the storage configuration), the mixing spring 3390 is disposed within the piston portion 3330 and the mixing piston 3370 in a first (e.g., compressed) configuration (see e.g., FIG. 10). The arrangement of the first movable member 3301, the mixing piston 3370, and the mixing actuator member 3550 is such that when the mixing actuator member 3550 is moved to actuate a venting and/or mixing event, the mixing spring 3390 expands to move the mixing piston 3370 in the distal direction. Thus, the expansion of the mixing spring 3390 is such that the mixing spring 3390 exerts a force on the mixing piston 3370 to move the mixing piston 3370 in the distal direction, as further described herein.

The transfer member 3600 includes the latch and can receive and/or engage a portion of the spring 3420. The latch 3620 is configured to engage the latch portion 3310 of the first movable member 3301. In this manner, the transfer member 3600 transfers a force from the actuation of the spring 3420 to the first movable member 3301 and/or the medicament delivery mechanism 3300 to move the medicament delivery mechanism 3300 in the distal direction within the housing 3100. In this manner, the force produced by the spring 3420, which is offset from the medicament delivery mechanism 3300 and/or the medicament container 3210, results in both the insertion of the needle 3216 and injection of the medicament within the medicament container 3210. Although, as described below, the mixing spring 3390 produces a force to vent and/or mix a diluent and a lyophilized medicament, in other embodiments, a portion of the force produced by the spring 3420 can be used to facilitate the mixing process.

Figure 19:
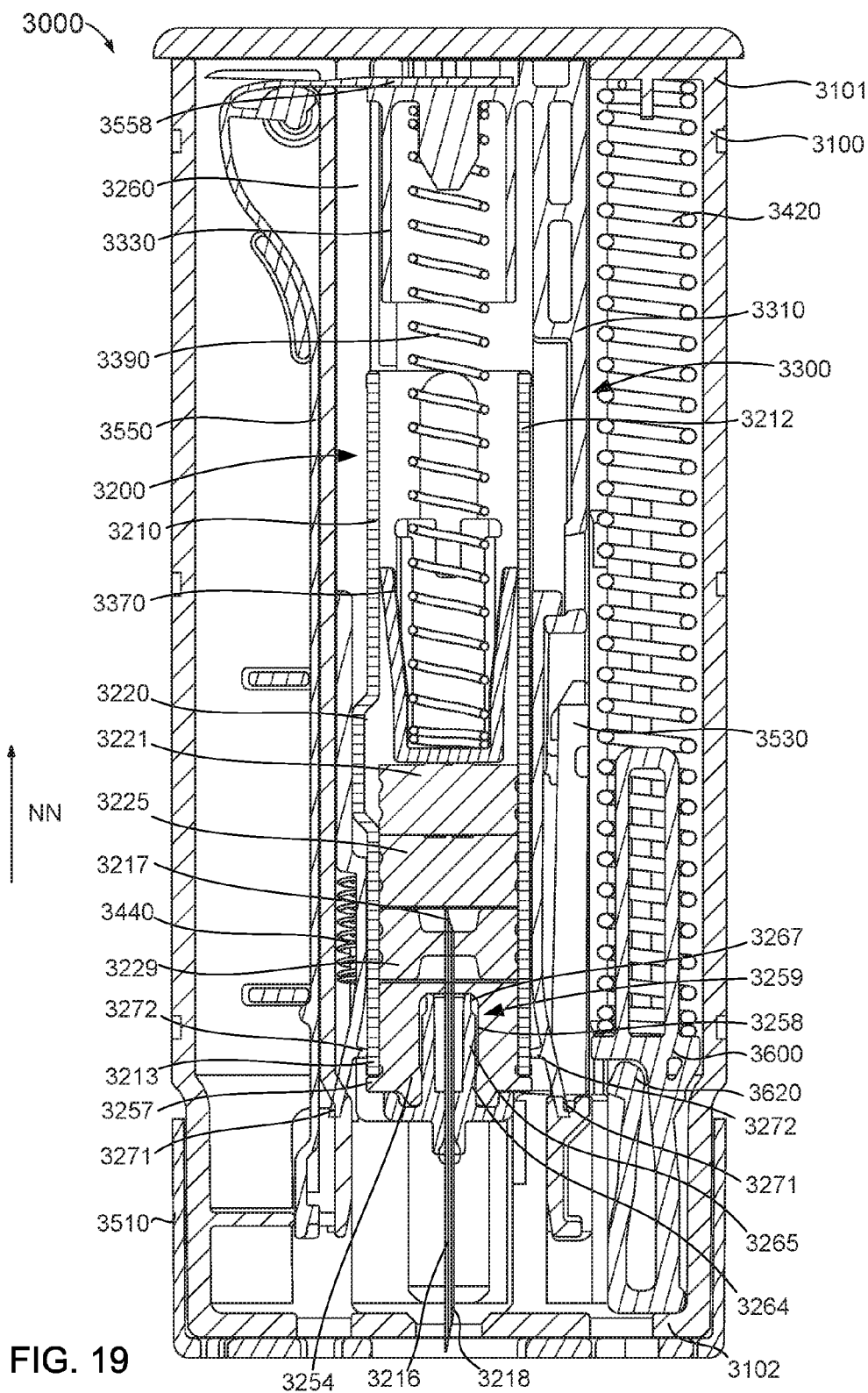

Furthermore, when the transfer member 3600 has moved a desired distance in the distal direction in response to the force produced by the actuation of the spring 3420 (e.g., upon completion of the medicament injection), the transfer member 3600 can be moved to a second configuration (see e.g., FIG. 19). In this manner, the latch 3620 can be disengaged from the latch portion 3310. Similarly stated, when the transfer member 3600 is in its second configuration, the latch 3620 is disengaged from the first movable member 3301, and the force produced by the spring 3420 is no longer transferred to the medicament delivery mechanism 3300. Said yet another way, when the transfer member 3600 is in its second configuration, the medicament delivery mechanism 3300 is isolated and/or no longer operably coupled to the spring 3420. In this manner, as described below, the retraction force exerted by the retraction spring 3440 moves the medicament delivery mechanism 3300 and/or the medicament container assembly 3200 proximally within the housing 3100 to retract the needle 3216 (FIG. 19).

As described above, the safety lock 3700 can be configured to selectively engage a portion of the housing 3100 to maintain the medical injector 3000 in the first configuration. Furthermore, the safety lock can be coupled to a needle sheath 3820 configured to be disposed about a portion of the needle 3216. When the medical injector 3000 is in the first configuration, the needle sheath 3820 can further be configured to receive the lower needle port 3268 of the carrier 3260 such that the lower needle port 3268 and the needle sheath 3820 define a substantially fluid tight and/or hermetic seal. Thus, the arrangement of the needle sheath 3820 and the lower needle port 3268 can maintain the sterility of the needle 3216 prior to actuation of the medical injector 3000 (e.g., during storage).

Figure 14:
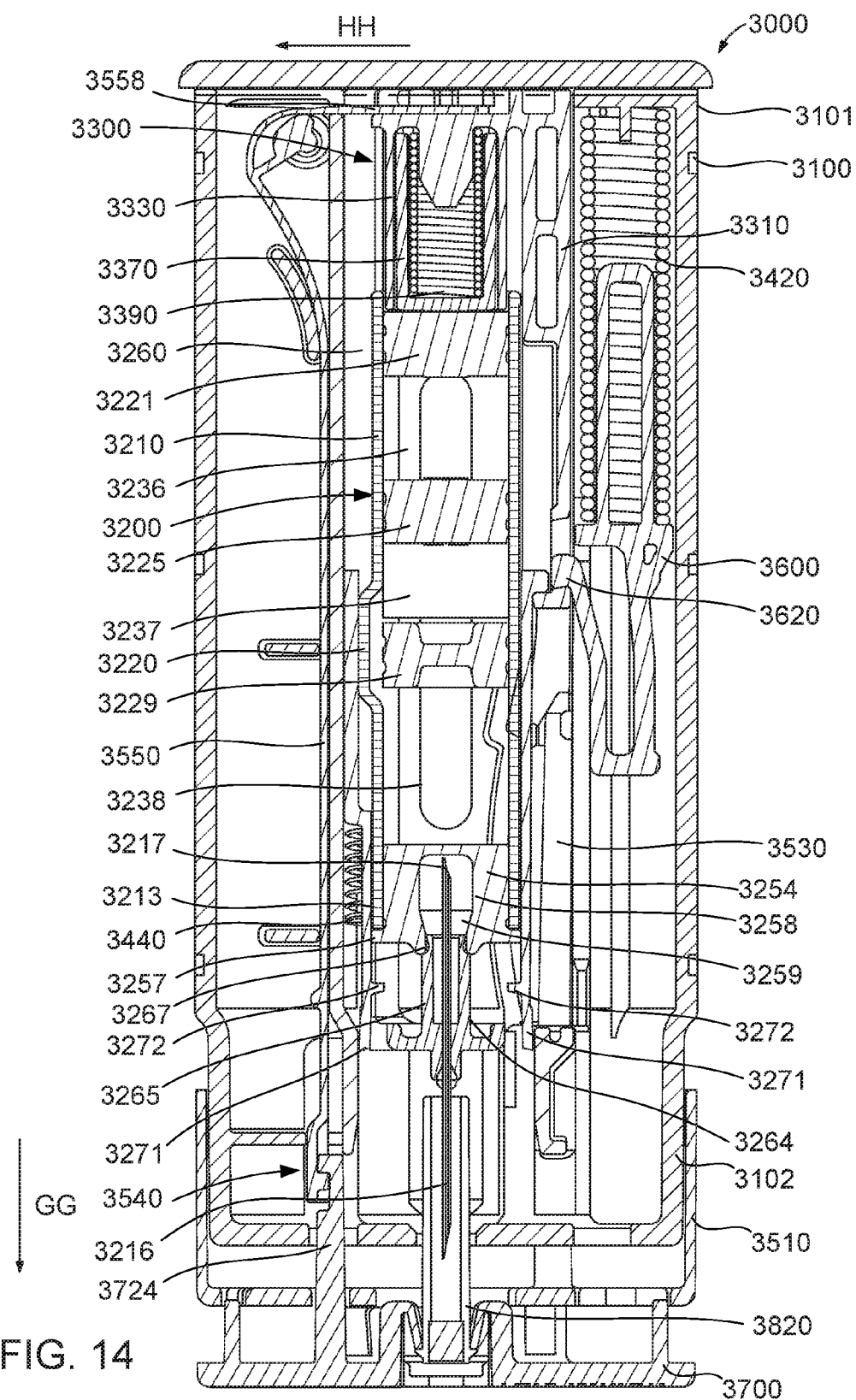
FIGS. 14 and 15 are cross-section views of the medical injector taken along the line $X_1$-$X_1$ in FIG. 9, being moved from a first configuration to a second configuration.

As shown in FIG. 14, the medical injector 3000 is first enabled by moving the medicament delivery device 3000 from the first configuration to the second configuration by removing the cover 3190 and moving the safety lock 3700 in the direction shown by the arrow GG. When the safety lock 3700 is moved from the first position to the second position, the safety lock 3700 is no longer in contact with the distal end portion 3103 of the housing 3100, thereby enabling the medicament delivery mechanism 3300. Additionally, when the safety lock 3700 is removed from and/or moved relative to the housing 3100, the actuator 3724 of the safety lock 3700 also moves in the direction GG to actuate the mixing actuator member 3550. More specifically, when the actuator 3724 is moved in the direction GG, a portion of the mixing actuator member 3550 pivots relative to the housing 3100 such that the retention portion 3558 moves in the direction of the arrow HH.

Figure 15:
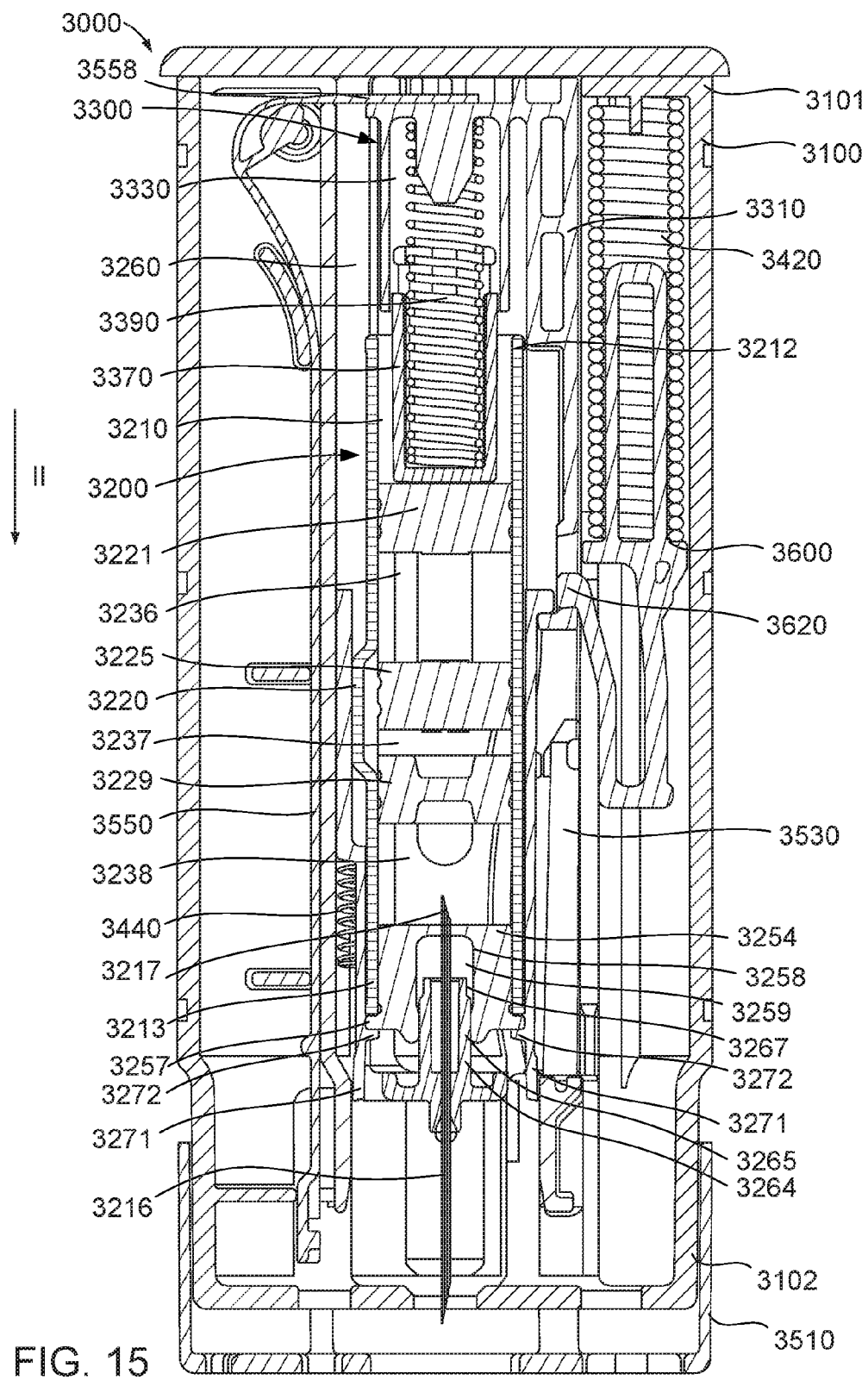

As shown in FIG. 15, the lateral motion of the retention portion 3558 is such that the retention portion 3558 disengages the mixing piston 3370. In this manner, the retention portion 3558 no longer maintains the mixing spring 3390 in the first configuration (e.g., the compressed configuration). Therefore, when the retention portion 3558 moves laterally, the mixing spring 3390 expands to the second configuration and exerts a force to move the mixing piston 3370 in the distal direction, as indicated by arrow II in FIG. 15.

With the mixing spring 3390 in the second configuration (e.g., the expanded configuration), much of the mixing piston 3370 is disposed outside the piston portion 3330 of the first movable member 3301. Similarly stated, the mixing piston 3370 is disposed in a distal position relative to the piston portion 3330 of the first movable member 3301.

Figure 16:
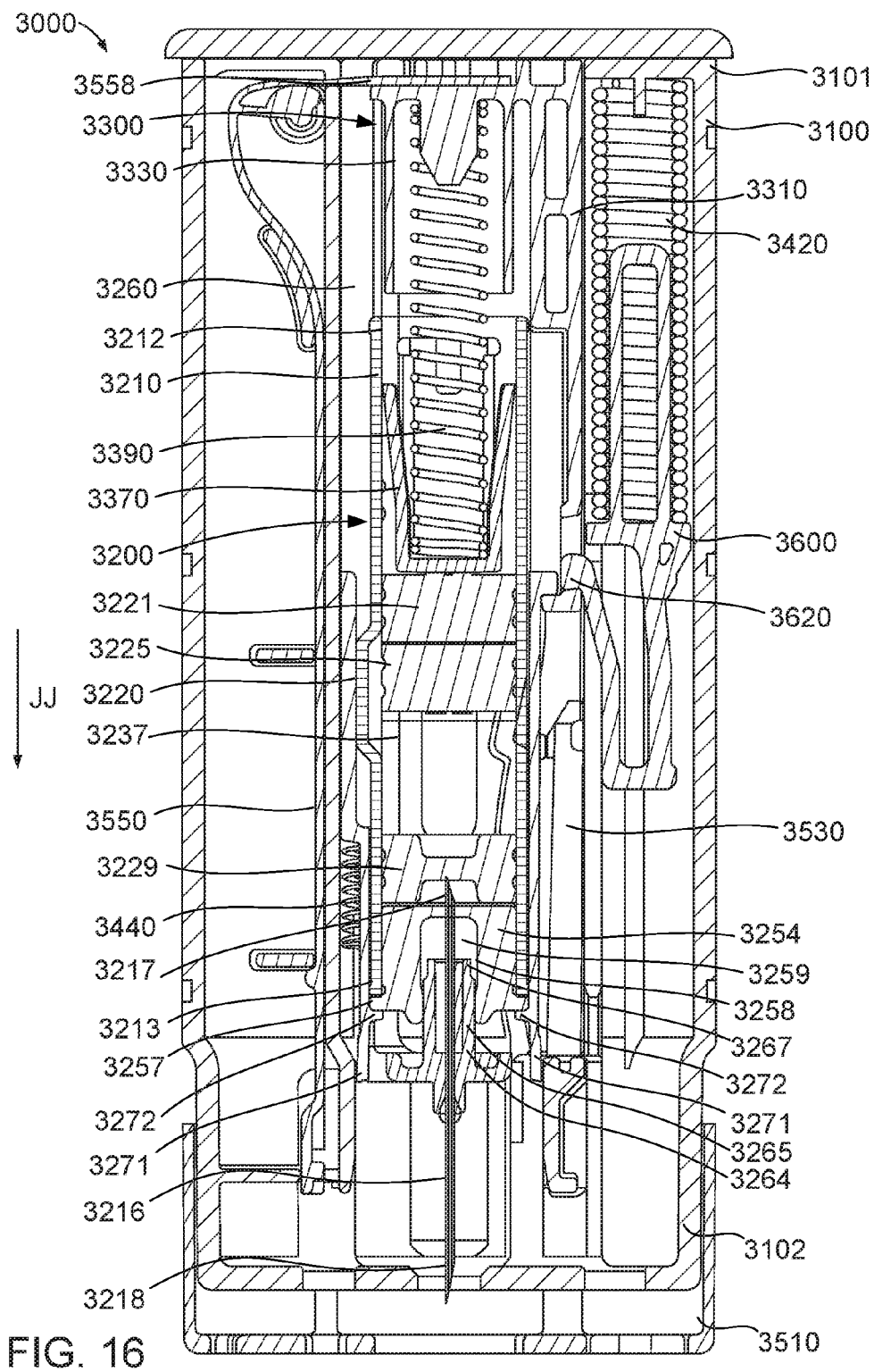
FIGS. 16-19 are cross-sectional views of the medical injector taken along the line $X_1$-$X_1$ in FIG. 9, in a third, fourth, fifth, and sixth configuration, respectively.

The distal movement of the mixing piston 3370 begins the venting and mixing event, as shown in FIGS. 15 and 16. More specifically, the mixing piston 3370 engages the first elastomeric member 3221 and transfers a portion of the force exerted by the mixing spring 3390 to move at least the first elastomeric member 3221 in the distal direction. The arrangement of the elastomeric members within the medicament container 3210 is such that the portion of the force exerted on the first elastomeric member 3221 moves the medicament container 3210 in the distal direction relative to the carrier 3260. Expanding further, the medicament container 3210 is disposed within the carrier 3260 such that the upper (or first retention) portion 3267 of the needle hub 3264 is disposed within the inner volume 3269 of the stopper 3254. This arrangement is such that without the application of an external force (e.g., the force exerted by the mixing spring 3390), the medicament container 3210 remains in a fixed position relative to the carrier 3260. Moreover, the elastomeric members are disposed within the medicament container 3210 such that the friction force between the elastomeric members and the walls of the medicament container 3210 is greater than the external force to move the medicament container 3210 relative to the carrier 3260. Thus, when the mixing spring 3390 is actuated to apply the mixing force to the first elastomeric member 3221, the medicament container 3210 moves in the direction of the arrow II shown in FIG. 15, relative to the carrier 3260. Therefore, the base portion 3265 of the needle hub 3264 is disposed within the inner volume 3259 of the stopper 3254 and the proximal end portion 3217 of the needle 3216 pierces the proximal end portion 3255 of the stopper 3254 such that the proximal end portion 3217 of the needle 3216 is disposed within the void volume 3238. Furthermore, the flange (or second retention portion) 3257 of the stopper 3254 is placed in contact with the protrusions (or second retention portion) 3272 of the carrier 3260. In this manner, the protrusions (or second retention portion) 3272 temporarily prevent further distal movement of the medicament container 3210 relative to the carrier 3260

Concurrently with the initial movement of the medicament container 3210, a portion of the mixing force moves the first elastomeric member 3221, the second elastomeric member 3225, and the third elastomeric member 3229 in the direction of the arrow II. The movement of the second elastomeric member 3225 compresses the lyophilized medicament disposed within the dry volume 3237 (i.e., the volume of the lyophilized medicament volume 3237 is reduced). Moreover, because the third elastomeric member 3229 is initially positioned aligned with the bypass 3220, trapped air that is released during the compression of the lyophilized medicament is conveyed into the void volume 3238 via the bypass 3220. More particularly, the lyophilized medicament can be formulated to include air (e.g., as much as 50% air by volume, as much as 60% air by volume, as much as 70% air by volume, as much as 80% air by volume, as much as 90% air by volume, approximately 93% air by volume). As shown in FIG. 14, with the dry volume 3237 in fluid communication with the bypass 3220, the air portion of the lyophilized medicament can flow through the bypass 3220 and into the void volume 3238. Thus, as shown in FIG. 15, the volume of the lyophilized medicament is reduced and the third plunger is moved beyond the bypass 3220. In addition, because the proximal end portion 3217 of the needle 3216 is in fluid communication with the void volume 3238, the air portion of the lyophilized medicament can be vented through the needle 3216 prior to the insertion of the needle 3216 into the patient. This arrangement allows for purging and/or venting in response to a force produced by an energy storage member, wherein such venting and/or purging is not dependent on the orientation of the device.

As shown in FIG. 16, further distal movement of the mixing piston 3370 places the medical injector 3000 into a third configuration. Similarly stated, the mixing piston 3370 moves in the direction of the arrow JJ to place the diluent volume 3236 in fluid communication with the dry medicament volume 3237 via the bypass 3220 such that the diluent within the diluent volume 3236 is transferred to the dry medicament volume 3237. More specifically, the mixing piston 3370 continues to move the first elastomeric member 3221, the second elastomeric member 3225, and the third elastomeric member 3229 in the distal direction such that the third elastomeric member 3229 is placed in contact with the stopper 3254 and the diluents volume 3236 and the dry medicament volume 3237 are placed in fluid communication. Thus, the diluent can mix with the lyophilized medicament disposed within the dry medicament volume 3237 to reconstitute the medicament for injection. In this manner, the first elastomeric member 3221 is moved into contact with the second elastomeric member 3225 such that substantially all the diluent within the diluents volume 3236 are mixed with the lyophilized medicament.

In some embodiments, the mixing force, the geometry of the bypass 3220 and/or the elastomeric members can be collectively configured to produce a turbulent flow of the diluent within the dry medicament volume 3237. For example, in some embodiments, the mixing spring 3390 can be configured to have a variable spring rate such that the force exerted by the first elastomeric member 3221 is maintained during the expansion of the spring 3390, thus resulting in a high velocity of the diluent through the bypass 3220. In some embodiments, the portion the medicament container 3200 that defines the bypass 3220 can include a helical structure to impart a swirling motion to the diluent.

After the mixing event, the medical injector 3000 can be moved from the third configuration (FIG. 16) to a fourth configuration (FIG. 17) by moving the base 3510 from a first position to a second position. Similarly stated, the medical injector 3000 can be actuated by the system actuator assembly 3500 by moving the base 3510 proximally relative to the housing 3100. The base 3510 is moved from its first position to its second position by placing the medical injector 3000 against the body of the patient and moving the base 3510 with respect to the housing 3100 in the direction shown by the arrow KK in FIG. 17.

When the base 3510 is moved from the first position to the second position, the system actuator assembly 3500 actuates the medicament delivery mechanism 3300, thereby placing the medical injector 3000 in its fourth configuration (i.e., the needle insertion configuration). More specifically, the proximal movement of the system actuator assembly 3500 and/or the base 3510 moves the release member 3530 in the proximal direction within the housing 3100, thereby allowing the latch portion 3310 to be disengaged from the release member 3530. Thus, the spring 3420 is allowed to expand in the direction shown by the arrow LL in FIG. 17. In this manner, the latch 3620 of the transfer member 3600 transfers at least a portion of the force to the latch portion 3310 of the first movable member 3301 such that the portion of the force moves the medicament delivery mechanism 3300 in the distal direction, shown by the arrow LL. Thus, the first movable member 3301 and the transfer member 3600 move together distally within the housing 3100.

Figure 17:
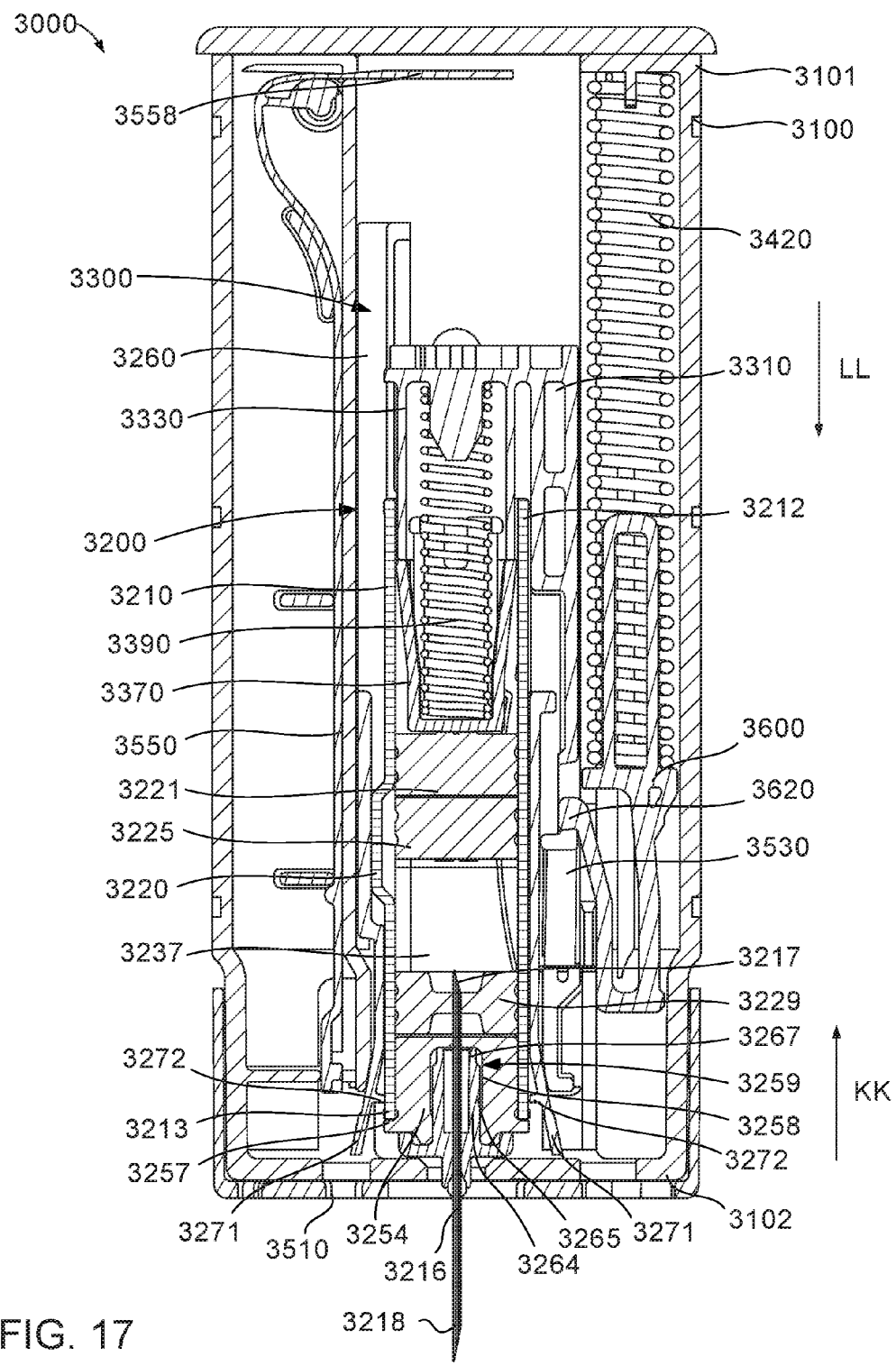
Figure 18:
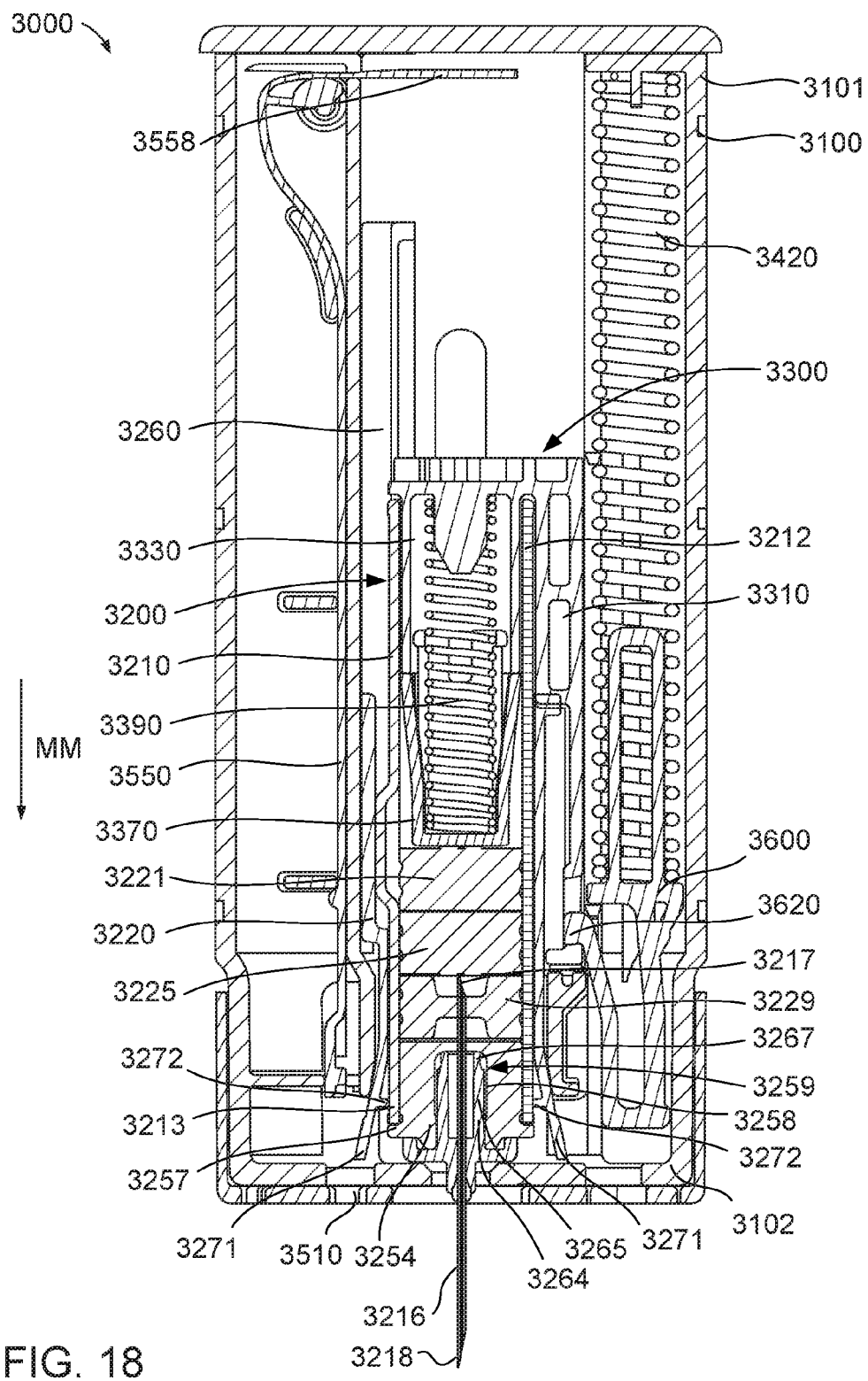

When the medicament delivery mechanism 3300 is moving distally, the piston portion 3330 of the first movable member 3301 applies a portion of the force to the medicament container 3210. More specifically, the portion of the force exerted by the piston portion 3330 and/or the mixing piston 3370 moves the medicament container assembly 3200 in the distal direction. As shown in FIG. 17, when the medicament container assembly 3200 is in the first position (e.g., prior to being moved by the portion of the insertion force), the protrusions 3272 of the needle insertion tabs 3271 included in the carrier 3260 are in contact with the flange 3257 of the stopper 3254. Therefore, when the portion of the insertion force is exerted on the first elastomeric member 3221, the force is transferred through the medicament container 3210 to the protrusions 3272 to move the carrier 3260 in the distal direction.

As shown in FIG. 17, the carrier 3260 moves to a second position within the housing 3100 during the needle insertion operation. With the carrier 3260 in the second position, the tabs 3271 of the carrier 3260 contact the housing 3100, thereby limiting the distal movement of the carrier 3260. Furthermore, the tabs 3271 are configured to disengage from a portion of the housing 3100 such that the tabs 3271 expand outwardly. In the expanded configuration, the tabs 3271 extend such that the flange 3254 is no longer in contact with the protrusions 3272. Thus, the portion of the insertion force applied to the first elastomeric member 3221 moves the medicament container 3210 in the distal direction, relative to the carrier 3260. In this manner, the proximal end portion 3217 of the needle 3216 punctures through the thickness of the third elastomeric member 3229 and the medical injector 3000 can be placed in a fifth configuration (i.e., the medicament delivery configuration).

The medical injector 3000 is placed in the fifth configuration when the proximal end portion 3217 of the needle 3216 is disposed within the mixing volume 3237 (e.g., the dry medicament volume 3237) and a portion of the insertion force is exerted on the first elastomeric member 3221. With the medicament container 3210 and the carrier 3260 in the second position within the housing 3100 (e.g., moved in the distal direction), the portion of the force exerted on the first elastomeric member 3221 can move the first elastomeric member 3221 and the second elastomeric member 3225 from the second position to a third position within the medicament container 3210. More specifically, the mixing piston 3370 and/or piston portion 3330 exerts the portion of the force on the first elastomeric member 3221 as indicated by arrow MM in FIG. 18 to move the first elastomeric member 3221 and the second elastomeric member 3225 to the third position. In this manner, the medicament disposed within the dry medicament volume 3237 is transferred to the needle 3216 and injected into the body of the patient.

When the spring 3420 fully expands, the medicament delivery mechanism 3300 moves in the distal direction to fully inject the medicament within the medicament container 3210. Additionally, when the spring 3420 is fully expanded and/or when the medicament delivery mechanism 3300 has moved a desired distance within the housing 3100, the transfer member 3600 can be placed in the second configuration. In this manner, the latch 3620 can be disengaged from the latch portion 3310. Similarly stated, the spring 3420 and/or the transfer member 3600 are decoupled from the medicament delivery mechanism 3300. With the latch 3620 disengaged from the latch portion 3310, the medical injector 3000 can be moved from the fifth configuration to the sixth configuration (i.e., the retraction configuration).

With the transfer member 3600 disengaged from the medicament delivery mechanism 3300, the medicament container assembly 3200 and the medicament delivery mechanism 3300 are configured to move within the housing 3100 in the direction shown by the arrow NN in FIG. 19 in response to a force exerted by the retraction member 3440 (e.g., the retraction spring). Similarly stated, with the medicament delivery mechanism 3300 disengaged from the transfer member 3600 and/or the spring 3420, the insertion force is no longer applied to the medicament delivery mechanism 3300. In this manner, the retraction member 3440 is configured to expand in the direction of the arrow NN to apply a retraction force to the medicament container assembly 3200. Similarly stated, with the portion of the force insertion configured to compress the retraction spring 3440 removed, the retraction member 3440 expands, returning to its uncompressed (i.e., non-deformed) configuration.

During the retraction operation, the retraction spring 3440 exerts a retraction force on the retraction spring surface 3284 to move the carrier 3260 in the direction NN. With the medicament container 3210 coupled to the carrier 3260 a portion of the retraction force moves the medicament container 3210 in the proximal direction. This motion, removes the needle 3216 from the target location of the patient and retracts the needle into the housing 3100, as shown in FIG. 19.

While specific components are discussed above with respect to the medical injector 3000, in other embodiments, any of the medicament delivery devices and/or medical injectors described herein can include components that are modified and/or removed from those shown and described above with respect to the medical injector 3000. Similarly stated, in other embodiments, a medical injector can include different, more or fewer components than are shown in the medical injector 3000 without substantially changing the venting, mixing and/or medicament injection event. For example, FIGS. 20-27 show a medical injector 4000, according to an embodiment.

Figure 20:
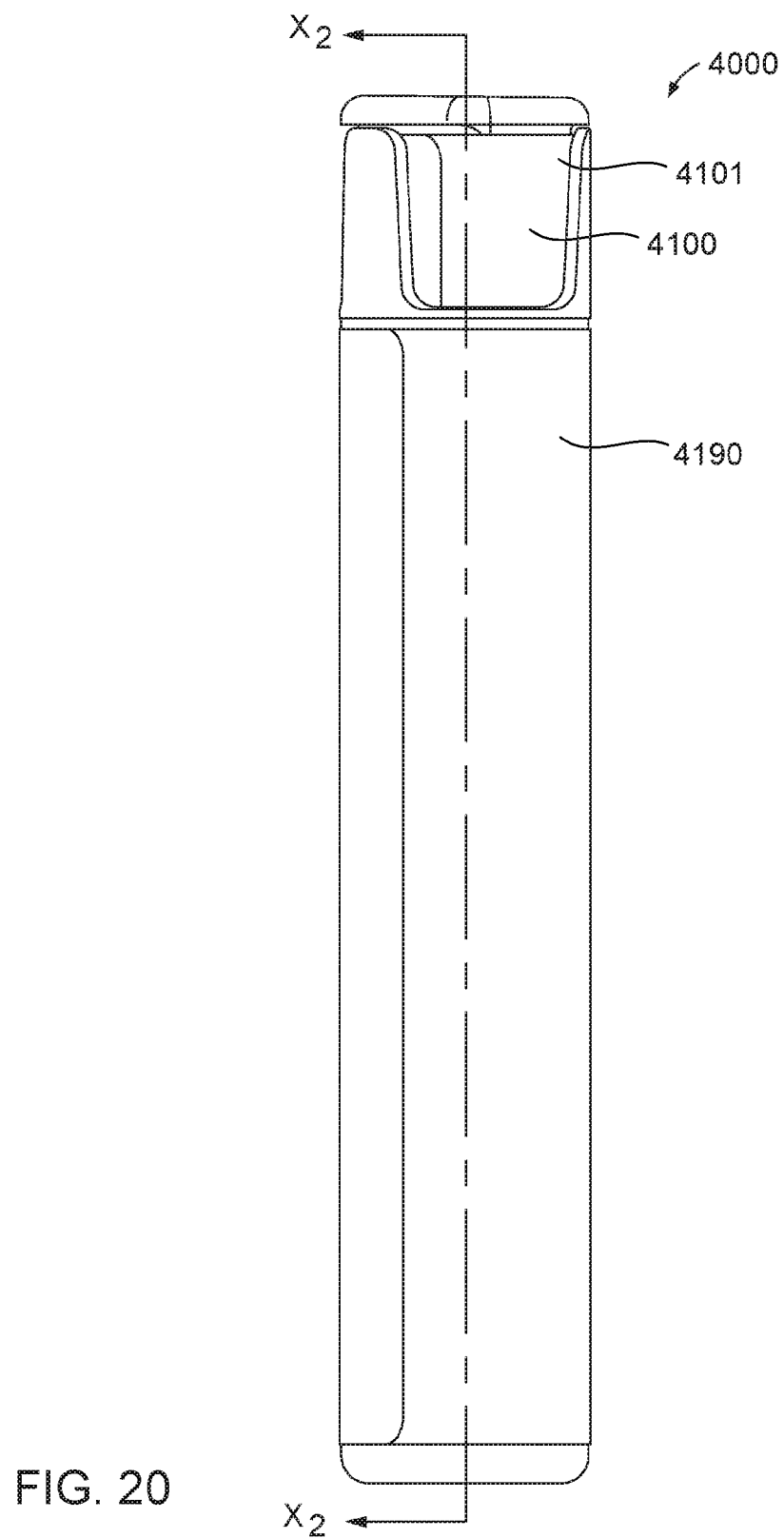
FIG. 20 is a side view of a medical injector according to an embodiment.
Figure 21:
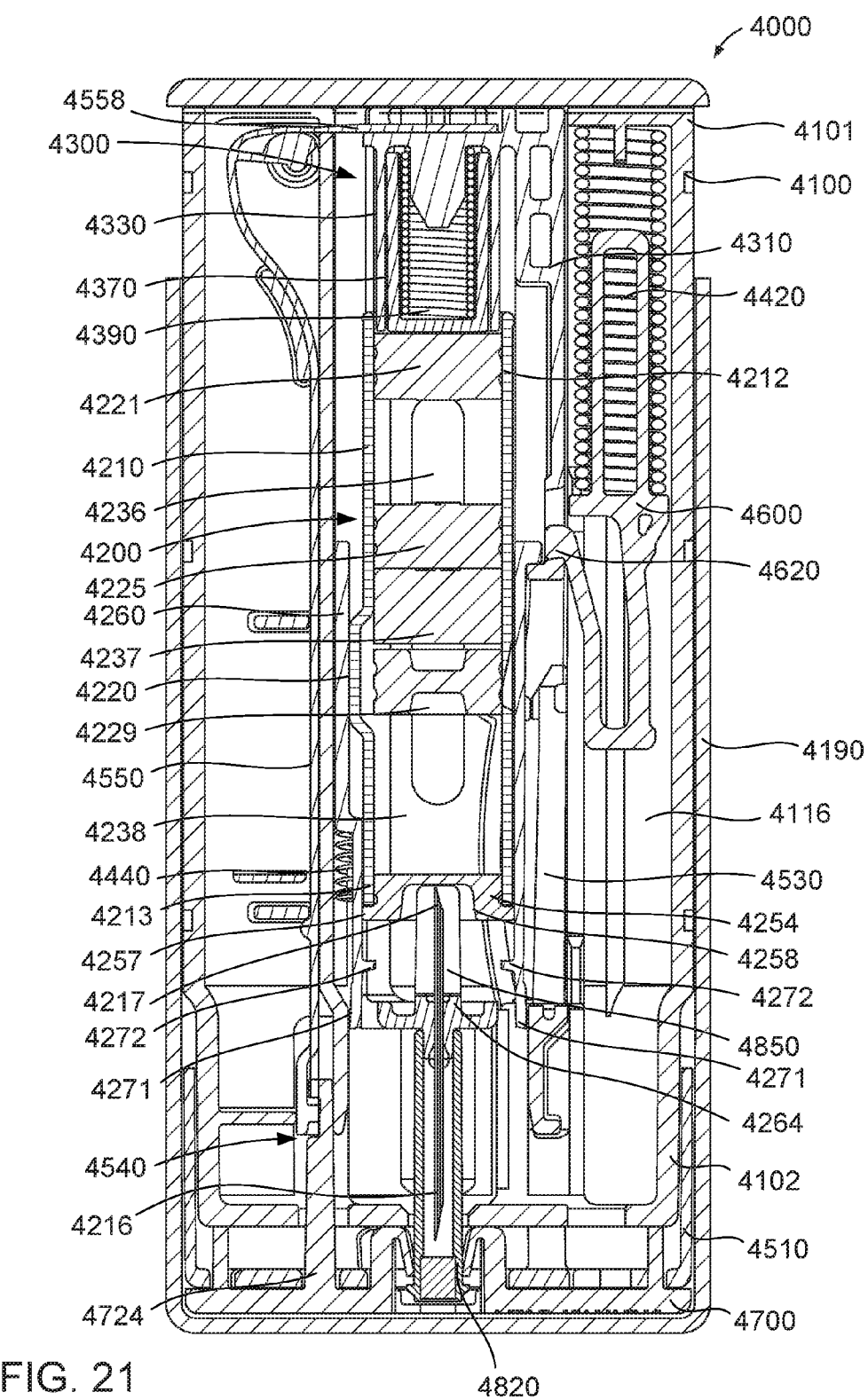
FIG. 21 is a cross-section view of the medical injector taken along the line $X_2$-$X_2$ in FIG. 20, in a first configuration.

FIG. 20 is a side view of the medical injector 4000 in a first configuration. As shown in FIG. 21, the medical injector 4000 includes a housing 4100, a system actuator assembly 4500, a medicament container assembly 4200 containing a medicament 4240, a movable assembly 4300, a transfer member 4600, a cover 4190, and a safety lock 4700. In some embodiments, portion of the medical injector 4000 can be substantially similar to the medical injector 4000, described above.

The housing 4100 has a proximal end portion 4101 and a distal end portion 4102. The proximal end portion 4102 includes an end cap configured to substantially enclose the proximal end. The distal end portion 4103 can include any suitable feature to engage and/or otherwise receive at least a portion of the system actuator 4500 (e.g., a base 4510). For example, the distal end portion 4103 can include recesses, grooves, slots, notches, openings, protrusions and/or any other suitable feature. The housing 4100 is configured to substantially enclose and/or otherwise house at least a portion of the system actuator assembly 4500, the medicament container assembly 4200, the movable assembly 4300, the transfer assembly 4600, and the safety lock 4700.

The distal end portion 4100 of the housing 4100 is configured to receive an activator 4530 (also referred to herein as "release member 4530," and/or "rod 4530" included in the base 4510 of the system actuator assembly 4500. As described in more detail herein, the release member 4530 of the base 4510 is configured to engage a portion of the movable assembly 4300 (also referred to herein as "medicament delivery mechanism 4300") when the base 4510 is moved with respect to the housing 4100 to actuate the medical injector 4000. The housing 4100 includes an inner surface 4116 that can include any suitable feature configured to limit, guide, contact, separate, and/or otherwise engage a portion of the medicament container assembly 4200, the system actuator assembly 4500, the movable assembly 4300, the transfer assembly 4600, and the safety lock 4700. For example, the inner surface 4116 can include guides (not shown herein) configured to engage at least a portion of the medicament container assembly 4200 as the medicament container assembly 4200 moves from a proximal position, relative to the housing 4100, to a distal position, relative to the housing 4100. Furthermore, the housing 4100 define an opening (not shown herein) that receives a portion of a needle 4216 of the medicament container assembly 4200 such that the needle 4216 is disposed substantially outside the housing 4100 when the medicament container assembly 4200 is in the distal position, as described in further detail herein.

As shown in FIGS. 20 and 21, the cover 4190 is configured to be disposed about a portion of the housing 4100. Thus, when the portion of the housing 4100 is disposed within the cover 4190, the cover 4190 blocks an optical pathway between the medicament container 4210 and a region outside of the housing 4100. Similarly stated, when the portion of the housing 4100 is disposed within the cover 4190, the cover 4190 reduces the amount of light transmitted to the medicament within the medicament container 4210. In this manner, the life of the medicament can be extended by the prevention and/or reduction of degradation to the medicament that may be caused by ultra-violet radiation.

The medicament container assembly 4200 includes a medicament container 4210, the needle 4216, and the carrier 4260. The medicament container 4210 includes a proximal end portion 4212, a distal end portion 4213, and a bypass 4220. The medicament container 4210 can be substantially similar to the medicament container 3210 described above. Therefore, the medicament container 4210 is not described in detail herein.

The distal end portion 4213 of the medicament container 4210 is configured to engage at least a portion of the carrier 4260 and the needle 4216, as described below. The distal end portion 4213 of the medicament container 4210 receives a stopper 4254. More specifically, the stopper 4254 is configured to be disposed within the medicament container 4210 to define a substantially fluid tight and/or hermetic seal. Furthermore, the stopper 4254 includes a flange 4257 that engages a distal surface of the medicament container 4210. The flange 4257 is further configured to define a friction fit with a portion of the carrier 3260 such that the medicament container 4210 is selectively retained relative to the carrier 3260, as further described herein. The stopper 4254 further includes a set of inner walls 4258 defining a recess configured to receive a proximal end portion 4217 of the needle 4216, a portion of the carrier 4260, and a deformable sheath 4850. The deformable sheath 4850 can be any suitable shape, size, or configuration and is configured to substantially enclose at least a portion of the needle 3216. In this manner, the deformable sheath can be configured to substantially maintain the sterility of the needle 3216 prior to an injection event.

The proximal end portion 4212 of the medicament container 4210 receives a first elastomeric member 4221, a second elastomeric member 4225, and a third elastomeric member 4229. In some embodiments, the first elastomeric member 4221, the second elastomeric member 4225, and the third elastomeric member 4229 are placed within the medicament container 4210 during the fill process, as further described herein, to define a diluent volume 4236, a dry medicament volume 4237, and a void volume 4238 (see, e.g., FIG. 12). The dry medicament volume 4237 is a volume disposed within medicament container 4210 defined between a distal surface 4227 of second elastomeric member 4225 and a proximal surface 4230 of third elastomeric member 4229 and the void volume 4238 is a volume disposed within the medicament container 4210 defined between a distal surface 4231 of the third elastomeric member 4229 and the distal end portion 4213 of the medicament container 4210.

The diluent volume 4236, the dry medicament volume 4237, and the void volume 4238 are defined by the positions of the first elastomeric member 4221, the second elastomeric member 4225, and the third elastomeric member 4229, relative to and/or within the medicament container 4210. In some embodiments, the diluent volume 4236 can contain a medicament diluent, such as, for example, water. In some embodiments, the dry medicament volume 4237 can contain a lyophilized medicament (e.g., any suitable medicament produced via any suitable lyophilizing process) including any of the formulations and/or compositions described herein.

As shown in FIG. 21, the proximal end portion 4212 of the medicament container 4210 is coupled to and/or receives a portion of the medicament delivery mechanism 4300 such that medicament delivery mechanism 4300 can move the first elastomeric member 4221, the second elastomeric member 4225, and/or the third elastomeric member 4229 to vent, mix and/or inject the medicament disposed therein. More specifically, the proximal end portion 4212 of the medicament container 4210 can receive a piston portion 4330 of a first movable member 4301 and a second movable member 4370 (also referred to herein as a "mixing piston 4370").

As described above, the medicament container 4210 is configured to engage and/or be coupled to the carrier 4260. The carrier 4260 includes a proximal end portion 4261, a distal end portion 4262, and a needle hub 4264. In some embodiments, the carrier 4260 can be substantially similar to the carrier 3260 described above. Therefore, details of the carrier 4260 are not described herein. The carrier 4260 can differ from the carrier 3260, however, in the length and/or configuration of the needle hub 4264. For example, as shown in FIGS. 21-27, the needle hub 4264 is substantially shorter than the needle hub 3264. Although, the needle hub 4264 is shorter than the needle hub 3264, the needle hub 4264 can be similar in function to the needle hub 3264; thus the needle hub 4264 is not described in further detail herein. The carrier 4260 includes a set of tabs 4271 that include a container shoulder 4272. The set of tabs 4271 are configured to selectively engage a portion of the housing 4100 as the medicament container assembly 4200 is moved in the proximal direction during an injection event. The arrangement of the tabs 4271, the housing 4100, and the container shoulders 4272 are such that the flange 4257 of the stopper 4254 can selectively engage the container shoulder 4272 when moving between the first container position and the second container position, as described in further detail herein.

The system actuator assembly 4500 includes the base 4510, the release member 4530, and a mixing actuator assembly 4540. The release member 4530 is configured to engage a latch portion 4310 of the medicament delivery mechanism 4300 when the medical injector 4000 is in its first (or storage) configuration (FIG. 21). In this manner, the release member 4530 maintains the latch portion 4310 in contact with a portion of the housing 4100. When the portion of the housing 4100 is in contact with the latch portion 4310, the portion of the housing 4100 applies a reaction force to the latch portion 4310 in response to the force applied by a spring 4420 configured to urge the transfer member 4600 and the medicament delivery mechanism 4300 in a distal direction. Similarly stated, when the latch portion 4310 is in contact with the housing 4100, the housing 4100 limits distal movement of the latch portion 4310, and thus, the medicament delivery mechanism 4300. In this manner, when the base 4510 is in a first position (i.e., before actuation of the medical injector 4000), the release member 4530 maintains the latch portion 4310 in contact with the housing 4100 and maintains the medical injector 4000 in the first configuration. Furthermore, when the medical injector 4000 is in the first configuration, at least a portion of the safety lock 4700 is disposed within a portion of the base 4510 such that the portion of the safety lock 4700 prevents the movement of the base 4510 in the proximal direction relative to the housing 4100.

The mixing actuator assembly 4540 includes the mixing actuator member 4550 and the safety lock 4700. As shown in FIG. 21, the safety lock 4700 includes the safety lock actuator 4724. The safety lock actuator 4724 is configured to selectively engage the mixing actuator member 4550. In this manner, when the safety lock 4700 is moved in the distal direction to be removed from the medical injector 4000, the safety lock actuator 4724 contacts the mixing actuator member 4550 such that the removal of the safety lock 4700 moves a portion of the mixing release member 4550 in the distal direction, as described in further detail herein.

The mixing actuator member 4550 includes a retention portion 4558 movably disposed within a portion of the first movable member 4301. The retention portion 4558 is configured to move within the portion of the first movable member 4301 between a first position (e.g., the locked position) and a second position (e.g., the mixing position). The mixing piston 4370 is disposed within the piston portion 4330 of the first movable member 4301 such that a portion of the mixing piston 4370 selectively engages the retention portion 4558 of the mixing actuator 4550. In this manner, when the mixing actuator 4550 is in the first position, the mixing piston 4370 is maintained in the first configuration. Furthermore, when the safety lock 4700 is moved in the distal direction (e.g., removed from the medical injector 4000), the retention portion 4558 is moved to the second position such that the mixing piston 4370 is actuated to urge a mixing event, as described in further detail herein.

The medicament delivery mechanism 4300 (all or portions of which can also be referred to as a "movable assembly") includes the first movable member 4301, the second movable member 4370 (the mixing piston 4370), and a mixing spring 4390. The arrangement of the first movable member 4301, the second movable member 4370, and the mixing spring 4390 is such that the mixing spring 4390 can be actuated to move the second movable member 4370 relative to the first movable member 4301 to urge a venting and/or mixing event.

The first movable member 4301 includes a latch portion 4310 and a piston portion 4330. The latch portion 4310 of the first movable member 4301 extends in the distal direction and is configured to selectively engage a portion of the housing 4100 and the release member 4530. The latch portion 4310 is further configured to engage a latch 4620 of the transfer member 4600. More particularly, when the medical injector 4000 is in the first configuration (i.e., prior to actuation), the latch portion 4310 of the first movable member 4301 is in contact with the latch 4620 of the transfer member 4600. In this manner, the transfer member 4600 can transfer a force produced by the spring 4420 to the latch portion 4310 of the first movable member 4300 to move the medicament delivery mechanism 4300 in the distal direction when the medical injector 4000 is actuated. Similarly stated, this arrangement allows the medicament delivery mechanism 4300 and/or the first movable member 4301 to move with and/or remain coupled to the transfer member 4600 during the insertion and/or injection operation.

The piston portion 4330 is configured to receive at least a portion of the mixing spring 4390 and the mixing piston 4370. More specifically, the medicament delivery mechanism 4300 is configured such that when the medical injector 4000 is in the first configuration (e.g., the storage configuration), the mixing spring 4390 is disposed within the piston portion 4330 and the mixing piston 4370 in a first (e.g., compressed) configuration (see e.g., FIG. 21). The arrangement of the first movable member 4301, the mixing piston 4370, and the mixing actuator member 4550 is such that when the mixing actuator member 4550 is moved to actuate a venting and/or mixing event, the mixing spring 4390 expands to move the mixing piston 4370 in the distal direction. Thus, the expansion of the mixing spring 4390 is such that the mixing spring 4390 exerts a force on the mixing piston 4370 to move the mixing piston 4370 in the distal direction, as further described herein.

The transfer member 4600 includes the latch and can receive and/or engage a portion of the spring 4420. The latch 4620 is configured to engage the latch portion 4310 of the first movable member 4301. In this manner, the transfer member 4600 transfers a force from the actuation of the spring 4420 to the first movable member 4301 and/or the medicament delivery mechanism 4300 to move the medicament delivery mechanism 4300 in the distal direction within the housing 4100. In this manner, the force produced by the spring 4420, which is offset from the medicament delivery mechanism 4300 and/or the medicament container 4210, results in both the insertion of the needle 4216 and injection of the medicament within the medicament container 4210. Although, as described below, the mixing spring 4390 produces a force to vent and/or mix a diluent and a lyophilized medicament, in other embodiments, a portion of the force produced by the spring 4420 can be used to facilitate the mixing process.

Figure 27:
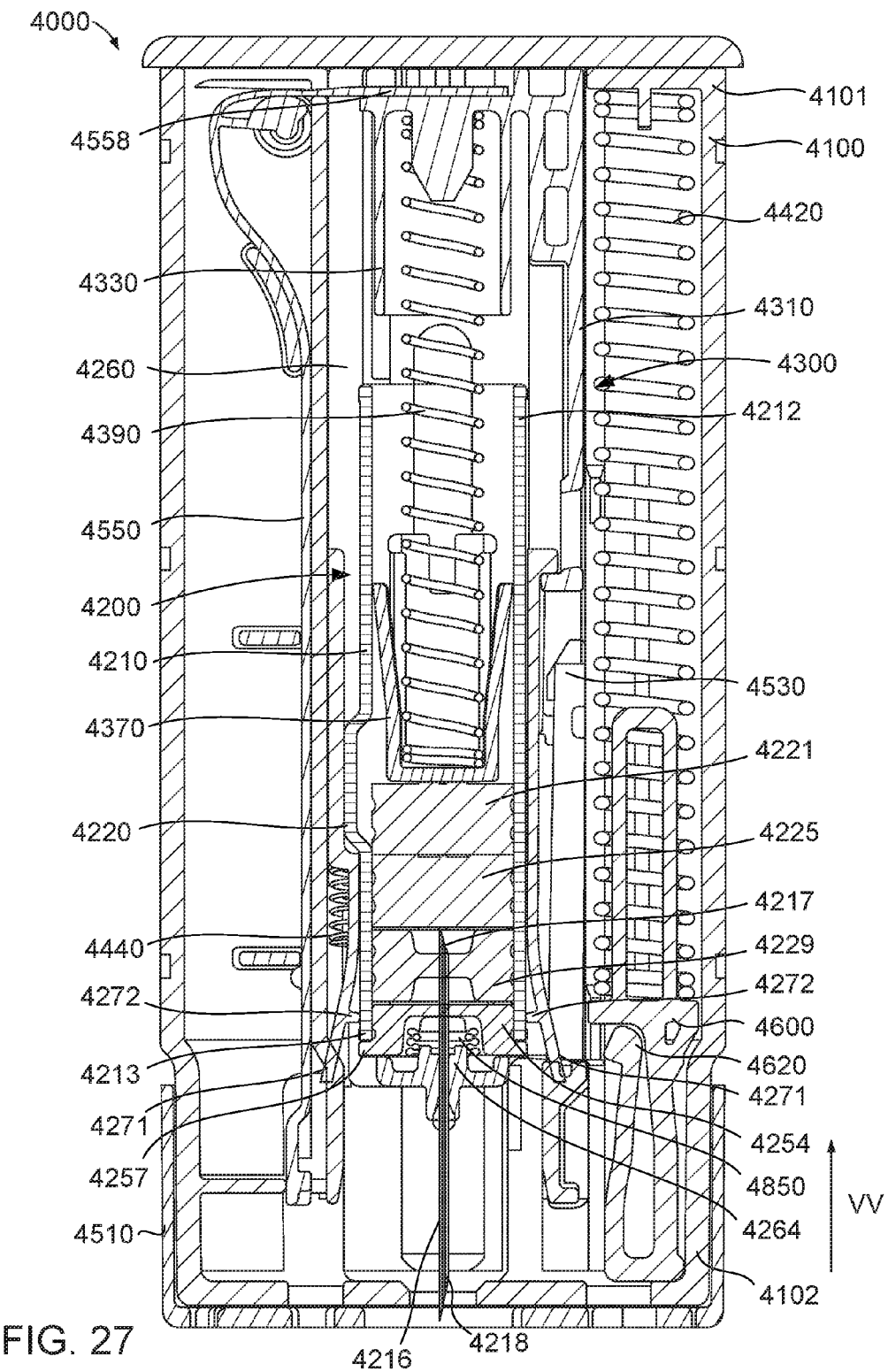

Furthermore, when the transfer member 4600 has moved a desired distance in the distal direction in response to the force produced by the actuation of the spring 4420 (e.g., upon completion of the medicament injection), the transfer member 4600 can be moved to a second configuration (see e.g., FIG. 27). In this manner, the latch 4620 can be disengaged from the latch portion 4310. Similarly stated, when the transfer member 4600 is in its second configuration, the latch 4620 is disengaged from the first movable member 4301, and the force produced by the spring 4420 is no longer transferred to the medicament delivery mechanism 4300. Said yet another way, when the transfer member 4600 is in its second configuration, the medicament delivery mechanism 4300 is isolated and/or no longer operably coupled to the spring 4420. In this manner, as described below, the retraction force exerted by the retraction spring 4440 moves the medicament delivery mechanism 4300 and/or the medicament container assembly 4200 proximally within the housing 4100 to retract the needle 4216 (FIG. 27).

As described above, the safety lock 4700 can be configured to selectively engage a portion of the housing 4100 to maintain the medical injector 4000 in the first configuration. Furthermore, the safety lock can be coupled to a needle sheath 4820 configured to be disposed about a portion of the needle 4216. When the medical injector 4000 is in the first configuration, the needle sheath 4820 can further be configured to receive the lower needle port 4268 of the carrier 4260 such that the lower needle port 4268 and the needle sheath 4820 define a substantially fluid tight and/or hermetic seal. Thus, the arrangement of the needle sheath 4820 and the lower needle port 4268 can maintain the sterility of the needle 4216 prior to actuation of the medical injector 4000 (e.g., during storage).

Figure 22:
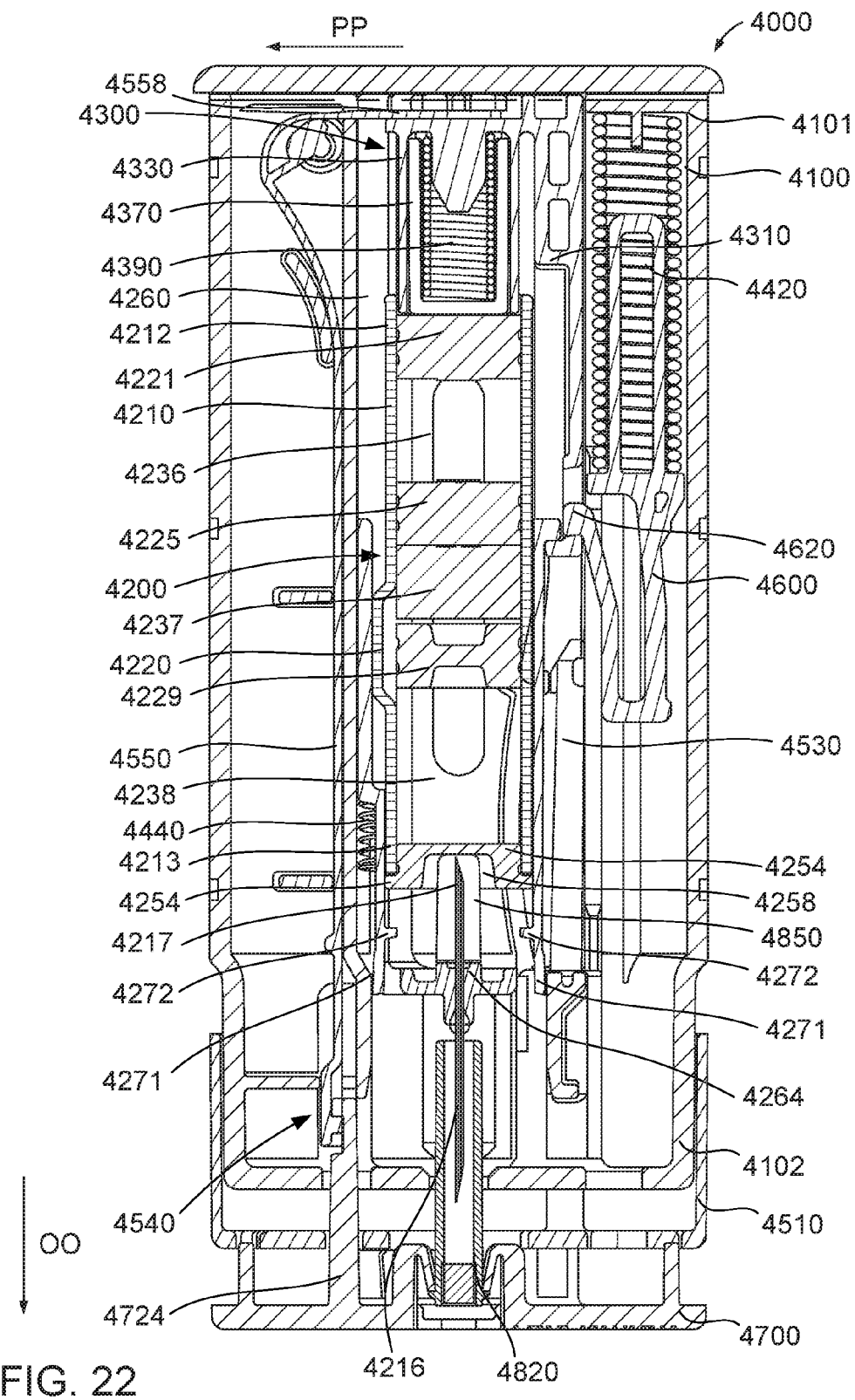
FIGS. 22 and 23 are cross-section views of the medical injector taken along the line $X_2$-$X_2$ in FIG. 20, being moved from the first configuration to a second configuration.
Figure 23:
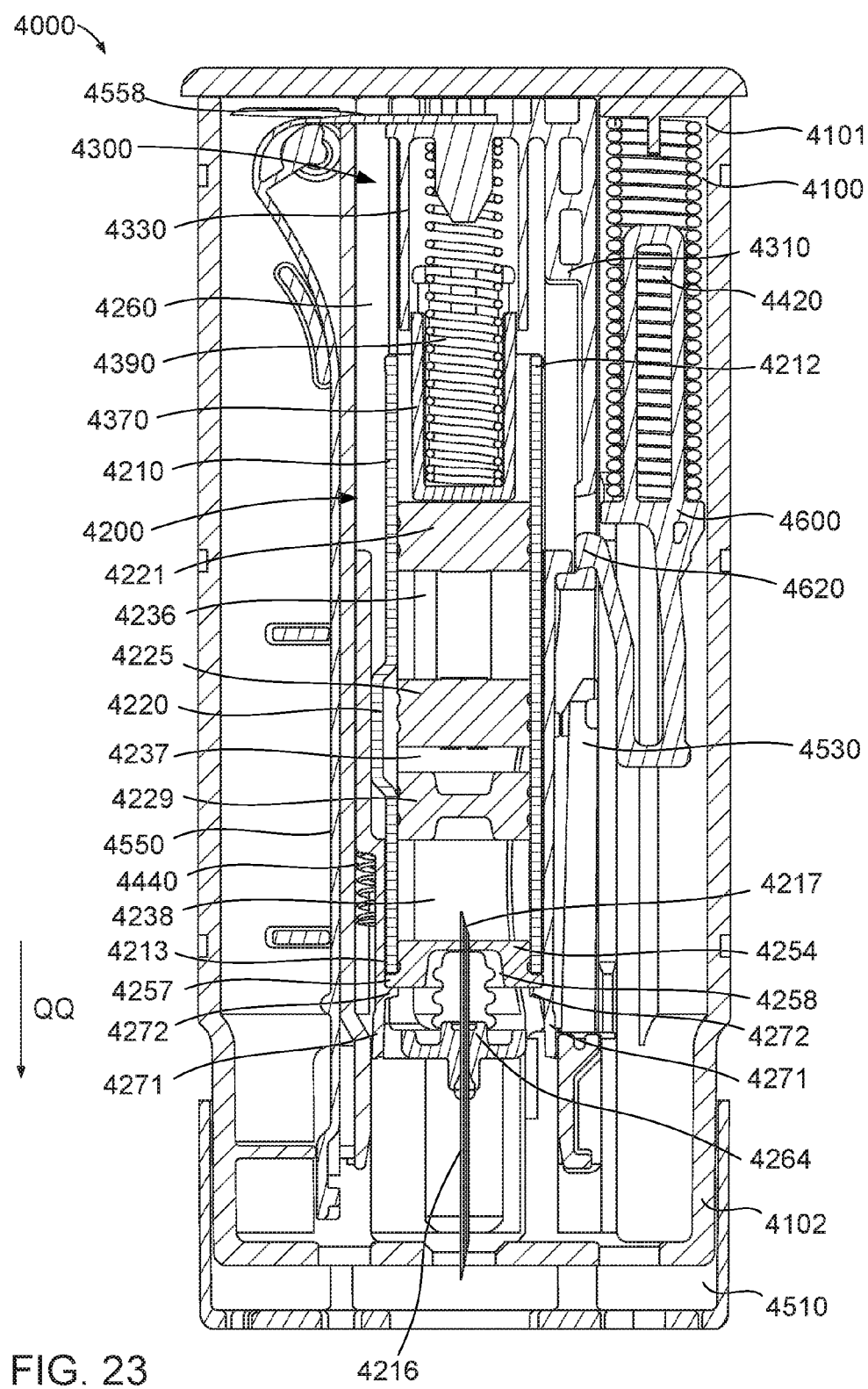

As shown in FIGS. 22 and 23, the medical injector 4000 is first enabled by moving the medicament delivery device 4000 from the first configuration to the second configuration by removing the cover 4190 and moving the safety lock 4700 in the direction shown by the arrow OO. When the safety lock 4700 is moved from the first position to the second position, the safety lock 4700 is no longer in contact with the distal end portion 4103 of the housing 4100, thereby enabling the medicament delivery mechanism 4300. Additionally, when the safety lock 4700 is removed from and/or moved relative to the housing 4100, the actuator 4724 of the safety lock 4700 also moves in the direction OO to actuate the mixing actuator member 4550. More specifically, when the actuator 4724 is moved in the direction OO, a portion of the mixing actuator member 4550 pivots relative to the housing 4100 such that the retention portion 4558 moves in the direction of the arrow PP.

As shown in FIG. 23, the lateral motion of the retention portion 4558 is such that the retention portion 4558 disengages the mixing piston 4370. In this manner, the retention portion 4558 no longer maintains the mixing spring 4390 in the first configuration (e.g., the compressed configuration). Therefore, when the retention portion 4558 moves laterally, the mixing spring 4390 expands to the second configuration and exerts a force to move the mixing piston 4370 in the distal direction, as indicated by arrow QQ in FIG. 23.

With the mixing spring 4390 in the second configuration (e.g., the expanded configuration), much of the mixing piston 4370 is disposed outside the piston portion 4330 of the first movable member 4301. Similarly stated, the mixing piston 4370 is disposed in a distal position relative to the piston portion 4330 of the first movable member 4301.

Figure 24:
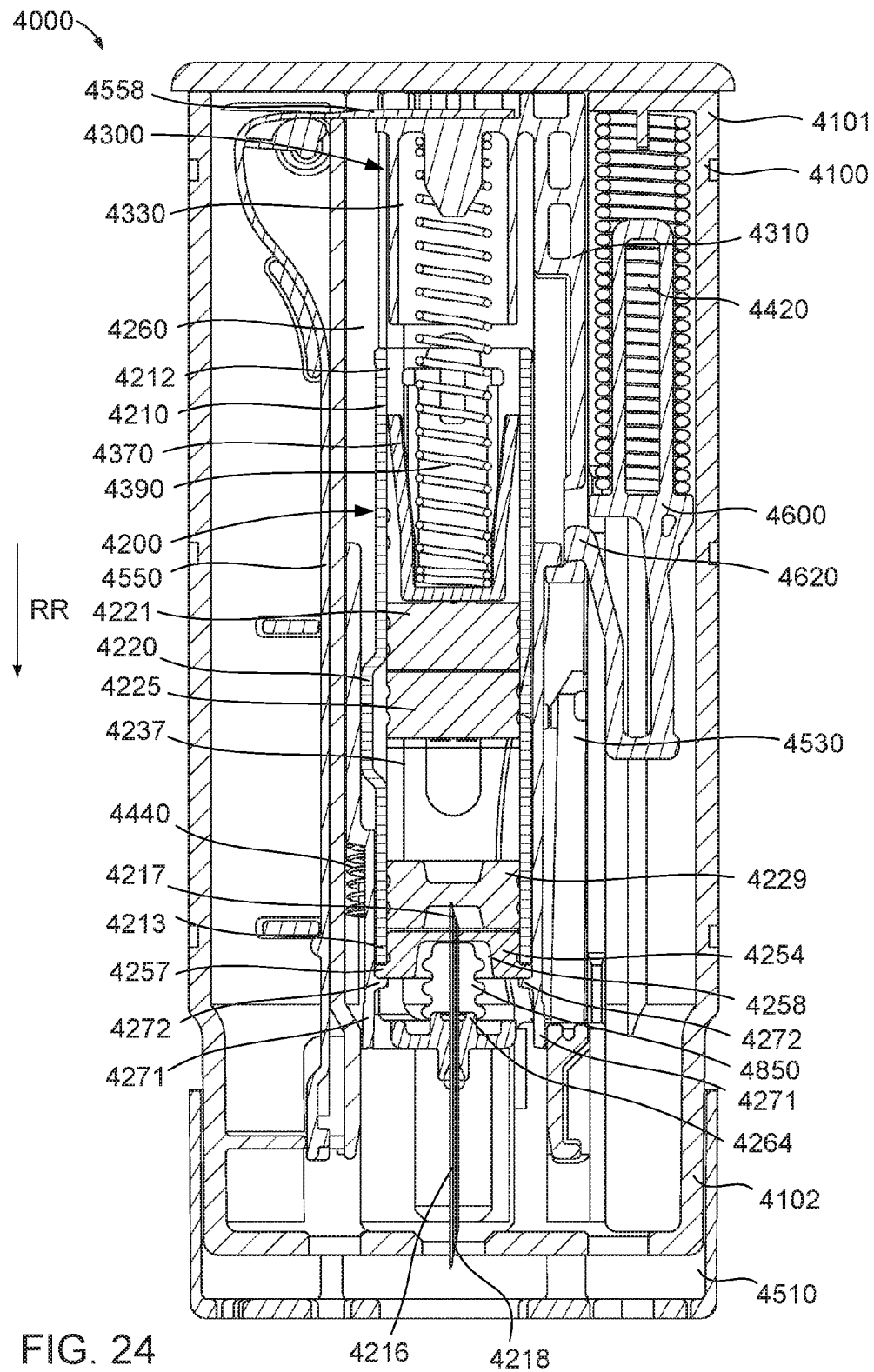
FIGS. 24-27 are cross-sectional views of the medical injector taken along the line $X_2$-$X_2$ in FIG. 20, in a third, fourth, fifth, and sixth configuration, respectively.

The distal movement of the mixing piston 4370 begins the venting and mixing event, as shown in FIGS. 23 and 24. More specifically, the mixing piston 4370 engages the first elastomeric member 4221 and transfers a portion of the force exerted by the mixing spring 4390 to move at least the first elastomeric member 4221 in the distal direction. The arrangement of the elastomeric members within the medicament container 4210 is such that the portion of the force exerted on the first elastomeric member 4221 moves the medicament container 4210 in the distal direction relative to the carrier 4260. Expanding further, the medicament container 4210 is disposed within the carrier 4260 such that the flange 3257 of the stopper 3254 defines the friction fit with the carrier 4260. The exertion of the force by the mixing spring 4390 is such that the friction force between the flange 3257 and the carrier 4260 is overcome, thus the medicament container 4210 moves in the distal direction relative to the carrier 4260. More specifically, the elastomeric members are disposed within the medicament container 4210 such that the friction force between the elastomeric members and the walls of the medicament container 4210 is greater than the external force to move the medicament container 4210 relative to the carrier 4260. Thus, when the mixing spring 4390 is actuated to apply the mixing force to the first elastomeric member 4221, the medicament container 4210 moves in the direction of the arrow QQ shown in FIG. 23, relative to the carrier 4260. Therefore, the flange 4257 of the stopper 4254 is placed in contact with the protrusions 4272 of the carrier 4260. In this manner, the protrusions 4272 temporarily prevent further distal movement of the medicament container 4210 relative to the carrier 4260. Furthermore, the distal movement of the medicament container 4210 relative to the carrier 4260 is such that the deformable sheath 4850 is deformed (e.g., compressed) and the proximal end portion 4217 of the needle 4216 pierces the proximal end portion 4255 of the stopper 4254 such that the proximal end portion 4217 of the needle 4216 is disposed within the void volume 4238.

Concurrently, a portion of the mixing force moves the first elastomeric member 4221, the second elastomeric member 4225, and the third elastomeric member 4229 in the direction of the arrow QQ. The lyophilized medicament disposed within the dry volume 4237 is configured to compress such that the volume of the lyophilized medicament is reduced. More specifically, the lyophilized medicament can be configured to include approximately 93% air. As shown in FIG. 22, with the dry volume 4237 in fluid communication with the bypass 4220, the air portion of the lyophilized medicament can flow through the bypass 4220 and into the void volume 4238. Thus, as shown in FIG. 23, the volume of the lyophilized medicament is reduced and the third plunger is moved beyond the bypass 4220. In addition, with the proximal end portion 4217 of the needle 4216 in fluid communication with the void volume 4238, the air portion of the lyophilized medicament can be vented through the needle 4216 prior to the insertion of the needle 4216 into the patient.

As shown in FIG. 24, further distal movement of the mixing piston 4370 places the medical injector 4000 a third configuration. Therefore, the mixing piston 4370 moves in the direction of the arrow RR to place the diluent volume 4236 in fluid communication with the dry medicament volume 4237 via the bypass 4220 such that the diluent within the diluent volume 4236 is transferred to the dry medicament volume 4237. More specifically, the mixing piston 4370 continues to move the first elastomeric member 4221, the second elastomeric member 4225, and the third elastomeric member 4229 in the distal direction such that the third elastomeric member 4229 is placed in contact with the stopper 4254 and the diluents volume 4236 and the dry medicament volume 4237 are placed in fluid communication. Thus, the diluent can mix with the lyophilized medicament disposed within the dry medicament volume 4237 to reconstitute the medicament for injection. In this manner, the first elastomeric member 4221 is moved into contact with the second elastomeric member 4225 such that substantially all the diluent within the diluents volume 4236 are mixed with the lyophilized medicament.

After the mixing event, the medical injector 4000 can be moved from the third configuration (FIG. 24) to a fourth configuration (FIG. 25) by moving the base 4510 from a first position to a second position. Similarly stated, the medical injector 4000 can be actuated by the system actuator assembly 4500 by moving the base 4510 proximally relative to the housing 4100. The base 4510 is moved from its first position to its second position by placing the medical injector 4000 against the body of the patient and moving the base 4510 with respect to the housing 4100 in the direction shown by the arrow SS in FIG. 25.

When the base 4510 is moved from the first position to the second position, the system actuator assembly 4500 actuates the medicament delivery mechanism 4300, thereby placing the medical injector 4000 in its fourth configuration (i.e., the needle insertion configuration). More specifically, the proximal movement of the system actuator assembly 4500 and/or the base 4510 moves the release member 4530 in the proximal direction within the housing 4100, thereby allowing the latch portion 4310 to be disengaged from the release member 4530. Thus, the spring 4420 is allowed to expand in the direction shown by the arrow TT in FIG. 25. In this manner, the latch 4620 of the transfer member 4600 transfers at least a portion of the force to the latch portion 4310 of the first movable member 4301 such that the portion of the force moves the medicament delivery mechanism 4300 in the distal direction, shown by the arrow TT. Thus, the first movable member 4301 and the transfer member 4600 move together distally within the housing 4100.

When the medicament delivery mechanism 4300 is moving distally, the piston portion 4330 of the first movable member 4301 applies a portion of the force to the medicament container 4210. More specifically, the portion of the force exerted by the piston portion 4330 and/or the mixing piston 4370 moves the medicament container assembly 4200 in the distal direction. As shown in FIG. 24, when the medicament container assembly 4200 is in the first position (e.g., prior to being moved by the portion of the insertion force), the protrusions 4272 of the needle insertion tabs 4271 included in the carrier 4260 are in contact with the flange 4257 of the stopper 4254. Therefore, when the portion of the insertion force is exerted on the first elastomeric member 4221, the force is transferred through the medicament container 4210 to the protrusions 4272 to move the carrier 4260 in the distal direction.

Figure 25:
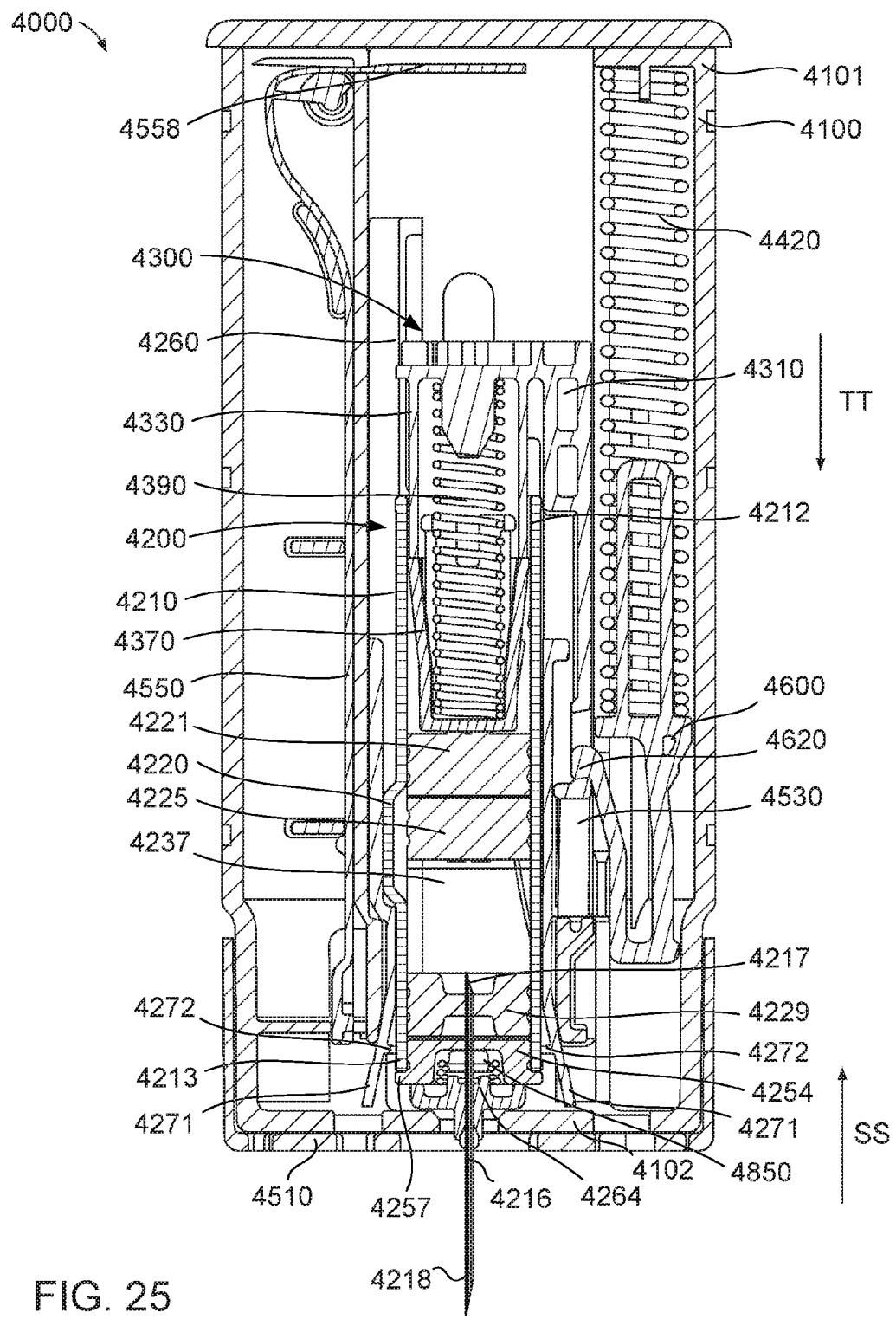
Figure 26:
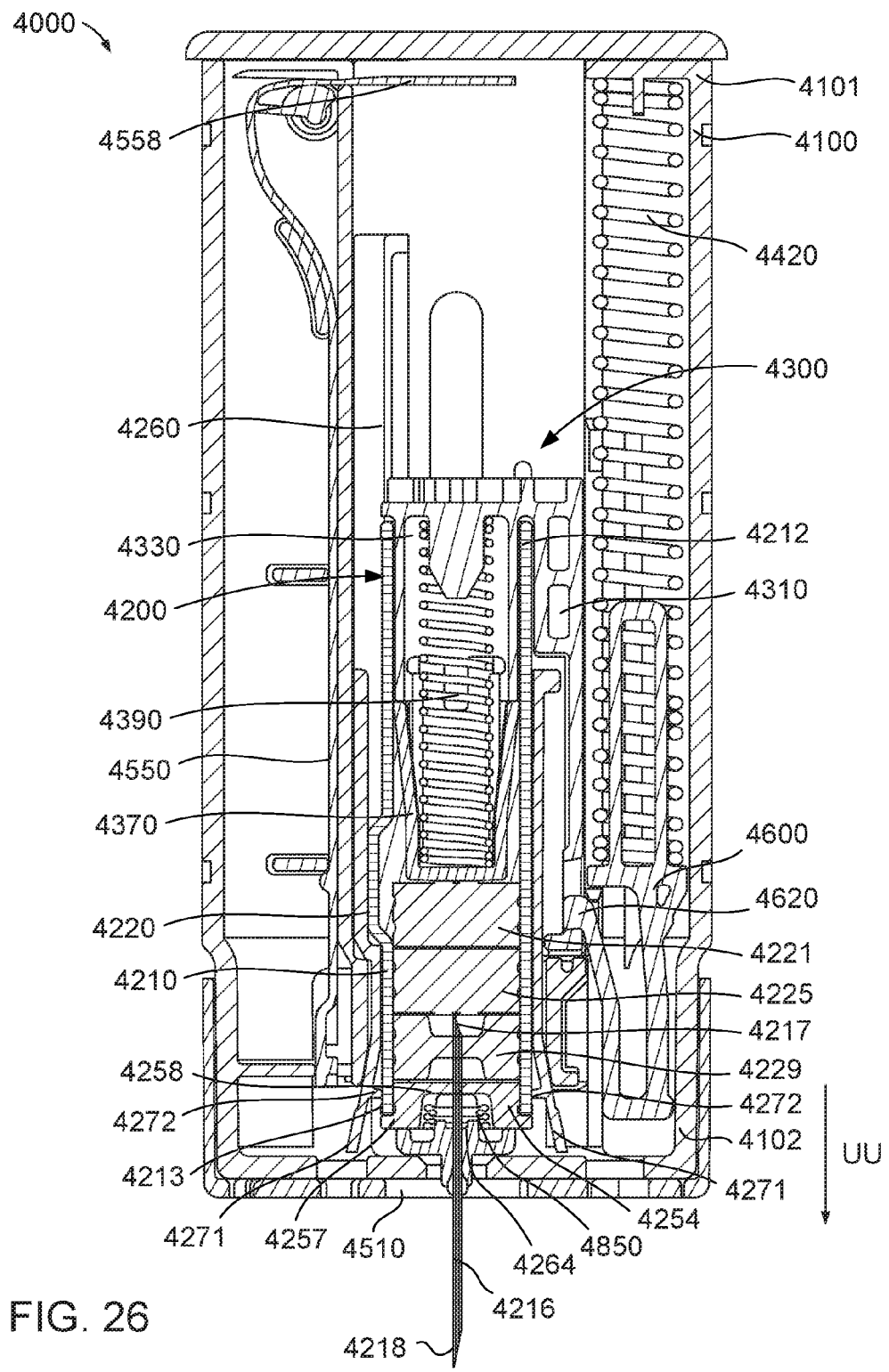

As shown in FIG. 25, the carrier 4260 moves to a second position within the housing 4100 during the needle insertion operation. With the carrier 4260 in the second position, a tabs 4271 of the carrier 4260 contact the housing 4100, thereby limiting the distal movement of the carrier 4260. Furthermore, the tabs 4271 are disengage from a portion of the housing 4100 such that the tabs 4271 expand. In the expanded configuration, the tabs 4271 extend such that the flange 4254 is no longer in contact with the protrusions 4272. Thus, the portion of the insertion force applied to the first elastomeric member 4221 moves the medicament container 4210 in the distal direction, relative to the carrier 4260. In this manner, the deformable sheath 4850 is further compressed and the proximal end portion 4217 of the needle 4216 punctures through the thickness of the third elastomeric member 4229 and the medical injector 4000 can be placed in a fifth configuration (i.e., the medicament delivery configuration).

The medical injector 4000 is placed in the fifth configuration when the proximal end portion 4217 of the needle 4216 is disposed within the mixing volume 4237 (e.g., the dry medicament volume 4237) and a portion of the insertion force is exerted on the first elastomeric member 4221. With the medicament container 4210 and the carrier 4260 in the second position within the housing 4100 (e.g., moved in the distal direction), the portion of the force exerted on the first elastomeric member 4221 can move the first elastomeric member 4221 and the second elastomeric member 4225 from the second position to a third position within the medicament container 4210. More specifically, the mixing piston 4370 and/or piston portion 4330 exerts the portion of the force on the first elastomeric member 4221 as indicated by arrow UU in FIG. 26 to move the first elastomeric member 4221 and the second elastomeric member 4225 to the third position. In this manner, the medicament disposed within the dry medicament volume 4237 is transferred to the needle 4216 and injected into the body of the patient.

When the spring 4420 fully expands, the medicament delivery mechanism 4300 moves in the distal direction to fully inject the medicament within the medicament container 4210. Additionally, when the spring 4420 is fully expanded and/or when the medicament delivery mechanism 4300 has moved a desired distance within the housing 4100, the transfer member 4600 can be placed in the second configuration. In this manner, the latch 4620 can be disengaged from the latch portion 4310. Similarly stated, the spring 4420 and/or the transfer member 4600 are decoupled from the medicament delivery mechanism 4300. With the latch 4620 disengaged from the latch portion 4310, the medical injector 4000 can be moved from the fifth configuration to the sixth configuration (i.e., the retraction configuration).

With the transfer member 4600 disengaged from the medicament delivery mechanism 4300, the medicament container assembly 4200 and the medicament delivery mechanism 4300 are configured to move within the housing 4100 in the direction shown by the arrow VV in FIG. 27 in response to a force exerted by the retraction member 4440 (e.g., the retraction spring). Similarly stated, with the medicament delivery mechanism 4300 disengaged from the transfer member 4600 and/or the spring 4420, the insertion force is no longer applied to the medicament delivery mechanism 4300. In this manner, the retraction member 4440 is configured to expand in the direction of the arrow VV to apply a retraction force to the medicament container assembly 4200. Similarly stated, with the portion of the force insertion configured to compress the retraction spring 4440 removed, the retraction member 4440 expands, returning to its uncompressed (i.e., non-deformed) configuration.

During the retraction operation, the retraction spring 4440 exerts a retraction force on the retraction spring surface 4284 to move the carrier 4260 in the direction VV. With the medicament container 4210 coupled to the carrier 4260 a portion of the retraction force moves the medicament container 4210 in the proximal direction. This motion, removes the needle 4216 from the target location of the patient and retracts the needle into the housing 4100, as shown in FIG. 27.

While the medicament container 5210 is shown and described above in FIGS. 20-27 as being moved to proximal end portion 5217 of the needle 5216 in fluid communication with the void volume 5238, in other embodiments, a proximal end portion of a needle can be disposed within a void volume prior to an injection event. For example, FIGS. 28-35 illustrate a medical injector 5000 according to an embodiment.

Figure 28:
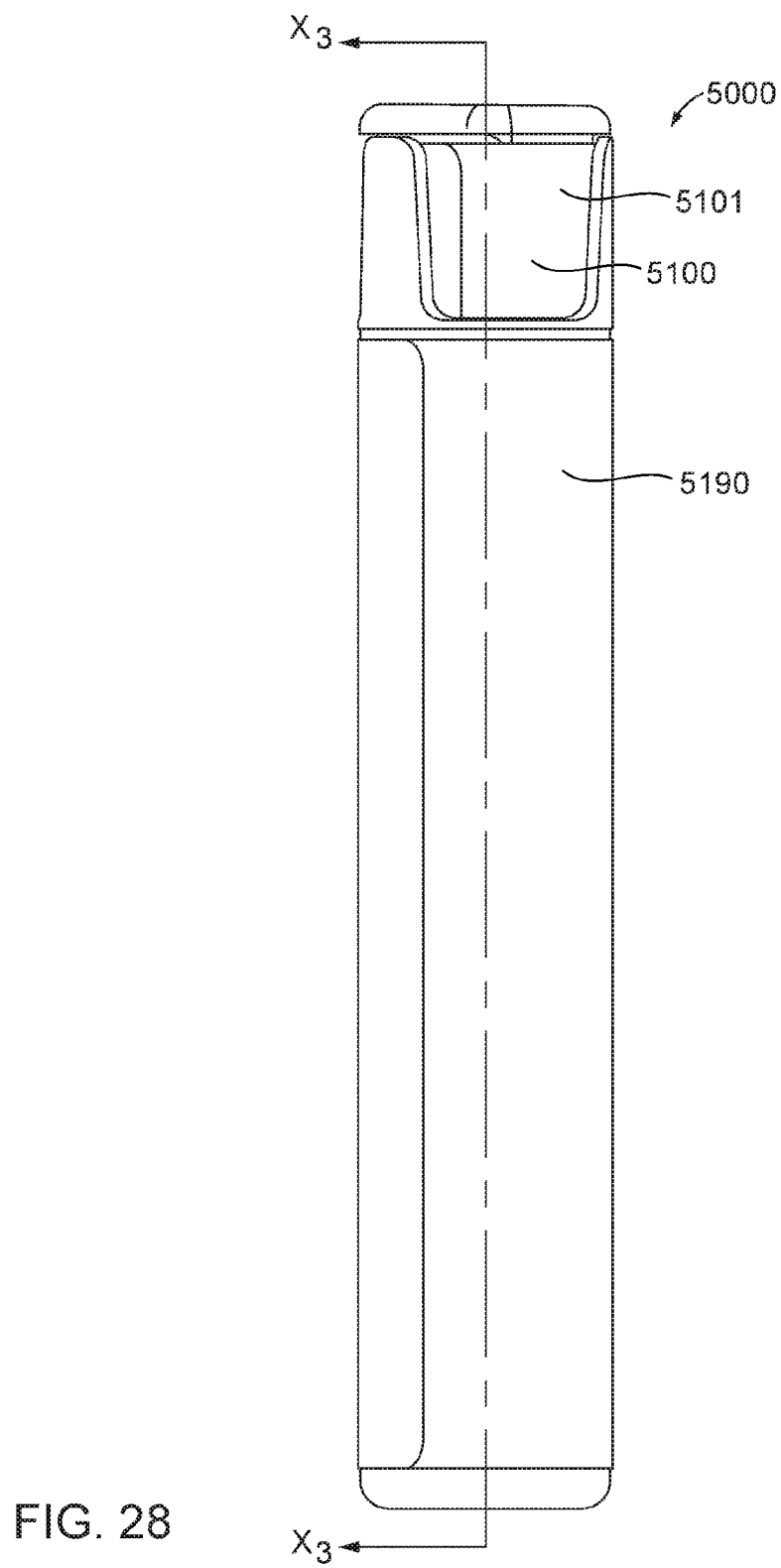
FIG. 28 is a side view of a medical injector according to an embodiment.
Figure 29:
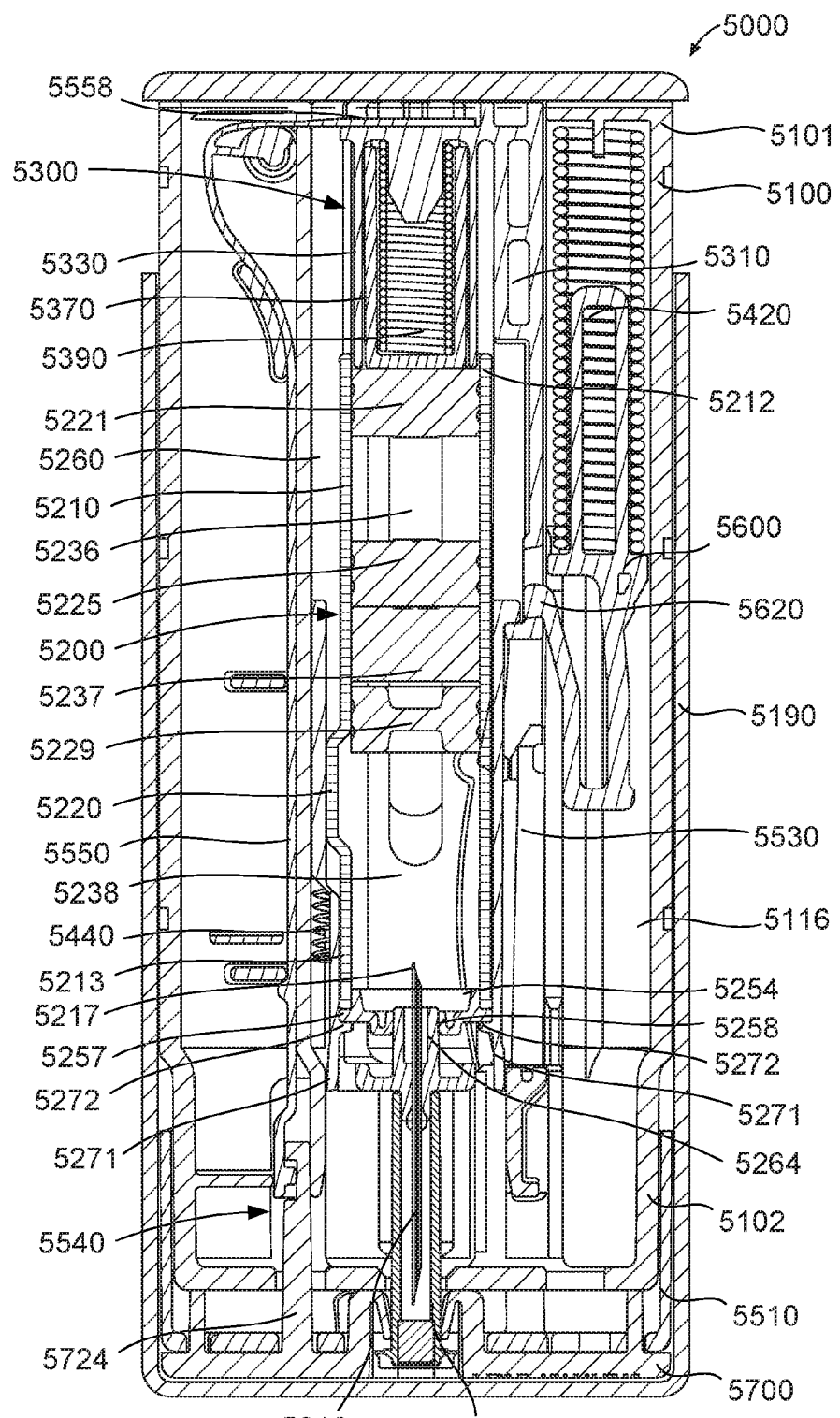
FIG. 29 is a cross-section view of the medical injector taken along the $X_3$-$X_3$ in FIG. 28, in a first configuration.

FIG. 28 is a side view of the medical injector 5000 in a first configuration. As shown in FIG. 29, the medical injector 5000 includes a housing 5100, a system actuator assembly 5500, a medicament container assembly 5200 containing a medicament 5240, a movable assembly 5300, a transfer member 5600, a cover 5190, and a safety lock 5700. In some embodiments, portion of the medical injector 5000 can be substantially similar to the medical injector 5000, described above.

The housing 5100 has a proximal end portion 5101 and a distal end portion 5102. The proximal end portion 5102 includes an end cap configured to substantially enclose the proximal end. The distal end portion 5103 can include any suitable feature to engage and/or otherwise receive at least a portion of the system actuator 5500 (e.g., a base 5510). For example, the distal end portion 5103 can include recesses, grooves, slots, notches, openings, protrusions and/or any other suitable feature. The housing 5100 is configured to substantially enclose and/or otherwise house at least a portion of the system actuator assembly 5500, the medicament container assembly 5200, the movable assembly 5300, the transfer assembly 5600, and the safety lock 5700.

The distal end portion 5100 of the housing 5100 is configured to receive an activator 5530 (also referred to herein as "release member 5530," and/or "rod 5530" included in the base 5510 of the system actuator assembly 5500. As described in more detail herein, the release member 5530 of the base 5510 is configured to engage a portion of the movable assembly 5300 (also referred to herein as "medicament delivery mechanism 5300") when the base 5510 is moved with respect to the housing 5100 to actuate the medical injector 5000. The housing 5100 includes an inner surface 5116 that can include any suitable feature configured to limit, guide, contact, separate, and/or otherwise engage a portion of the medicament container assembly 5200, the system actuator assembly 5500, the movable assembly 5300, the transfer assembly 5600, and the safety lock 5700. For example, the inner surface 5116 can include guides (not shown herein) configured to engage at least a portion of the medicament container assembly 5200 as the medicament container assembly 5200 moves from a proximal position, relative to the housing 5100, to a distal position, relative to the housing 5100. Furthermore, the housing 5100 define an opening (not shown herein) that receives a portion of a needle 5216 of the medicament container assembly 5200 such that the needle 5216 is disposed substantially outside the housing 5100 when the medicament container assembly 5200 is in the distal position, as described in further detail herein.

As shown in FIGS. 28 and 28, the cover 5190 is configured to be disposed about a portion of the housing 5100. Thus, when the portion of the housing 5100 is disposed within the cover 5190, the cover 5190 blocks an optical pathway between the medicament container 5210 and a region outside of the housing 5100. Similarly stated, when the portion of the housing 5100 is disposed within the cover 5190, the cover 5190 reduces the amount of light transmitted to the medicament within the medicament container 5210. In this manner, the life of the medicament can be extended by the prevention and/or reduction of degradation to the medicament that may be caused by ultra-violet radiation.

The medicament container assembly 5200 includes a medicament container 5210, the needle 5216, and the carrier 5260. The medicament container 5210 includes a proximal end portion 5212, a distal end portion 5213, and a bypass 5220. The medicament container 5210 can be substantially similar to the medicament container 53210 described above. Therefore, the medicament container 5210 is not described in detail herein.

The distal end portion 5213 of the medicament container 5210 is configured to engage at least a portion of the carrier 5260 and the needle 5216, as described below. The distal end portion 5213 of the medicament container 5210 receives a stopper 5254. More specifically, the stopper 5254 is configured to be disposed within the medicament container 5210 to define a substantially fluid tight and/or hermetic seal. Furthermore, the stopper 5254 includes a flange 5257 that engages a distal surface of the medicament container 5210. The flange 5257 is further configured to define a friction fit with a portion of the carrier 53260 such that the medicament container 5210 is selectively retained relative to the carrier 53260, as further described herein. The stopper 5254 further includes a set of inner walls 5258 (e.g., the stopper 3254 is substantially annular) configured to receive a proximal end portion 5217 of the needle 5216 and a portion of the carrier 5260. In this manner, the proximal end portion 5217 of the needle 5216 and a portion of the needle hub 5264 are disposed within the void volume 5238.

The proximal end portion 5212 of the medicament container 5210 receives a first elastomeric member 5221, a second elastomeric member 5225, and a third elastomeric member 5229. In some embodiments, the first elastomeric member 5221, the second elastomeric member 5225, and the third elastomeric member 5229 are placed within the medicament container 5210 during the fill process, as further described herein, to define a diluent volume 5236, a dry medicament volume 5237, and the void volume 5238. The dry medicament volume 5237 is a volume disposed within medicament container 5210 defined between a distal surface 5227 of second elastomeric member 5225 and a proximal surface 5230 of third elastomeric member 5229 and the void volume 5238 is a volume disposed within the medicament container 5210 defined between a distal surface 5231 of the third elastomeric member 5229 and the distal end portion 5213 of the medicament container 5210.

While third elastomeric member 4229 is shown and described above as being disposed substantially distal to the bypass 4220, the medicament container 5200 shown in FIG. 29 is configured such that the third elastomeric member 5229 is disposed substantially proximal to the bypass 5220.

The diluent volume 5236, the dry medicament volume 5237, and the void volume 5238 are defined by the positions of the first elastomeric member 5221, the second elastomeric member 5225, and the third elastomeric member 5229, relative to and/or within the medicament container 5210. In some embodiments, the diluent volume 5236 can contain a medicament diluent, such as, for example, water. In some embodiments, the dry medicament volume 5237 can contain a lyophilized medicament (e.g., any suitable medicament produced via any suitable lyophilizing process) including any of the formulations and/or compositions described herein.

As shown in FIG. 29, the proximal end portion 5212 of the medicament container 5210 is coupled to and/or receives a portion of the medicament delivery mechanism 5300 such that medicament delivery mechanism 5300 can move the first elastomeric member 5221, the second elastomeric member 5225, and/or the third elastomeric member 5229 to vent, mix and/or inject the medicament disposed therein. More specifically, the proximal end portion 5212 of the medicament container 5210 can receive a piston portion 5330 of a first movable member 5301 and a second movable member 5370 (also referred to herein as a "mixing piston 5370").

As described above, the medicament container 5210 is configured to engage and/or be coupled to the carrier 5260. The carrier 5260 includes a proximal end portion 5261, a distal end portion 5262, and a needle hub 5264. In some embodiments, the carrier 5260 can be substantially similar to the carrier 53260 described above. Therefore, details of the carrier 5260 are not described herein. The carrier 5260 can differ from the carrier 3260, however, in that the needle hub 5264 is configured to include a single upper portion (e.g., the upper portion 3267 and the base portion 3265 of the needle hub 3264 are of a substantially similar diameter). Although, the needle hub 5264 includes a single portion, the needle hub 5264 can be similar in function to the needle hub 3264; thus the needle hub 5264 is not described in further detail herein.

The carrier 5260 includes a set of tabs 5271 that include a container shoulder 5272. The set of tabs 5271 are configured to selectively engage a portion of the housing 5100 as the medicament container assembly 5200 is moved in the proximal direction during an injection event. The arrangement of the tabs 5271, the housing 5100, and the container shoulders 5272 are such that the flange 5257 of the stopper 5254 can selectively engage the container shoulder 5272 when the medicament container assembly 5200 is moved between the first container position and the second container position, as described in further detail herein.

The system actuator assembly 5500 includes the base 5510, the release member 5530, and a mixing actuator assembly 5540. The release member 5530 is configured to engage a latch portion 5310 of the medicament delivery mechanism 5300 when the medical injector 5000 is in its first (or storage) configuration (FIG. 29). In this manner, the release member 5530 maintains the latch portion 5310 in contact with a portion of the housing 5100. When the portion of the housing 5100 is in contact with the latch portion 5310, the portion of the housing 5100 applies a reaction force to the latch portion 5310 in response to the force applied by a spring 5420 configured to urge the transfer member 5600 and the medicament delivery mechanism 5300 in a distal direction. Similarly stated, when the latch portion 5310 is in contact with the housing 5100, the housing 5100 limits distal movement of the latch portion 5310, and thus, the medicament delivery mechanism 5300. In this manner, when the base 5510 is in a first position (i.e., before actuation of the medical injector 5000), the release member 5530 maintains the latch portion 5310 in contact with the housing 5100 and maintains the medical injector 5000 in the first configuration. Furthermore, when the medical injector 5000 is in the first configuration, at least a portion of the safety lock 5700 is disposed within a portion of the base 5510 such that the portion of the safety lock 5700 prevents the movement of the base 5510 in the proximal direction relative to the housing 5100.

The mixing actuator assembly 5540 includes the mixing actuator member 5550 and the safety lock 5700. As shown in FIG. 29, the safety lock 5700 includes the safety lock actuator 5724. The safety lock actuator 5724 is configured to selectively engage the mixing actuator member 5550. In this manner, when the safety lock 5700 is moved in the distal direction to be removed from the medical injector 5000, the safety lock actuator 5724 contacts the mixing actuator member 5550 such that the removal of the safety lock 5700 moves a portion of the mixing release member 5550 in the distal direction, as described in further detail herein.

The mixing actuator member 5550 includes a retention portion 5558 movably disposed within a portion of the first movable member 5301. The retention portion 5558 is configured to move within the portion of the first movable member 5301 between a first position (e.g., the locked position) and a second position (e.g., the mixing position). The mixing piston 5370 is disposed within the piston portion 5330 of the first movable member 5301 such that a portion of the mixing piston 5370 selectively engages the retention portion 5558 of the mixing actuator 5550. In this manner, when the mixing actuator 5550 is in the first position, the mixing piston 5370 is maintained in the first configuration. Furthermore, when the safety lock 5700 is moved in the distal direction (e.g., removed from the medical injector 5000), the retention portion 5558 is moved to the second position such that the mixing piston 5370 is actuated to urge a mixing event, as described in further detail herein.

The medicament delivery mechanism 5300 (all or portions of which can also be referred to as a "movable assembly") includes the first movable member 5301, the second movable member 5370 (the mixing piston 5370), and a mixing spring 5390. The arrangement of the first movable member 5301, the second movable member 5370, and the mixing spring 5390 is such that the mixing spring 5390 can be actuated to move the second movable member 5370 relative to the first movable member 5301 to urge a venting and/or mixing event.

The first movable member 5301 includes a latch portion 5310 and a piston portion 5330. The latch portion 5310 of the first movable member 5301 extends in the distal direction and is configured to selectively engage a portion of the housing 5100 and the release member 5530. The latch portion 5310 is further configured to engage a latch 5620 of the transfer member 5600. More particularly, when the medical injector 5000 is in the first configuration (i.e., prior to actuation), the latch portion 5310 of the first movable member 5301 is in contact with the latch 5620 of the transfer member 5600. In this manner, the transfer member 5600 can transfer a force produced by the spring 5420 to the latch portion 5310 of the first movable member 5300 to move the medicament delivery mechanism 5300 in the distal direction when the medical injector 5000 is actuated. Similarly stated, this arrangement allows the medicament delivery mechanism 5300 and/or the first movable member 5301 to move with and/or remain coupled to the transfer member 5600 during the insertion and/or injection operation.

The piston portion 5330 is configured to receive at least a portion of the mixing spring 5390 and the mixing piston 5370. More specifically, the medicament delivery mechanism 5300 is configured such that when the medical injector 5000 is in the first configuration (e.g., the storage configuration), the mixing spring 5390 is disposed within the piston portion 5330 and the mixing piston 5370 in a first (e.g., compressed) configuration (see e.g., FIG. 29). The arrangement of the first movable member 5301, the mixing piston 5370, and the mixing actuator member 5550 is such that when the mixing actuator member 5550 is moved to actuate a venting and/or mixing event, the mixing spring 5390 expands to move the mixing piston 5370 in the distal direction. Thus, the expansion of the mixing spring 5390 is such that the mixing spring 5390 exerts a force on the mixing piston 5370 to move the mixing piston 5370 in the distal direction, as further described herein.

The transfer member 5600 includes the latch and can receive and/or engage a portion of the spring 5420. The latch 5620 is configured to engage the latch portion 5310 of the first movable member 5301. In this manner, the transfer member 5600 transfers a force from the actuation of the spring 5420 to the first movable member 5301 and/or the medicament delivery mechanism 5300 to move the medicament delivery mechanism 5300 in the distal direction within the housing 5100. In this manner, the force produced by the spring 5420, which is offset from the medicament delivery mechanism 5300 and/or the medicament container 5210, results in both the insertion of the needle 5216 and injection of the medicament within the medicament container 5210. Although, as described below, the mixing spring 5390 produces a force to vent and/or mix a diluent and a lyophilized medicament, in other embodiments, a portion of the force produced by the spring 5420 can be used to facilitate the mixing process.

Figure 35:
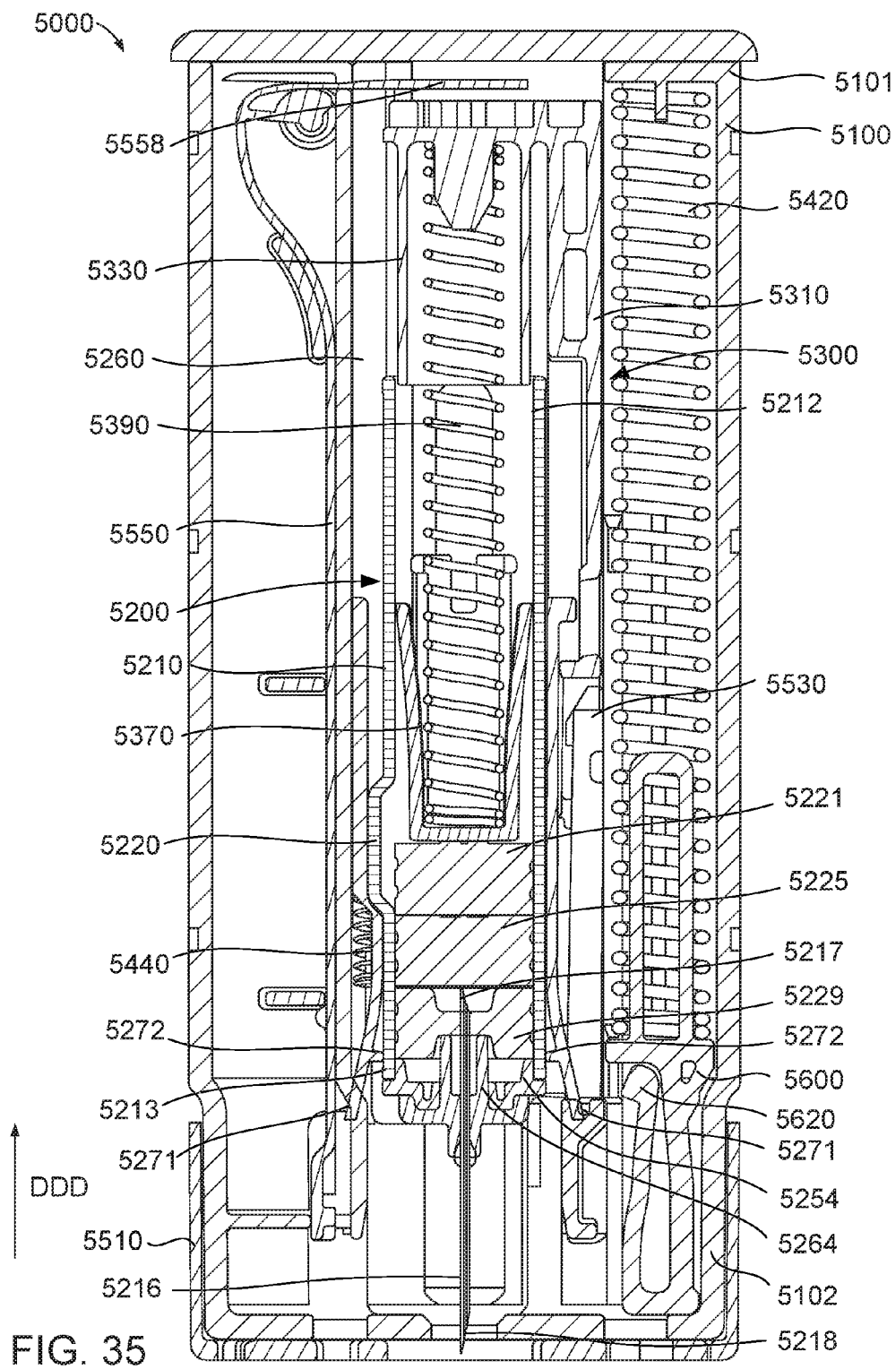

Furthermore, when the transfer member 5600 has moved a desired distance in the distal direction in response to the force produced by the actuation of the spring 5420 (e.g., upon completion of the medicament injection), the transfer member 5600 can be moved to a second configuration (see e.g., FIG. 35). In this manner, the latch 5620 can be disengaged from the latch portion 5310. Similarly stated, when the transfer member 5600 is in its second configuration, the latch 5620 is disengaged from the first movable member 5301, and the force produced by the spring 5420 is no longer transferred to the medicament delivery mechanism 5300. Said yet another way, when the transfer member 5600 is in its second configuration, the medicament delivery mechanism 5300 is isolated and/or no longer operably coupled to the spring 5420. In this manner, as described below, the retraction force exerted by the retraction spring 5440 moves the medicament delivery mechanism 5300 and/or the medicament container assembly 5200 proximally within the housing 5100 to retract the needle 5216 (FIG. 35).

As described above, the safety lock 5700 can be configured to selectively engage a portion of the housing 5100 to maintain the medical injector 5000 in the first configuration. Furthermore, the safety lock can be coupled to a needle sheath 5820 configured to be disposed about a portion of the needle 5216. When the medical injector 5000 is in the first configuration, the needle sheath 5820 can further be configured to receive the lower needle port 5268 of the carrier 5260 such that the lower needle port 5268 and the needle sheath 5820 define a substantially fluid tight and/or hermetic seal. Thus, the arrangement of the needle sheath 5820 and the lower needle port 5268 can maintain the sterility of the needle 5216 prior to actuation of the medical injector 5000 (e.g., during storage).

Figure 30:
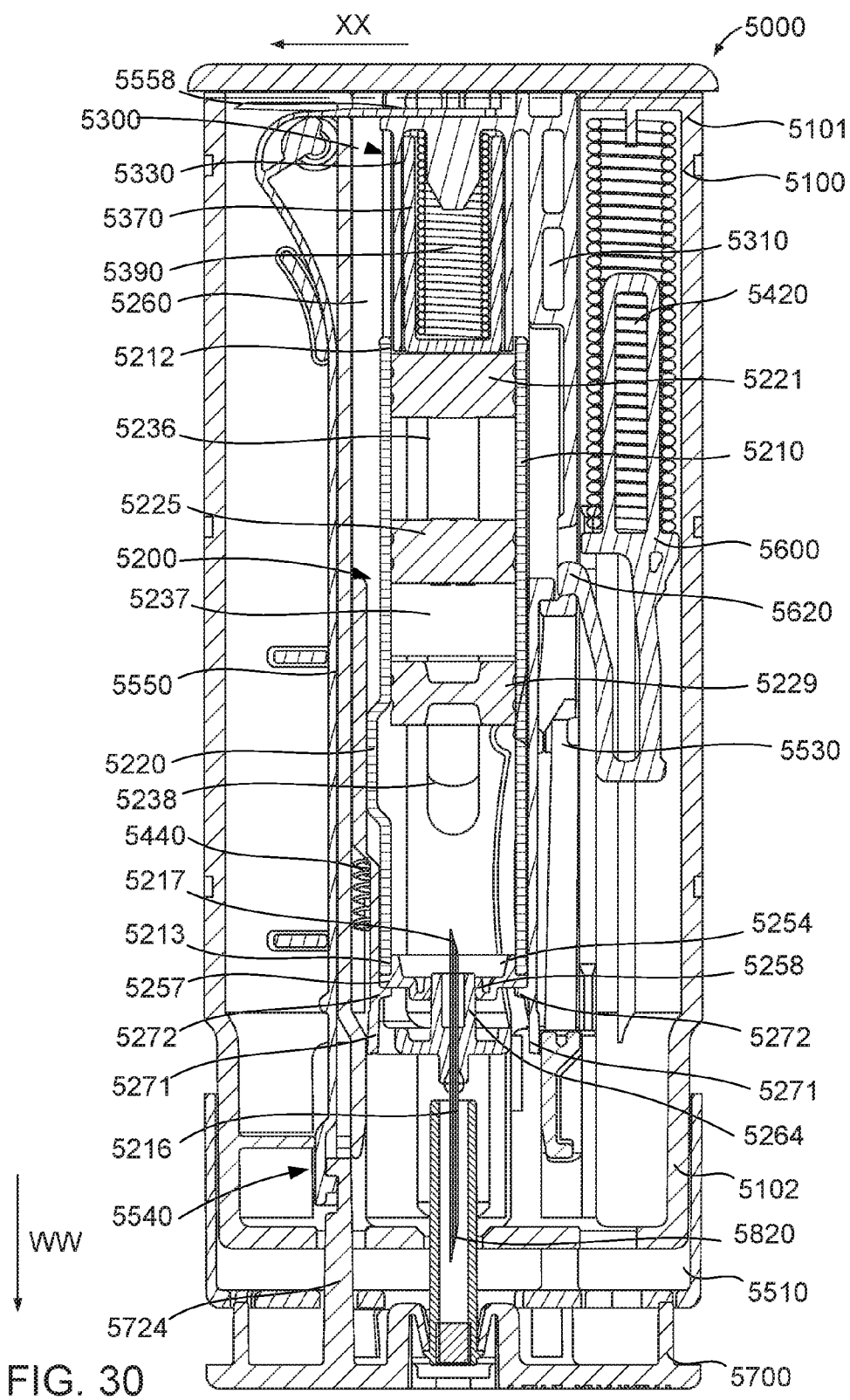
FIGS. 30 and 31 are cross-section views of the medical injector taken along the line $X_3$-$X_3$ in FIG. 28, being moved from the first configuration to a second configuration.
Figure 31:
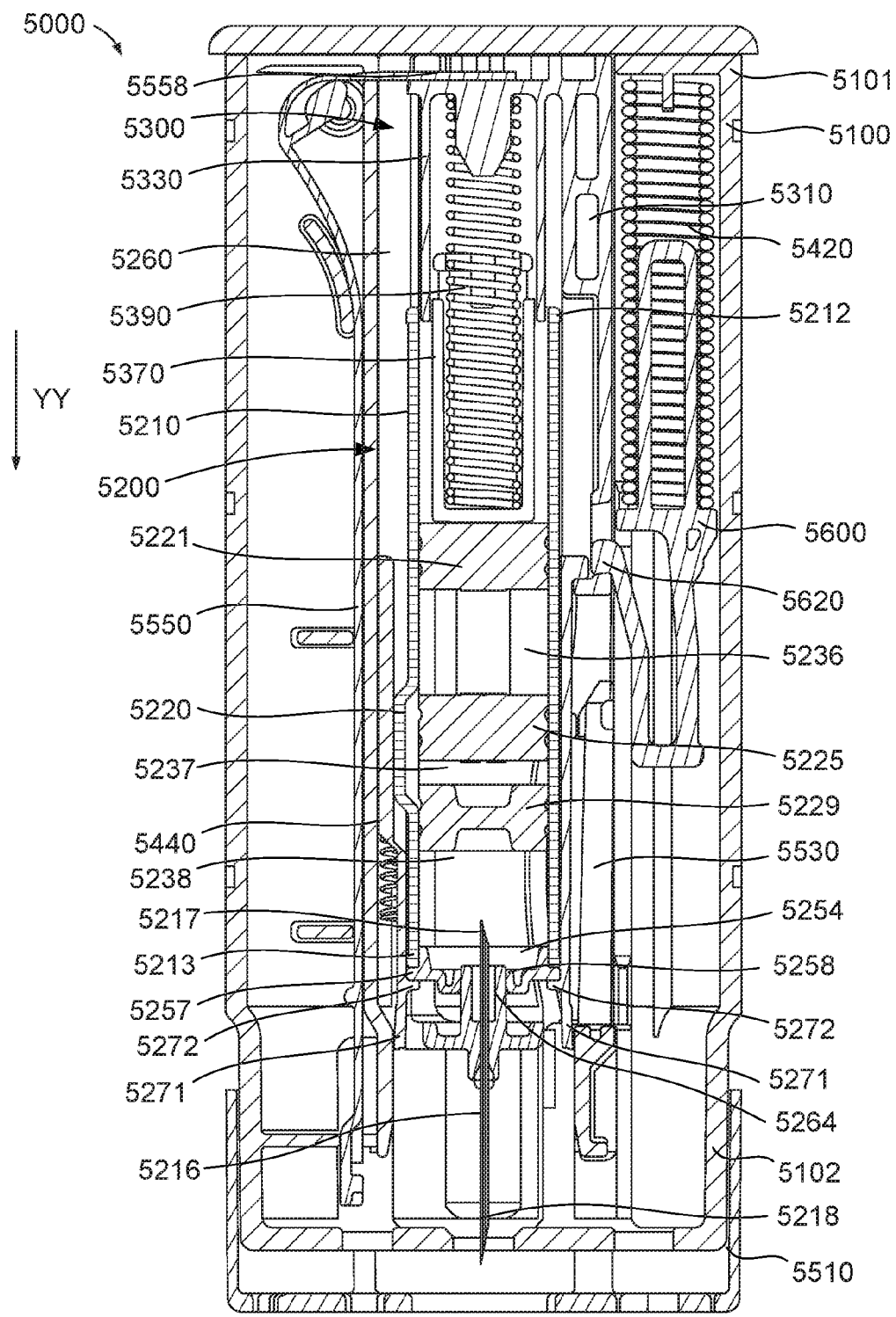

As shown in FIGS. 30 and 31, the medical injector 5000 is first enabled by moving the medicament delivery device 5000 from the first configuration to the second configuration by removing the cover 5190 and moving the safety lock 5700 in the direction shown by the arrow WW. When the safety lock 5700 is moved from the first position to the second position, the safety lock 5700 is no longer in contact with the distal end portion 5103 of the housing 5100, thereby enabling the medicament delivery mechanism 5300. Additionally, when the safety lock 5700 is removed from and/or moved relative to the housing 5100, the actuator 5724 of the safety lock 5700 also moves in the direction WW to actuate the mixing actuator member 5550. More specifically, when the actuator 5724 is moved in the direction WW, a portion of the mixing actuator member 5550 pivots relative to the housing 5100 such that the retention portion 5558 moves in the direction of the arrow XX.

As shown in FIG. 31, the lateral motion of the retention portion 5558 is such that the retention portion 5558 disengages the mixing piston 5370. In this manner, the retention portion 5558 no longer maintains the mixing spring 5390 in the first configuration (e.g., the compressed configuration). Therefore, when the retention portion 5558 moves laterally, the mixing spring 5390 expands to the second configuration and exerts a force to move the mixing piston 5370 in the distal direction, as indicated by arrow YY in FIG. 31.

With the mixing spring 5390 in the second configuration (e.g., the expanded configuration), much of the mixing piston 5370 is disposed outside the piston portion 5330 of the first movable member 5301. Similarly stated, the mixing piston 5370 is disposed in a distal position relative to the piston portion 5330 of the first movable member 5301.

Figure 32:
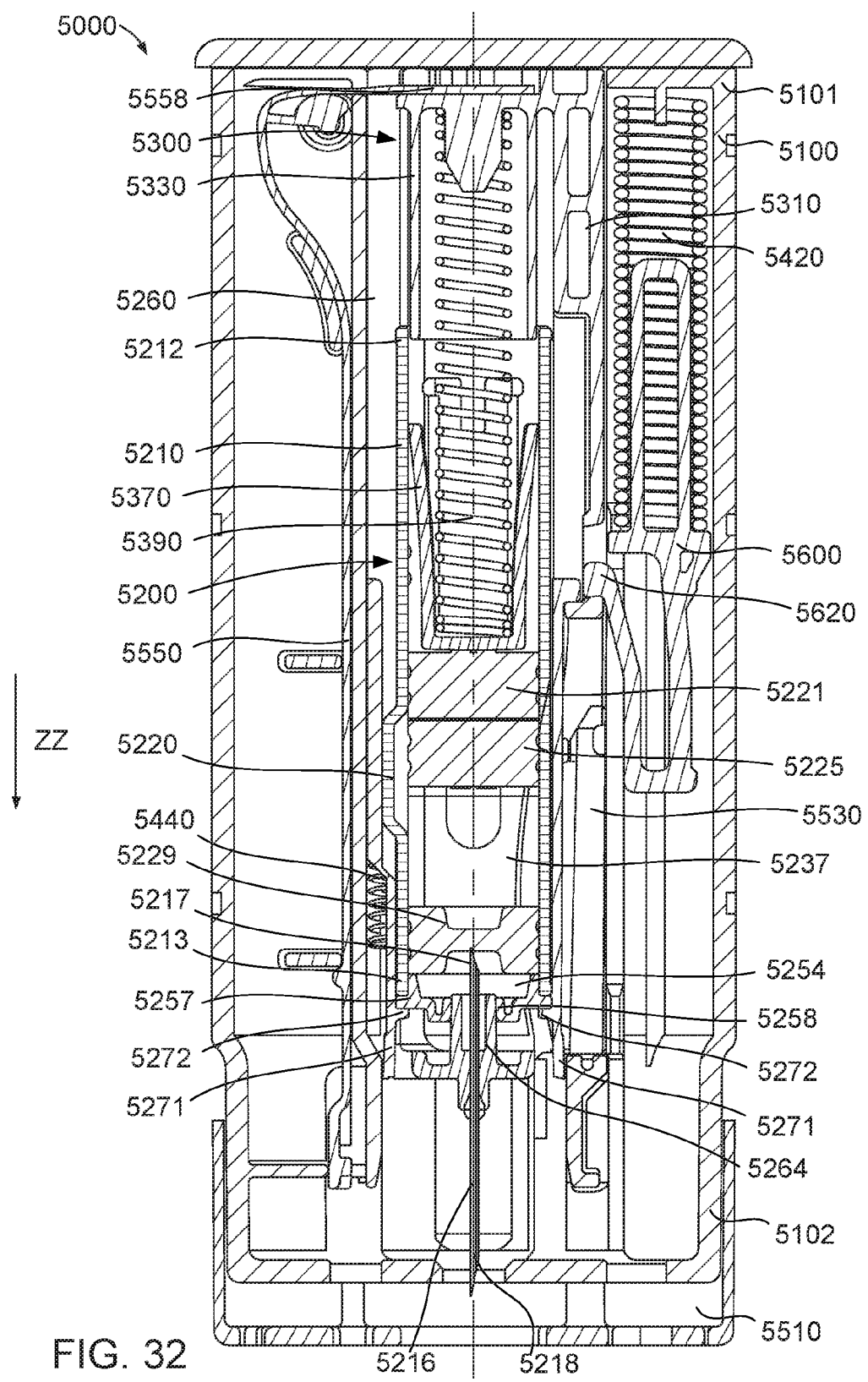

The distal movement of the mixing piston 5370 begins the venting and mixing event, as shown in FIGS. 31 and 32. More specifically, the mixing piston 5370 engages the first elastomeric member 5221 and transfers a portion of the force exerted by the mixing spring 5390 to move at least the first elastomeric member 5221 in the distal direction. The arrangement of the elastomeric members within the medicament container 5210 is such that the portion of the force exerted on the first elastomeric member 5221 moves the first elastomeric member 5221, the second elastomeric member 5225, and the third elastomeric member 5229 in the distal direction relative to the medicament container 5210. Similarly stated, the force exerted by the mixing spring 5390 moves the elastomeric members within the medicament container 5210 in the distal direction without substantially moving the medicament container 5210 and/or the carrier 5260.

The lyophilized medicament disposed within the dry volume 5237 is configured to compress such that the volume of the lyophilized medicament is reduced. More specifically, the lyophilized medicament can be configured to include approximately 93% air. In this manner, as the elastomeric members begin to move within the medicament container 5210, the lyophilized medicament is placed under pressure. Thus, when the third elastomeric member 5229 is sufficiently moved to place the dry medicament volume 5237 in fluid communication with the void volume 5238 via the bypass 5220, the air contained in the lyophilized medicament flows through the bypass and into the void volume 5238. Therefore, the air contained in the lyophilized medicament can be vented via the needle 5216.

As shown in FIG. 31, with the dry volume 5237 is compressed and the third elastomeric member 5229 is moved distal to bypass 5220 such that the dry medicament volume 5237 is no longer in fluid communication with the void volume 5238. As shown in FIG. 32, further distal movement of the mixing piston 5370 places the medical injector 5000 a third configuration (mixing configuration). Therefore, the mixing piston 5370 moves in the direction of the arrow ZZ to place the diluent volume 5236 in fluid communication with the dry medicament volume 5237 via the bypass 5220 such that the diluents within the diluent volume 5236 are transferred to the dry medicament volume 5237. More specifically, the mixing piston 5370 continues to move the first elastomeric member 5221, the second elastomeric member 5225, and the third elastomeric member 5229 in the distal direction such that the third elastomeric member 5229 is placed in contact with the stopper 5254 and the diluents volume 5236 and the dry medicament volume 5237 are placed in fluid communication. Thus, the diluent can mix with the lyophilized medicament disposed within the dry medicament volume 5237 to reconstitute the medicament for injection. In this manner, the first elastomeric member 5221 is moved into contact with the second elastomeric member 5225 such that substantially all the diluent within the diluents volume 5236 are mixed with the lyophilized medicament.

After the mixing event, the medical injector 5000 can be moved from the third configuration (FIG. 32) to a fourth configuration (FIG. 33) by moving the base 5510 from a first position to a second position. Similarly stated, the medical injector 5000 can be actuated by the system actuator assembly 5500 by moving the base 5510 proximally relative to the housing 5100. The base 5510 is moved from its first position to its second position by placing the medical injector 5000 against the body of the patient and moving the base 5510 with respect to the housing 5100 in the direction shown by the arrow AAA in FIG. 33.

When the base 5510 is moved from the first position to the second position, the system actuator assembly 5500 actuates the medicament delivery mechanism 5300, thereby placing the medical injector 5000 in its fourth configuration (i.e., the needle insertion configuration). More specifically, the proximal movement of the system actuator assembly 5500 and/or the base 5510 moves the release member 5530 in the proximal direction within the housing 5100, thereby allowing the latch portion 5310 to be disengaged from the release member 5530. Thus, the spring 5420 is allowed to expand in the direction shown by the arrow BBB in FIG. 33. In this manner, the latch 5620 of the transfer member 5600 transfers at least a portion of the force to the latch portion 5310 of the first movable member 5301 such that the portion of the force moves the medicament delivery mechanism 5300 in the distal direction, shown by the arrow BBB. Thus, the first movable member 5301 and the transfer member 5600 move together distally within the housing 5100.

When the medicament delivery mechanism 5300 is moving distally, the piston portion 5330 of the first movable member 5301 applies a portion of the force to the medicament container 5210. More specifically, the portion of the force exerted by the piston portion 5330 and/or the mixing piston 5370 moves the medicament container assembly 5200 in the distal direction. As shown in FIG. 32, when the medicament container assembly 5200 is in the first position (e.g., prior to being moved by the portion of the insertion force), the protrusions 5272 of the needle insertion tabs 5271 included in the carrier 5260 are in contact with the flange 5257 of the stopper 5254. Therefore, when the portion of the insertion force is exerted on the first elastomeric member 5221, the force is transferred through the medicament container 5210 to the protrusions 5272 to move the carrier 5260 in the distal direction.

Figure 33:
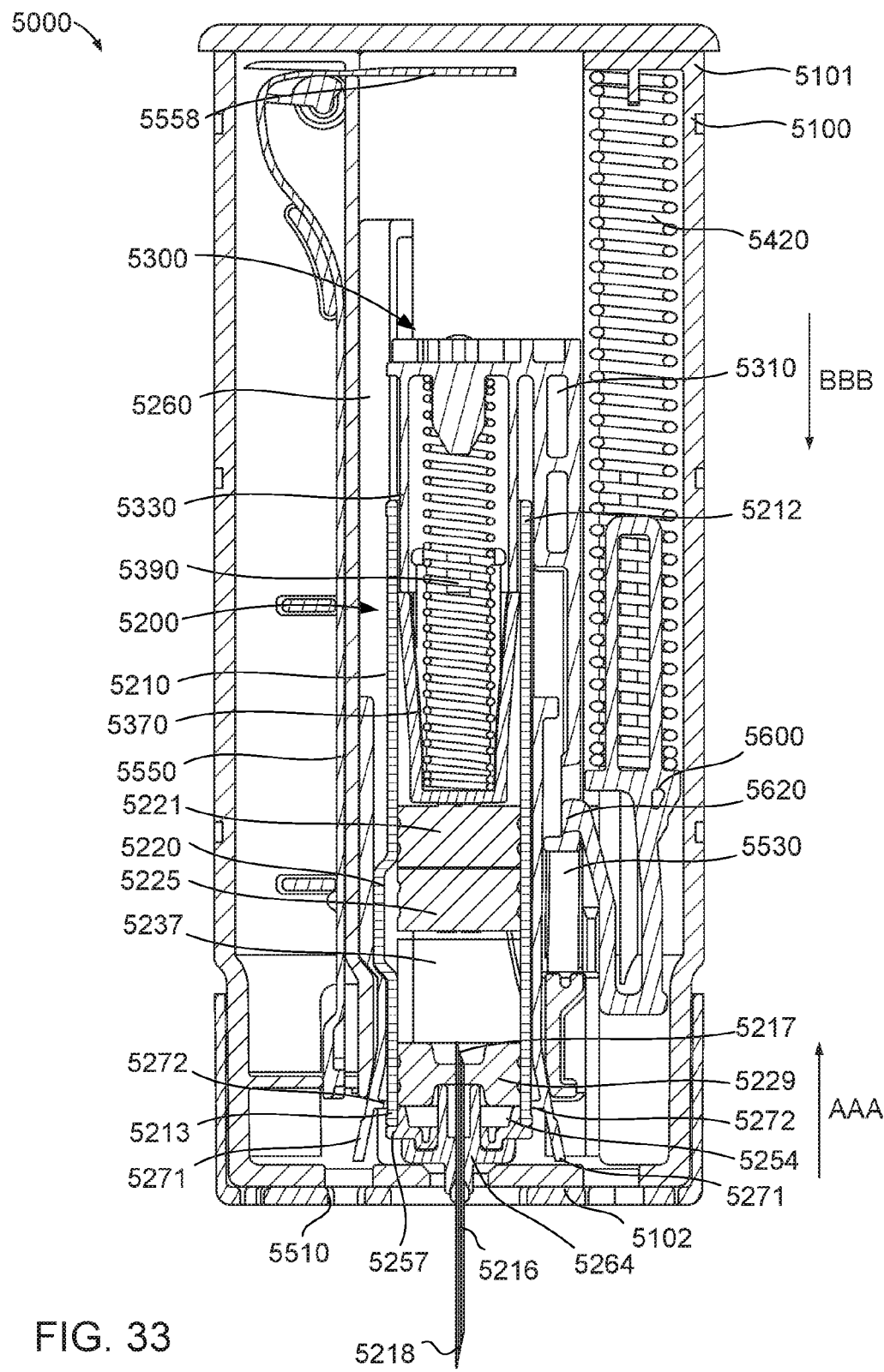
Figure 34:
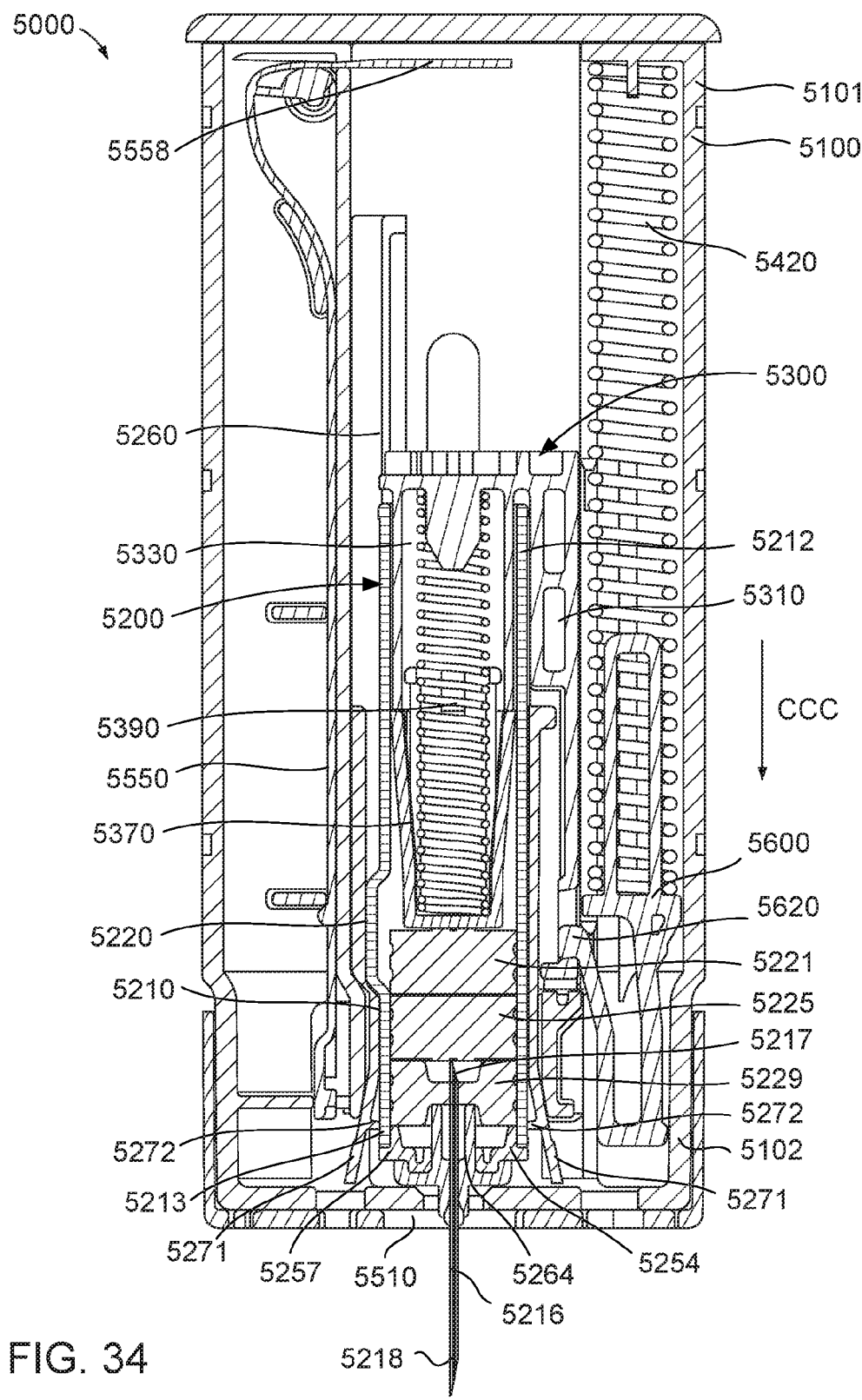

As shown in FIG. 33, the carrier 5260 moves to a second position within the housing 5100 during the needle insertion operation. With the carrier 5260 in the second position, a tabs 5271 of the carrier 5260 contact the housing 5100, thereby limiting the distal movement of the carrier 5260. Furthermore, the tabs 5271 are disengage from a portion of the housing 5100 such that the tabs 5271 expand. In the expanded configuration, the tabs 5271 extend such that the flange 5254 is no longer in contact with the protrusions 5272. Thus, the portion of the insertion force applied to the first elastomeric member 5221 moves the medicament container 5210 in the distal direction, relative to the carrier 5260. In this manner, the proximal end portion 5217 of the needle 5216 punctures through the thickness of the third elastomeric member 5229 and is placed in fluid communication with the mixing volume 5237 (e.g., the dry medicament volume). Therefore, the medical injector 5000 can be placed in a fifth configuration (i.e., the medicament delivery configuration).

The medical injector 5000 is placed in the fifth configuration when the proximal end portion 5217 of the needle 5216 is disposed within the mixing volume 5237 (e.g., the dry medicament volume 5237) and a portion of the insertion force is exerted on the first elastomeric member 5221. With the medicament container 5210 and the carrier 5260 in the second position within the housing 5100 (e.g., moved in the distal direction), the portion of the force exerted on the first elastomeric member 5221 can move the first elastomeric member 5221 and the second elastomeric member 5225 from the second position to a third position within the medicament container 5210. More specifically, the mixing piston 5370 and/or piston portion 5330 exerts the portion of the force on the first elastomeric member 5221 as indicated by arrow CCC in FIG. 34 to move the first elastomeric member 5221 and the second elastomeric member 5225 to the third position. In this manner, the medicament disposed within the dry medicament volume 5237 is transferred to the needle 5216 and injected into the body of the patient.

When the spring 5420 fully expands, the medicament delivery mechanism 5300 moves in the distal direction to fully inject the medicament within the medicament container 5210. Additionally, when the spring 5420 is fully expanded and/or when the medicament delivery mechanism 5300 has moved a desired distance within the housing 5100, the transfer member 5600 can be placed in the second configuration. In this manner, the latch 5620 can be disengaged from the latch portion 5310. Similarly stated, the spring 5420 and/or the transfer member 5600 are decoupled from the medicament delivery mechanism 5300. With the latch 5620 disengaged from the latch portion 5310, the medical injector 5000 can be moved from the fifth configuration to the sixth configuration (i.e., the retraction configuration).

With the transfer member 5600 disengaged from the medicament delivery mechanism 5300, the medicament container assembly 5200 and the medicament delivery mechanism 5300 are configured to move within the housing 5100 in the direction shown by the arrow DDD in FIG. 35 in response to a force exerted by the retraction member 5440 (e.g., the retraction spring). Similarly stated, with the medicament delivery mechanism 5300 disengaged from the transfer member 5600 and/or the spring 5420, the insertion force is no longer applied to the medicament delivery mechanism 5300. In this manner, the retraction member 5440 is configured to expand in the direction of the arrow DDD to apply a retraction force to the medicament container assembly 5200. Similarly stated, with the portion of the force insertion configured to compress the retraction spring 5440 removed, the retraction member 5440 expands, returning to its uncompressed (i.e., non-deformed) configuration.

During the retraction operation, the retraction spring 5440 exerts a retraction force on the refraction spring surface 5284 to move the carrier 5260 in the direction DDD. With the medicament container 5210 coupled to the carrier 5260 a portion of the retraction force moves the medicament container 5210 in the proximal direction. This motion, removes the needle 5216 from the target location of the patient and retracts the needle into the housing 5100, as shown in FIG. 35.

Figure 36A:
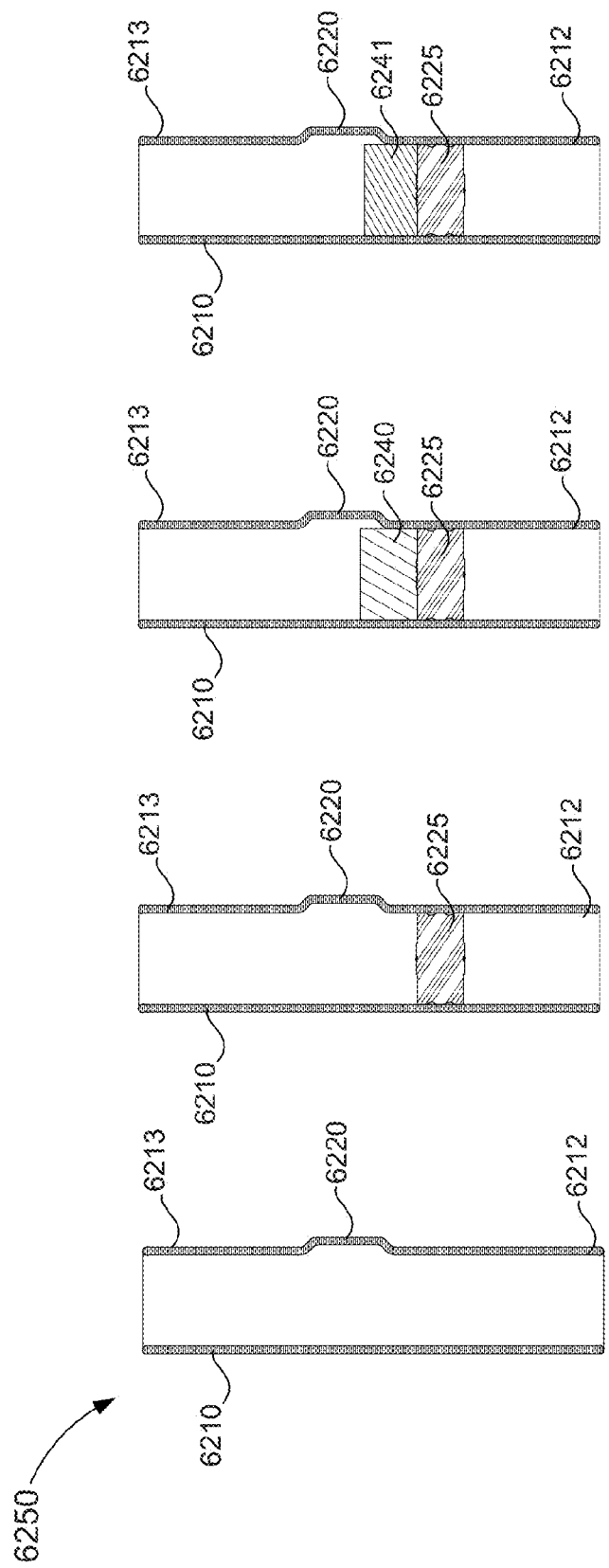
FIGS. 36A and 36B illustrate a fill system according to an embodiment.
Figure 36B:
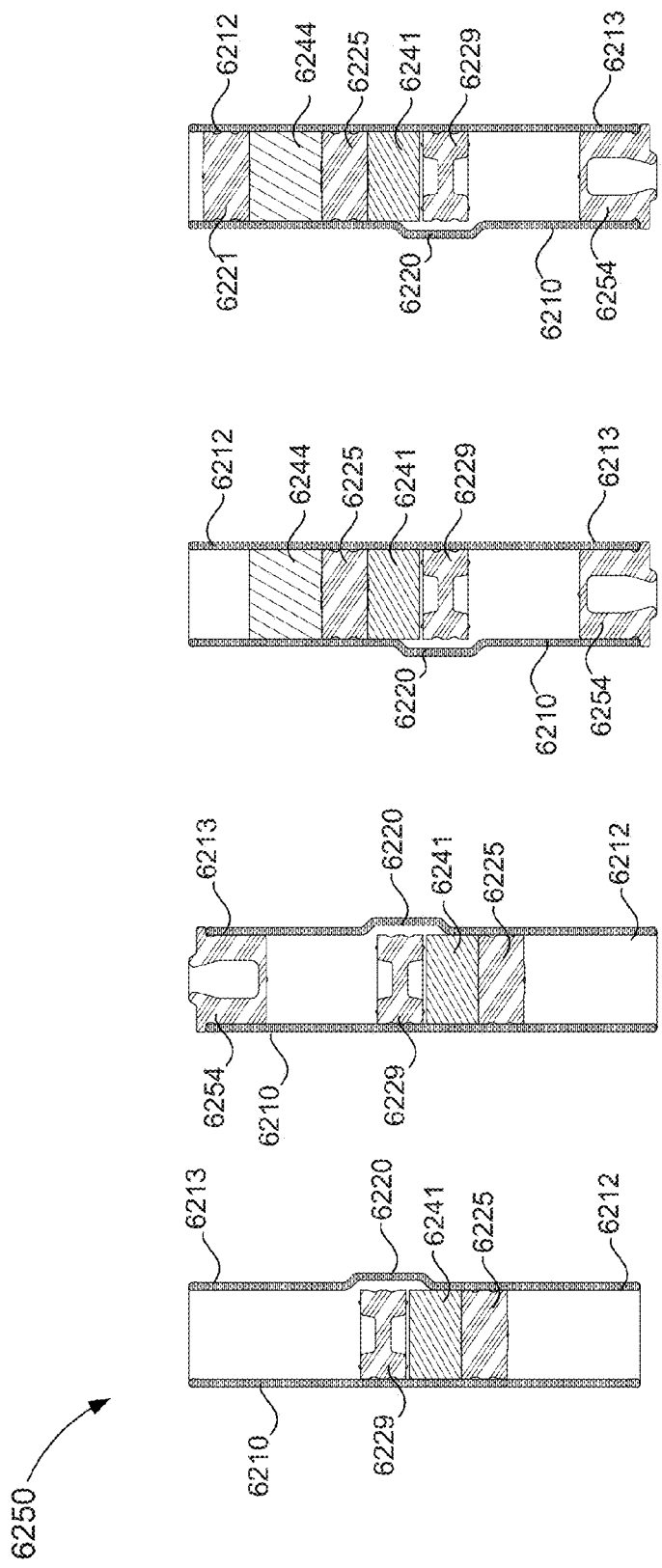

FIGS. 36A and 36B are schematic illustrations depicting a filling system or method 6250 according to an embodiment. The filling system 6250 relates to the filling of medicament constituents in a medicament container 6210. The filling system 6250 and method of use thereof includes disposing the medicament container 6210 in a tray (not shown) to secure the medicament container 6210. In some embodiments, the medicament container 6210 need not be disposed in a tray and is secure via any suitable device or system.

The medicament container 6210 can be any of the medicament containers described herein, and upon completion of the fill/finish operation includes a first elastomeric member 6221, a second elastomeric member 6225, a third elastomeric member 6229, a stopper (or fourth elastomeric member) 6254, a bypass 6220, a distal end portion 6213, and a proximal end portion 6212. As described above, in some embodiments, the proximal end portion 6212 of the medicament container 6210 can be inserted into a tray such that the medicament container 6210 is secured relative to other components of the system (not shown). With the medicament container 6210 secured a component of the filling system 6250 is configured to insert the second elastomeric member 6225 into the medicament container 6210 and moving the second elastomeric member 6225 toward the proximal end portion 6212 of the medicament container 6210. In some embodiments, the second elastomeric 6225 can be moved in the proximal direction such that a distal surface of the second elastomeric member 6225 is proximal to the bypass 6220. Similarly stated, the second elastomeric member 6225 is disposed within the medicament container 6210 such that the entire second elastomeric member 6225 is proximal of the bypass.

With the second elastomeric member 6225 disposed within the medicament container 6210 in the desired position, a portion of the fill system 6250 can deliver a solution containing the desired dosage of medicament 6240 via the distal end portion 6213. The filling system and/or method 6250 can include a lyophilizing machine (not shown), and, with the medicament 6240 disposed within the medicament container 6210, the medicament container 6210 can be inserted into the lyophilizing machine. In this manner, the medicament 6240 is lyophilized (the lyophilized medicament is designated as 6241).

As shown in FIG. 36B, a portion of the filling system 6250 can be configured to insert the third elastomeric member 6229 into the medicament container 6210 via the distal end portion 6213. In some embodiments, the filling system 6250 can include a pressure system and/or any other suitable system configured to accurately and precisely place the third elastomeric member 6229 relative to the medicament container 6210 and/or the second elastomeric member 6225. As shown, in some embodiments, the third elastomeric member 6225 is positioned such that the chamber containing the lyophilized medicament 6241 is in fluid communication with the bypass 6220. In this manner, as described above, pressure exerted on second elastomeric member 6225 can result in the conveyance of air from the lyophilized medicament 6241.

The filling system 6250 can be configured to insert the stopper 6254 into the distal end portion 6213 of the medicament container 6210 when the third elastomeric member 6229 is disposed at the desired location within the medicament container 6210. In some embodiments, the stopper 6254 can include a flange configured to engage a distal surface of the medicament container 6210, thereby maintaining the stopper 6254 in the desired position relative to the medicament container 6210. In some embodiments, the stopper 6254 is substantially similar to the stopper 3254 described above with respect to FIGS. 9-19.

With the stopper 6254 in place, the filling system 6250 can be configured to flip the medicament container 6210. With the medicament container 6210 flipped, a portion of the filling system 6250 can be configured to deliver a desired quantity and/or volume of diluent 6244 via the proximal end portion 6212. With the diluent 6244 disposed within the medicament container 6210, a portion of the filling system 6250 can insert the first elastomeric member 6221 into the medicament container 6210 via the proximal end portion 6212. Although not shown in FIGS. 36A and 36B, the filling system 6250 can include any suitable device, component, assembly, subassembly, system, subsystem, etc. configured to deliver constituents to and/or perform processes on the medicament container 6210.

Although the filling system 6250 is described as including an operation of lyophilizing a medicament within the medicament container 6210, in other embodiments, the lyophilized medicament 6241 can be added to the medicament container 6210.

In some embodiments, the filling process for the medicament solution 6240 can result in a portion of the medicament solution 6240 being disposed on an inner surface of the medicament container 6210. In such embodiments, it is can be desirable to substantially fluidically isolate the inner volumes of the medicament container 6210 from contact with humid air; thus, reducing the likelihood of reconstituting or otherwise contaminating the residual lyophilized medicament. Expanding further, while fluidically isolating the lyophilized medicament 6241 from humid air (and/or a liquid) is desirable, it can also be desirable to fluidically isolate the void volume, which can contain a residual amount of the medicament on the sidewall therein. Therefore, as described above with respect to the medical injector 3000 of FIGS. 9-19, it is desirable to dispose a needle substantially outside of the medicament container 6210 prior to the venting, mixing, and/or injection event to substantially limit the humidity and/or moisture than can be conveyed within a portion of the medicament container 6210 during the storage condition (e.g., the first configuration).

Figure 37:
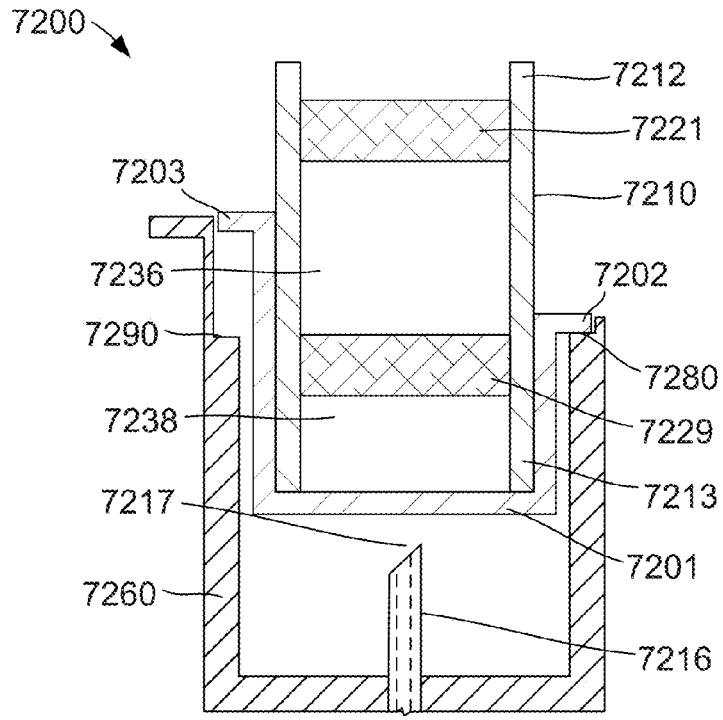
FIGS. 37-39 are schematic illustrations of a medicament container assembly device in a first configuration, a second configuration, and a third configuration, respectively, according to an embodiment.
Figure 38:
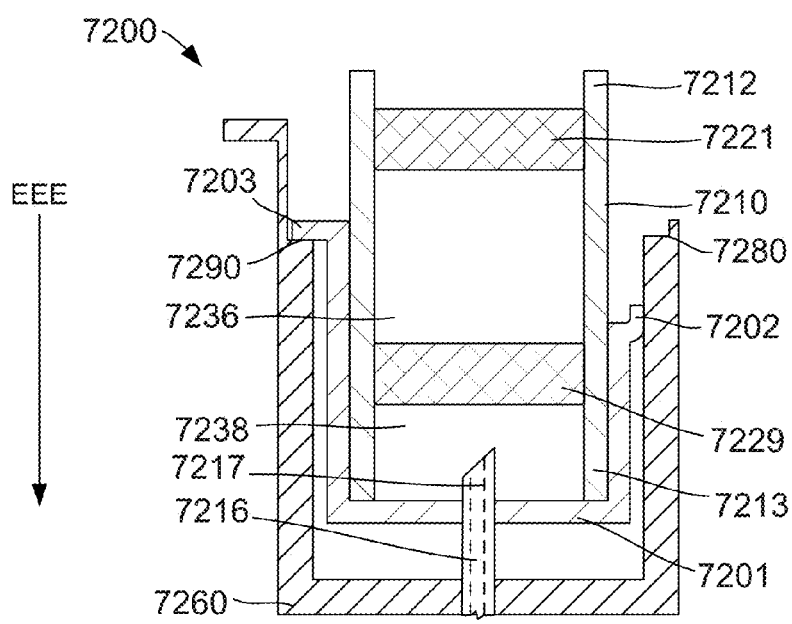
Figure 39:
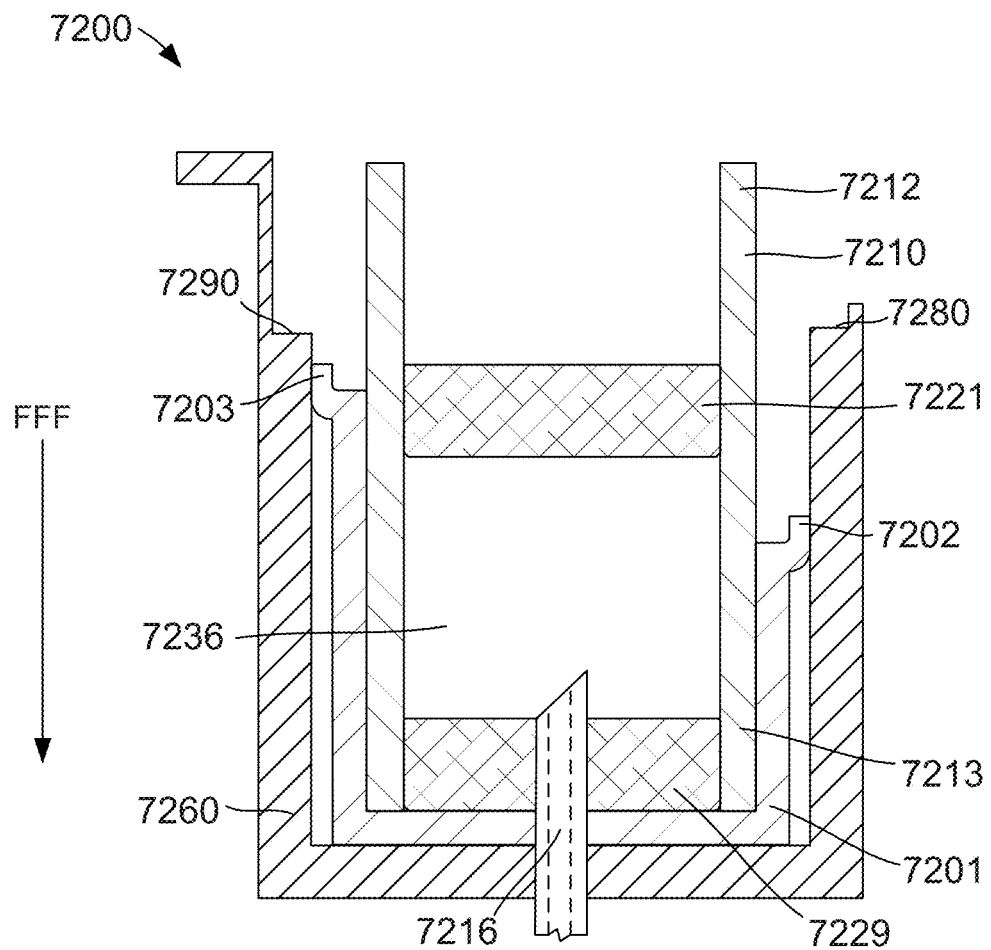

FIGS. 37-39 are schematic illustrations of a medicament container assembly 7200 in a first configuration, a second configuration, and a third configuration, respectively. The medicament container assembly 7200 can be included in any suitable delivery device such as, for example, the delivery devices described herein (e.g., the delivery devices 2000, 3000, 4000, and/or 5000). The medicament container assembly 7200 includes a medicament container 7210 that is movably coupled to a carrier 7260. The medicament container 7210 has a proximal end portion 7212 and a distal end portion 7213. The distal end portion 7213 is coupled to a stopper 7201 to form a substantially fluid tight seal. The stopper 7201 includes a first retention portion 7202 (e.g., a shoulder, protrusion, ridge, flange, and/or the like) and a second retention portion 7203 that are each configured to selectively engage a portion of the carrier 7260 to at least temporarily limit a movement of the medicament container 7210 relative to the carrier 7260, as described in further detail herein.

As shown in FIG. 37, a first elastomeric member 7221 (e.g., a plunger) is disposed within the proximal end portion 7212 of the medicament container 7210. A second elastomeric member 7229 (e.g., a plunger) is also disposed within the medicament container 7210. The first elastomeric member 7221 and the second elastomeric member 7229 can be substantially similar to the first elastomeric member 3221 and the third elastomeric member 3229, respectively, described above with reference to FIG. 11. In this manner, a surface of the first elastomeric member 7221 and a surface of an inner wall of the medicament container 7210 can form a friction fit that defines a substantially fluid tight seal. Similarly a surface of the second elastomeric member 7229 and the surface of the inner wall of the medicament container can form a friction fit that defines a substantially fluid tight seal.

The medicament container 7210 defines a medicament volume 7236 (e.g., a first volume) and a vent volume 7238 (e.g., a second volume). Expanding further, the medicament volume 7236 is defined between a distal end surface of the first elastomeric member 7221, a portion of the medicament container 7210, and a proximal end surface of the second elastomeric member 7229. In some embodiments, the medicament volume 7236 can contain, for example, a first substance, such as any suitable medicament. In some embodiments, the medicament volume 7236 can contain only a portion of a medicament such as, for example, a substantially solid portion of a medicament and a portion of air disposed between particles of the substantially solid medicament (e.g., a lyophilized medicament that can be formulated to include as much as 50% air by volume, as much as 60% air by volume, as much as 70% air by volume, as much as 80% air by volume, as much as 90% air by volume, approximately 93% air by volume). In other embodiments, the medicament volume 7236 can contain a partially aqueous medicament. In some embodiments, the medicament volume 7236 can contain any medicament specifically listed herein (e.g., listed below).

In a similar manner, the vent volume 7238 is defined between a distal end surface of the second elastomeric member 7229 a proximal surface of the stopper 7201 coupled to the distal end portion 7213 of the medicament container 7210. The vent volume 7238 can be, for example, a void volume or the like. In some embodiments, a medicament containing substantially solid particles (e.g., a lyophilized medicament) disposed within the medicament volume 7236 can be mixed with an aqueous solution such that a gas (i.e., air) within the medicament volume 7236 is vented into the vent volume 7238 (this process can also be referred to as "priming" the device for delivery). For example, in some embodiments, the medicament container 7210 can define a diluent volume (not shown in FIGS. 37-39) that can be stored separately from with the medicament within the medicament volume 7236. Upon actuation the diluent can be mixed with the medicament (e.g., a lyophilized medicament) such that the combination of the diluents and the medicament reconstitute the medicament for delivery into, for example, the body of a patient. In this manner, the mixing of the medicament and the diluent can urge a portion of the air disposed within the medicament volume 7236 to vent into the vent volume 7238. For example, in some embodiments, the medicament container 7210 can include a bypass or the like such as described above with reference to delivery device 3000 of FIGS. 9-19. In other embodiment, the second elastomeric member 7229 can be, for example, gas permeable while remaining liquid impermeable (e.g., formed from Tyvek® or a similar material).

As described above, the medicament container 7210 is movably coupled to the carrier 7260. The carrier 7260 includes a first retention portion 7280, a second retention portion 7290, and a needle 7216. As shown in FIG. 37, the carrier 7260 is configured to at least partially circumscribe (e.g., surround, enclose, contain, and/or the like) the medicament container 7210. The needle 7216 of the carrier 7260 extends in a proximal direction from a surface of the carrier 7260 (e.g., extends from the surface of the carrier 7260 toward the medicament container 7210). When the medicament container assembly 7200 is in the first configuration (e.g., FIG. 37), the stopper 7201 fluidically isolates the needle 7216 from the vent volume 7238. In some embodiments, an outer surface of the stopper 7201 can form a friction fit with an inner surface of the carrier 7260 to form a substantially fluid tight seal. In this manner, at least a proximal end portion of the needle 7216 can be disposed in a substantially sterile volume defined by a portion of the carrier 7260 and a portion of the stopper 7201. As described in further detail herein, the proximal end portion 7217 of the needle 7216 can pierce a portion of the stopper 7201, a portion of the second elastomeric member 7229, and/or a portion of the first elastomeric member 7221 during various states of operation.

The first retention portion 7280 and the second retention portion 7290 of the carrier 7260 can be, for example, shoulders that can be selectively placed in contact with the first retention portion 7202 and second retention portion 7203, respectively, of the stopper 7201. For example, as shown in FIG. 37, the first retention portion 7202 of the stopper 7201 can be in contact with the first retention portion 7280 of the carrier 7260 when the medicament container 7210 is disposed in a first position (e.g., a distal position) relative to the carrier 7260, thereby placing the medicament container assembly 7200 in the first configuration. In this manner, the first retention portion 7202 of the stopper 7201 and the first retention portion 7280 of the carrier 7260 can at least temporarily retain the medicament container 7210 in the first position relative to the carrier 7260. Moreover, as shown in FIG. 37, when the medicament container assembly 7200 is in the first configuration (e.g., when the medicament container 7210 is in the first position relative to the carrier 7260), the second retention portion 7203 of the stopper 7201 can be spaced apart a distance from the second retention portion 7290 of the carrier 7260, as described in further detail herein.

Although not shown in FIGS. 37-39, the medicament container assembly 7200 can be disposed within a medicament delivery device such as, those described above. In this manner, a user can manipulate a medicament delivery device (also referred to herein as "delivery device") to deliver the medicament disposed within the medicament container assembly 7200 to a patient. Prior to use, the medicament container assembly 7200 can be in the first configuration such that the medicament container 7210 is in the first position relative to the carrier 7260 (e.g., the proximal position relative to the carrier 7260). In this manner, the user can manipulate the delivery device to move the medicament container 7210 in the distal direction from the first position relative to the carrier 7260 to a second position relative to the carrier 7260 as indicated by the arrow EEE in FIG. 38. In some embodiments, a device can apply a force to the first elastomeric member 7221 to move the medicament container 7210 in the distal direction from the first position the second position. In other embodiments, a device can apply a force to a side wall of the medicament container 7210 to move the medicament container 7210 in the distal direction from the first position the second position.

As shown in FIG. 38, the distal movement of the medicament container 7210 from the first position to the second position relative to the carrier 7260 places the medicament container assembly 7200 in the second configuration. For example, in some embodiments, the delivery device within which the medicament container assembly 7200 is disposed can be operatively coupled to a movable assembly (not shown in FIGS. 37-39) that can engage a portion of the medicament container assembly 7200 to move the medicament container 7210 from the first position to the second position relative to the carrier 7260. More specifically, in some embodiments, the delivery device can include a movable assembly similar to the movable assembly 3300 described above with reference to FIGS. 9-19. In such embodiments, the movable assembly can be actuated by an energy storage member (e.g., a spring, a compressed gas, and/or the like) such that a portion of the movable assembly moves the medicament container 7210 in the direction of the arrow EEE. As shown in FIG. 38, the first retention portion 7202 of the stopper 7201 can deform, bend, move, or otherwise reconfigure when the medicament container 7210 is moved to the second position relative to the carrier 7260. For example, in some embodiments, the movable assembly can exert a force on the medicament container 7210 sufficient to deform the first retention portion 7202 of the stopper 7201. In other embodiments, the first retention portion 7280 of the carrier 7260 can deform in conjunction with or instead of the first retention portion 7202 of the stopper 7201.

In some embodiments, the device and/or movable assembly can actuate a mixing event substantially concurrently with moving the medicament container 7210 from the first position to the second position relative to the carrier 7260. For example, in some embodiments, the movable assembly can exert a force on a diluent volume (not shown in FIG. 37-39) to urge a diluent disposed therein to flow into the medicament volume 7236. In such embodiments, the diluent can flow within a fluid flow path toward the medicament volume 7236. For example, in some embodiments, the diluent can flow within a bypass channel (e.g., similar to the bypass 3220 described above into the medicament volume 7236. In other embodiments, the movable member can exert a force on the diluent volume such that a pressure therein is increased. In some instances, the increase in pressure can, for example, move a pressure actuated valve from a closed configuration to an open configuration. In still other embodiments, the second plunger 7229 can be selectively permeable. In this manner, the medicament disposed within the medicament volume 7236 can be reconstituted (e.g., hydrated or the like). Moreover, the mixing of the medicament (e.g., a lyophilized medicament and a diluent) can urge at least a portion of the air contained within the medicament volume 7236 (e.g., as a result of disposing and/or compressing a lyophilized medicament therein) can be urged to flow into the vent volume 7238. For example, in some embodiments, the air can flow within a flow path defined by a bypass channel or the like. In such embodiments, the first elastomeric member 7221 and/or the second elastomeric member 7229 can be moved such that the bypass channel is placed in fluid communication with the medicament volume 7236 and the vent volume 7238. In other embodiments, the second elastomeric member 7229 can be, for example, selectively permeable to allow air to flow therethrough.

As shown in FIG. 38, the second retention portion 7203 of the stopper 7201 is placed in contact with the second retention portion 7290 of the carrier 7260 when the medicament container 7210 is moved to the second position relative to the carrier 7260. In this manner, the second retention portion 7203 of the stopper 7201 and the second retention portion 7290 of the carrier 7260 at least temporarily retain the medicament container 7210 in the second position relative to the carrier 7260. Moreover, when the medicament container assembly 7200 is in the second configuration (e.g., when the medicament container 7210 is in the second position relative to the carrier 7260), the proximal end portion 7217 of the needle 7216 pierces the stopper 7201 to place the needle 7216 in fluid communication with the vent volume 7238. Thus, at least a portion air disposed within the vent volume 7238 is vented and/or conveyed through the needle 7216.

As shown in FIG. 39, the user can manipulate the delivery device (not shown) to move the medicament container 7210 from the second position to a third position relative to the carrier 7260 to place the medicament container assembly 7200 in the third configuration. For example, in some embodiments, an actuator (e.g., the movable member described above) can exert a force on a portion of the medicament container 7210 (e.g., the first elastomeric member 7221). In this manner, the force exerted on the medicament container 7210 can be sufficient to deform the second retention member 7203 of the stopper 7201 (as described above). Thus, the medicament container 7210 is no longer retained in the second position relative to the carrier 7260, and the medicament container 7210 can move in the direction of the arrow FFF in FIG. 39. In some embodiments, the force exerted on the medicament container 7210 can be operable in moving the first elastomeric member 7221 and the second elastomeric member 7229 in the FFF direction (e.g., a distal direction).

In this manner, the movement of the medicament container 7210 relative to the carrier 7260 and the movement of the elastomeric members 7221 and 7229 moves at least the second elastomeric member 7229 relative to the needle 7216. Thus, the proximal end portion 7217 of the needle 7216 can pierce the second elastomeric member 7229 to place the needle 7126 in fluid communication with the medicament volume 7236. Moreover, a surface of the stopper 7201 can be placed in contact with a surface of carrier 7260 (e.g., the medicament container 7210 "bottoms out"). Therefore, any subsequent force exerted on the medicament container 7210 can be operable in moving the first elastomeric member 7221 relative to the second elastomeric member 7229 to expel at least a portion of the medicament disposed therein through the needle 7216. Although not shown in FIGS. 37-39, in some embodiments, the medicament container assembly 7200 can be operably coupled to a retraction mechanism that, upon delivering the medicament, can retract a distal end portion of the needle 7216 from the patient (as described above with reference to the delivery device 3000 of FIGS. 9-19).

Figure 40:
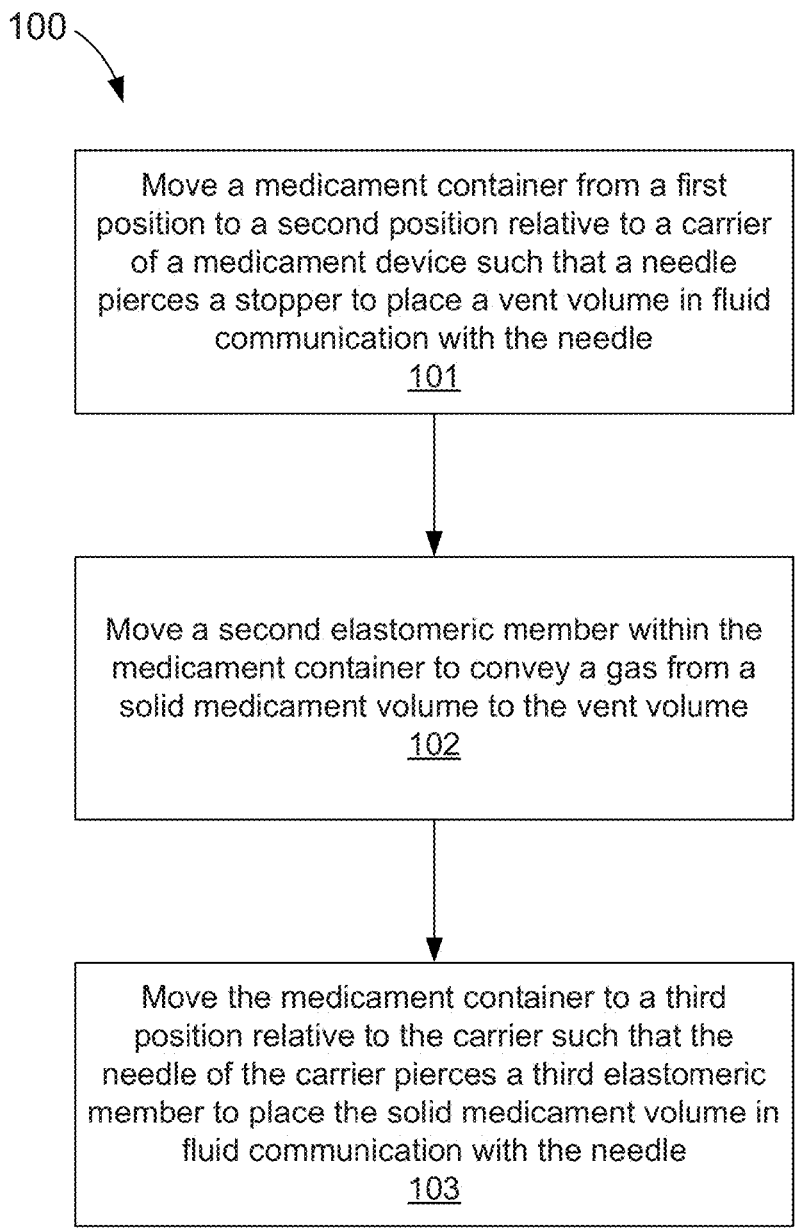
FIG. 40 is a flowchart illustrating a method of operating a medicament container assembly, according to an embodiment.

FIG. 40 is a flowchart illustrating a method 100 of operating a medicament container assembly according to an embodiment. The method 100 includes moving a medicament container from a first position to a second position relative to a carrier of a medicament device such that a needle of the carrier pierces a stopper coupled to a distal end portion of the medicament container to place a vent volume in fluid communication with the needle, at 101. The medicament device can be any of the delivery devices 1000, 2000, 3000, 4000, 5000, and/or 6000. In this manner, the medicament container can contain a first elastomeric member, a second elastomeric member, and a third elastomeric member disposed therein. In some embodiments, the vent volume can be defined between a surface of the third elastomeric member and the stopper. In a similar manner, the medicament container can define a solid medicament volume defined between the third elastomeric member and the second elastomeric member. The solid medicament volume can contain, for example, a lyophilized medicament or the like.

The second elastomeric member is moved within the medicament container to convey a gas from the solid medicament volume to the vent volume, at 102. For example, in some embodiments, a medicament delivery device can include an actuator (e.g., a movable member or the like) that can be operable in moving the medicament container from the first position to the second position. In some embodiments, the actuator can exert a force on the medicament container (e.g., via a side wall of the container, an elastomeric member within the container of the like) that is operable in moving the medicament container relative to the carrier. In some embodiments, the medicament container and/or the carrier can include a retention portion configured to limit movement of the medicament container relative to the carrier. In such embodiments, the force exerted on the medicament contain can be sufficient to deform the retention portion of the medicament container and/or the carrier such to allow the medicament container to move relative to the carrier. In some embodiments, at least a portion of the force exerted on the medicament container to move the medicament container from the first position to the second position can be operable in moving the second elastomeric member within the medicament container. In some embodiments, at least a portion of the movement of the second elastomeric member can be concurrent with the movement of the medicament container from the first position to the second position relative to the carrier.

In some embodiments, the movement of the medicament container and/or the movement of the second elastomeric member can be operable in actuating a mixing event such that a medicament having substantially solid particles is mixed with, for example, a diluent. For example, in some embodiments, the medicament container can define a diluent volume defined between the second elastomeric member and the first elastomeric member. In some embodiments, the mixing of the medicament urges the gas within the solid medicament volume to vent into the vent volume (e.g., via a bypass, a valve, a port, a selectively permeable membrane, and/or the like).

The medicament container is moved to a third position relative to the carrier such that the needle of the carrier pierces the third elastomeric member to place the solid medicament volume in fluid communication with the needle, at 103. In some embodiments, the movement of the medicament container to the third position relative to the carrier can be such that the stopper is placed in contact with the carrier (e.g., the medicament container "bottoms out" on the carrier as described above with reference to FIG. 39). In this manner, any subsequent force exerted on the medicament container can be operable in moving the first elastomeric member and/or the second elastomeric member to expel the mixed medicament from the solid medicament volume through the needle.

The embodiments, described herein can be configured such that the medicament disposed therein can be vented without having to substantially reorient the medical injector relative to the patient. For example, a distal end portion of the medical injector need not be specifically oriented (e.g., point upward) to perform a venting event.

Although the medicament container assembly 7200 is shown and described above as being used in conjunction with a venting or purge process, in other embodiments, a container assembly, such as the container assembly 7200, can be used in conjunction with a variable-dose delivery device and/or a device containing multiple doses. For example, in some embodiments, a medicament container can include two elastomeric members (e.g., plungers) and can define two volumes: a first volume and a second volume. The first volume and the second volume can, for example, correspond to the void volume 7238 and the medicament volume 7236, respectively. The first volume and the second volume can contain any suitable medicament (e.g., any liquid medicament described herein). In some embodiments, the first volume and the second volume can contain the same medicament. In other embodiments, the first volume and the second volume can contain different medicaments.

In use, the medicament container assembly can be moved into contact with a target site to insert the needle when the medicament container assembly is in the first configuration (similar to the first configuration shown in FIG. 37). In this manner, the needle insertion operation can occur when the needle is fluidically isolated from any portion of the medicament container (i.e., the first volume, which can correspond to the void volume 7238 shown above). Upon insertion to the desired depth, continued application of a force on the medicament container can cause the medicament container to move relative to the carrier into a second configuration (see e.g., FIG. 38). In this manner, the needle can be placed in fluid communication with the first volume. Accordingly, when the medicament container assembly is in the second configuration, continued movement of the first elastomeric member can expel the medicament disposed within the first volume (corresponding to the void volume 7238 shown above) via the needle.

Multi-stage delivery and/or delivery of a second dose, which is contained within the second volume (corresponding to the medicament volume 7236 shown above) can be accomplished by moving the medicament container assembly into a third configuration, similar to the configuration as shown in FIG. 39. More particularly, the continued application of a force on the medicament container and/or the second elastomeric member (e.g., either resulting from the actuation of a first energy storage member or the actuation of a second, different energy storage member) can cause the medicament container to move relative to the carrier from its second position to a third position. In the third position/third configuration, the needle can be disposed through the first elastomeric member thereby placing the second volume in fluid communication with the needle. Accordingly, when the medicament container assembly is in the third configuration, continued movement of the second elastomeric member can expel the medicament disposed within the second volume (corresponding to the medicament volume 7236 shown above) via the needle.

In this manner, a device can be configured to sequentially inject multiple doses. For example, in some embodiments, a device can include a child dose in the first volume and the incremental amount of medicament to constitute an adult dose in the second volume. The device can include a first actuator (e.g., the child dose actuator) to actuate the device to deliver the medicament from the first volume only. The device can also include a second actuator (e.g., the adult dose actuator) to sequentially deliver the medicament from within the second volume, as described above.

Although the medicament container assembly 7200 has been shown and described as including two or more elastomeric members, and being used in the context with container venting and/or multiple-dose dispensing, in other embodiments, a container assembly can include a single elastomeric member and can be used to facilitate automatic retraction of the needle and/or the medicament container. For example, in some embodiments, a container assembly can include a carrier that is similar to the carrier 7260 shown and described above, except that the needle can be releaseably coupled to the carrier (e.g., via a snap fit, threaded lock or the like). In use, the container assembly can be actuated in a similar manner as described above with reference to the delivery of a first dose from a first volume. Accordingly, after placing a medicament volume in communication with a needle by piercing the stopper, the medicament can be delivered by continued movement of the elastomeric member. When the elastomeric member "bottoms" out near the stopper, the medicament container can be moved into its third configuration, in which the needle pierces the elastomeric member (similar to the configuration shown in FIG. 39). When the needle pierces the elastomeric member, the carrier and/or stopper can engage in a manner that releases the needle from the carrier. Thus, any proximal movement of the elastomeric member can serve to retract the needle through the stopper and inside the medicament container.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Although many of the medicament delivery devices are shown and described herein as being medical injectors having a medicament container divided into three portions (see e.g., the medical injector 3000), in other embodiments, any of the components, methods and/or formulations described herein can be used in any suitable medicament delivery device, such as, for example, an auto-injector, a pen injector, an inhaler, a nasal delivery system or the like. In some embodiments, the medicament delivery device can include a medicament container having any number of plungers and/or defining any number of volumes therein.

Although the components and methods described herein are shown and described as being included in devices that include a medicament, in other embodiments, any of the components and/or methods described herein can be used in either an actual medicament delivery device or a simulated medicament delivery device. A simulated medicament delivery device can, for example, correspond to an actual medicament delivery device and can be used, for example, to train a user in the operation of the corresponding actual medicament delivery device. A simulated medicament delivery device or trainer can be similar to the simulated medicament delivery devices or trainers described in U.S. Patent Publication Number 2008/0059133, entitled "Medical Injector Simulation Device," filed Feb. 27, 2007, which is incorporated herein by reference in its entirety.

In such embodiments, the simulated medicament delivery device can simulate the actual medicament delivery device in any number of ways. For example, in some embodiments, the simulated medicament delivery device can have a shape corresponding to a shape of the actual medicament delivery device, a size corresponding to a size of the actual medicament delivery device and/or a weight corresponding to a weight of the actual medicament delivery device. Moreover, in some embodiments, the simulated medicament delivery device can include components that correspond to the components of the actual medicament delivery device. In this manner, the simulated medicament delivery device can simulate the look, feel and sounds of the actual medicament delivery device. For example, in some embodiments, the simulated medicament delivery device can include external components (e.g., a housing, a needle guard, a sterile cover, a safety lock or the like) that correspond to external components of the actual medicament delivery device. In some embodiments, the simulated medicament delivery device can include internal components (e.g., an actuation mechanism, a compressed gas source, a medicament container or the like) that correspond to internal components of the actual medicament delivery device.

In some embodiments, however, the simulated medicament delivery device can be devoid of a medicament and/or those components that cause the medicament to be delivered (e.g., a needle, a nozzle or the like). In this manner, the simulated medicament delivery device can be used to train a user in the use of the actual medicament delivery device without exposing the user to a needle and/or a medicament. Moreover, the simulated medicament delivery device can have features to identify it as a training device to prevent a user from mistakenly believing that the simulated medicament delivery device can be used to deliver a medicament. For example, in some embodiments, the simulated medicament delivery device can be of a different color than a corresponding actual medicament delivery device. Similarly, in some embodiments, the simulated medicament delivery device can include a label clearly identifying it as a training device.

Any of the stoppers described herein can be any suitable device and/or mechanism for sealing a container and/or performing the functions described herein. A stopper can include, for example an elastomeric member, a crimp seal or the like.

Although the mixing actuator member 3550 is shown and described above as being actuated by the safety lock 3700, in other embodiments, a mixing actuator can be actuated by any suitable mechanism. For example, in some embodiments, a mixing actuator member can be actuated by the needle sheath. In such embodiments, the mixing actuator member can be coupled to the needle sheath such that as the needle sheath is moved in the distal direction the needle sheath moves the mixing actuator in the distal direction. In other embodiments, the mixing actuator can be operably coupled to the needle sheath (e.g., via an intervening structure). In other embodiments, the mixing actuator member can be monolithically formed with the needle sheath and/or the safety lock.

Although the needle hub 3264 is shown and described as being configured to receive and to be coupled to the needle 3216, in other embodiments, a device can include a container hub that is devoid of a needle. For example, in some embodiments, the medical injector 3000 can be a needleless injector and the hub can define a pathway and/or otherwise be coupled to a delivery member through which the medicament is conveyed upon actuation.

Any of the medicament containers described herein can be any container suitable for storing the compositions disclosed herein. In some embodiments, the medicament container can be a pre-filled syringe, a pre-filled cartridge, a vial, an ampule or the like. In some embodiments, for example, any of the devices shown and described herein can include components and/or mechanisms to accommodate a pre-filled syringe, similar to the embodiments shown and described in U.S. Patent Application Publication No. 2013/0023825, entitled "Medicament Delivery Devices for Administration of Medicament within a Prefilled Syringe," filed on Jan. 25, 2012, which is incorporated herein by reference in its entirety. In other embodiments, the medicament container 1400 can be a container having a flexible wall, such as, for example, a bladder.

Any of the devices and/or medicament containers shown and described herein can be constructed from any suitable material. Such materials include glass, plastic (including thermoplastics such as cyclic olefin copolymers), or any other material used in the manufacture of prefilled syringes containing medications.

Any of the devices and/or medicament containers shown and described herein can include any suitable medicament or therapeutic agent. For example, although the medical injectors described above are shown and described is including a multi-chamber medicament container (e.g., medicament container 3210) that includes a substantially dry medicament (e.g., contained within the dry medicament volume 3237) and a diluent (e.g., contained within the diluent volume 3237), in other embodiments, any of the medicament delivery devices disclosed herein can include a multi-chamber container that is filled with any suitable substances. For example, in some embodiments, any of the medicament delivery devices disclosed herein can include a medicament container (e.g., a cartridge) that separately stores and mixes, upon actuation, two liquid substances. For example in some embodiments, any of the devices shown and described herein can include a medicament container filled with (in separate chambers) epinephrine and at least one antihistamine (e.g., epinephrine and diphenhydramine, epinephrine and hydroxyzine, epinephrine and cetirizine); an antipsychotic medicament and a benzodiazepine (e.g. haloperidol and diazepam, haloperidol and midazolam, haloperidol and lorazepam); insulin and a GLP-1 analog or incretin mimetic (e.g. insulin and exenatide, insulin and lixisenatide); an NSAID and an opioid (e.g., ketorolac and buprenorphine). Other suitable compositions that can be included in any of the medicament containers and/or devices described herein include pralidoxime chloride and atropine; obidoxime chloride and atropine; epinephrine and atropine; methotrexate and etanercept; methotrexate and adalimumab; and methotrexate and certolizumab. Other suitable compositions that can be included in any of the medicament containers and/or devices described herein include antipsychotic and antiparkinson anticholinergics (ex. risperidone and benztropine).

Glucagon Formulation

In some embodiments, a composition can include glucagon and/or any pharmaceutically acceptable constituents for use in the medicament delivery devices disclosed herein. In some embodiments, the glucagon formulation can be prepared and/or filled according to any of the methods described herein (e.g., the method associated with the filling system 6250). A composition according to an embodiment can be formulated such that the target concentration of glucagon in the solution, either before lyophilization and/or after being reconstituted upon actuation of the device, is approximately 1 mg/mL. In other embodiments, the target concentration of glucagon in the solution, either before lyophilization and/or after being reconstituted, can be approximately 2 mg/mL, approximately 1.5 mg/mL, approximately 0.5 mg/mL (e.g., a pediatric dose) or approximately 0.25 mg/mL. In other embodiments a composition can be formulated such that the target concentration of glucagon in the solution, either before lyophilization and/or after being reconstituted upon actuation of the device, is between approximately 0.25 mg/mL and 2 mg/mL, between approximately 0.5 mg/mL and 1 mg/mL, or between approximately 0.8 mg/mL and 1.2 mg/mL.

In certain embodiments, the concentration (either before lyophilization or upon reconstitution) of glucagon in a glucagon formulation is about 1 mg/mL and the total solute concentration is within a range of about 25 mg/mL to approximately 100 mg/mL (e.g., about 50 mg/mL). For example, in some embodiments, a composition can include glucagon and any suitable bulking agents to increase the total solute concentration in the glucagon formulation. In this manner, the glucagon formulation can be more effectively lyophilized and/or reconstituted. For example, in some embodiments, as described below, certain bulking agents can be used to improve the stability, solubility and/or efficacy of the composition when reconstituted in any of the devices shown and described herein. In some embodiments, certain bulking agents can be used to produce a visual indicia when the composition is reconstituted (e.g., such agents can allow the reconstituted medicament to be more easily detected by the user).

In some embodiments, a composition can include a peptide, such as, for example, glucagon and a carbohydrate. In this manner, the stability of the peptide (e.g., glucagon) can be increased during lyophilization and subsequent storage. In particular, the stability of peptides, such as glucagon, may be increased in an amorphous (i.e. non-crystalline) environment. It is believed that carbohydrates undergoing dehydration create a solid-state environment that is amorphous and exhibits high viscosity when maintained below the glass transition temperature. In addition, carbohydrates contain multiple hydroxyl groups that may form hydrogen bonds with polar groups on a protein or peptide surface in an amorphous solid-state environment. Without being bound by any particular mechanism, when water is removed during lyophilization, such carbohydrates may maintain the hydrogen bonds and preserve the native-like solid state of the polypeptide structure. In certain embodiments, therefore, the glucagon formulations include other excipients, such as, but not limited to carbohydrates. Suitable carbohydrates include, but are not limited to, lactose, trehalose, mannitol, and combinations thereof.

Additionally, the solubility of glucagon increases below a pH of 4. In certain embodiments, the glucagon formulations, prior to lyophilization and/or after reconstitution, have a pH of less than about pH 5.0, including less than about pH 4.5, less than about pH 4.0, less than about pH 3.5, less than about pH 3.0, less than about pH 2.5, less than about pH 2.0. In other embodiments of the invention, the glucagon formulations, prior to lyophilization and/or after reconstitution, have a pH range of about pH 1.5 to about pH 5.0, inclusive of all ranges and subranges therebetween, e.g., about pH 2.0 to about pH 4.5, about pH 2.0 to about pH 4.0, about pH 2.0 to about pH 3.5, about pH 2.0 to about pH 3.0, about pH 2.0 to about pH 2.5, about pH 2.5 to about pH 4.5, about pH 2.5 to about pH 4.0, about pH 2.5 to about pH 3.5, about pH 2.5 to about pH 3.0, about pH 3.0 to about pH 4.5, about pH 3.0 to about pH 4.0, about pH 3.0 to about pH 3.5, about pH 3.5 to about pH 4.5, and about pH 3.5 to about pH 4.0. In certain embodiments, the pH of the glucagon formulation is adjusted prior to lyophilization by the addition of a suitable acid, such as hydrochloric acid or citric acid.

The lyophilized formulations of the present invention may be reconstituted by any suitable diluent or combination of diluents, including, but not limited to, water, sterile water, glycerin, or hydrochloric acid.

As described above, in some embodiments, a glucagon formulation can include any suitable bulking agents and/or excipients. Table 1 lists the formulations investigated for lyophilization. The formulations set for the below include a concentration of glucagon in the solution, either before lyophilization and/or after being reconstituted, of approximately 1 mg/mL.

TABLE 1

| Formulation | Excipients and Concentration | Medicament |
|---|---|---|
| 1 | Lactose - 49 mg/mL | 1 mg/mL glucagon |
| 2 | Trehalose - 40 mg/mL<br>Mannitol - 20 mg/mL | 1 mg/mL glucagon |
| 3 | Trehalose - 40 mg/mL<br>Mannitol - 20 mg/mL<br>Citric acid - 1.8 mg/mL<br>Sodium citrate - 0.35 mg/mL | 1 mg/mL glucagon |
| 4 | Glycine - 20 mg/mL | 1 mg/mL glucagon |
| 5 | Mannitol - 40 mg/mL<br>Ascorbic acid - 5 mg/mL | 1 mg/mL glucagon |

Formulation 1 included lactose, which is a known animal-derived excipient. Lactose, which is used in the commercially available glucagon formulations, is a reducing sugar that may destabilize glucagon. Accordingly, Formulations 2 through 5 are lactose-free formulations. Formulation 2 utilized trehalose and mannitol as carbohydrate bulking agents. Formulation 3 included a buffer system of citric acid and sodium citrate, in addition to the carbohydrate bulking agents. Formulation 4 was carbohydrate free, containing only glycine as the bulking agent. Formulation 5 utilized only mannitol as a bulking agent and included ascorbic acid. All formulations except Formulation 3 employed hydrochloric acid to reduce the solution pH to approximately 3 before lyophilization. In some embodiments, any of the formulations described herein can include hydrochloric acid to reduce the solution pH to within any suitable range, such as, a range between approximately 2.0 and approximately 3.5 before lyophilization.

Trehalose, however, is a non-reducing sugar, and without being bound by any particular mechanism, may potentially increase the stability of glucagon, prior to lyophilization, during lyophilization, in storage, and/or after reconstitution.

In addition to the improved properties of Formulation 3, the absence of any animal-based excipients, such as lactose, make it particularly appealing from a regulatory standpoint, as the FDA has strict guidelines regarding animal-based excipients.

All five formulations listed in Table 1 were successfully reconstituted with water and resulted in solutions suitable for use in the multi-chambered container closure system of the present invention.

In some embodiments, the medicament contained within any of the medicament containers shown herein can be a vaccine, such as, for example, an influenza A vaccine, an influenza B vaccine, an influenza A (H1N1) vaccine, a hepatitis A vaccine, a hepatitis B vaccine, a haemophilus influenza Type B (HiB) vaccine, a measles vaccine, a mumps vaccine, a rubella vaccine, a polio vaccine, a human papilloma virus (HPV) vaccine, a tetanus vaccine, a diphtheria vaccine, a pertussis vaccine, a bubonic plague vaccine, a yellow fever vaccine, a cholera vaccine, a malaria vaccine, a smallpox vaccine, a pneumococcal vaccine, a rotavirus vaccine, a varicella vaccine and/or a meningococcus vaccine. In other embodiments, the medicament contained within any of the medicament containers shown herein can be epinephrine. In other embodiments, the medicament contained within any of the medicament containers shown herein can be naloxone, including any of the naloxone formulations described in U.S. patent application Ser. No. 13/036,720, entitled "Medicament Delivery Device for Administration of Opioid Antagonists Including Formulation for Naloxone," filed on Feb. 28, 2011.

In other embodiments, the medicament contained within any of the medicament containers shown herein can include insulin, glucagon, human growth hormone (HGH), erythropoiesis-stimulating agents (ESA), DeMab, Interferon and other chronic therapies, or the like. In some embodiments, such formulations can be produced using a general lyophilization process with glucagon (of recombinant origin) using bulking agents, stabilizers, buffers, pH modifying agents or other excipients comprising of, but not limited to, one or more of the following combinations: lactose, hydrochloric acid; glucose, histidine, hydrochloric acid; trehalose, mannitol, citrate; trehalose, mannitol, hydrochloric acid; trehalose, glycine, hydrochloric acid; Mannitol, ascorbic acid; and Glycine, hydrochloric acid.

In other embodiments any of the injectors described herein can be filled with and/or used to inject medicament formulations, including lyophilized biologics and/or biopharmaceuticals, such as, for example, canakinumab, certolizumab, golimumab, and/or interleukins, for the treatment of crypyrin associated periodic syndromes, hereditary andioedema, and other auto-immune diseases. In yet other embodiments any of the injectors described herein can be filled with and/or used to inject intranasal biologics, such as glucagon or human growth hormone, formulated for use in an auto injector, for the treatment of musculoskeletal diseases, growth disorders, diabetes & treatment related disorders.

In other embodiments, any of the injectors described herein can be filled with and/or used to inject an anti-thrombotics, such as LMWH, ULMWH, Xa Inhibitors, biotinylated idraparinux, etc., for either the acute management and/or surgical prophylaxis of deep vein thrombosis and/or pulmonary embolism or for the management of other conditions which may require anticoagulation to prevent thromboembolism, such as its use in cardiovascular diseases including atrial fibrillation and ischemic stroke. In another example, in some embodiments an injector according to an embodiment can be filled with and/or used to inject formulations for the treatment of asthma and/or chronic obstructive pulmonary disease.

In other embodiments, any of the injectors described herein can be filled with and/or used to inject hyaluronidase.

In other embodiments, any of the injectors described herein can be filled with and/or used to inject depot medroxyprogesterone acetate for the treatment of infertility.

In other embodiments, any of the injectors described herein can be filled with and/or used to inject Midazolam, Loxapine, Anticoagulant, Hematopoietic, Adrenocortical steroid, Antidiabetic, Sex hormones, Somatostatin Analogs, Monoclonal Antibodies, Agents for Migraine, Antianxiety Agents, Antiemetic/Antivertigo Agents, Antipychotic Agents, General Anesthetics, NSAIDs, Opioid Agonist-Antagonist, Opioid Analgesics, Skeletal Muscle Relaxants. Aminoglycosides, Antiprotozoals, Antiretroviral Agents, Antituberculosis Agents, Bacitracin, Cephalosporin and Related Antibiotics, Colistimethate sodium, Lincosamides, Monobactams, Penicillins, Polymixin B Sulfate, Antirheumatic Agents, Antimetabolites, Immune Globulins, Immunologic Agents, Monoclonal antibodies, Antimetabolites, Hematopoietic, and/or Hemin.

In other embodiments, any of the injectors described herein can be filled with and/or used to inject environmental, food, and household allergen formulations for the treatment of allergic disease, specifically for use in immunotherapy.

In still other embodiments, the medicament contained within any of the medicament containers shown herein can be a placebo substance (i.e., a substance with no active ingredients), such as water.

The medicament containers and/or medicament delivery devices disclosed herein can contain any suitable amount of any medicament. For example, in some embodiments, a medicament delivery device as shown herein can be a single-dose device containing an amount medicament to be delivered of approximately 0.4 mg, 0.8 mg, 1 mg, 1.6 mg or 2 mg. As described above, the fill volume can be such that the ratio of the delivery volume to the fill volume is any suitable value (e.g., 0.4, 0.6 or the like).

Although various embodiments have been described as having particular features and/or combinations of components, other embodiments are possible having a combination of any features and/or components from any of embodiments where appropriate. For example, any of the devices shown and described herein can include an electronic circuit system as described in the '936 application.

In some embodiments, a method includes moving a first elastomeric member within a medicament container such that a medicament within a first chamber is compressed. The medicament can be, for example, a substantially solid medicament, such as a lyophilized medicament that that contains air therein. In other embodiments, the medicament within the first chamber can include a liquid component, and the first chamber can include air. In this manner, a portion of the air within the first chamber can be conveyed (or purged) from the first chamber. As described herein, in some embodiments, the air from the first chamber can be conveyed into a second chamber of the medicament container. In some embodiments, the method includes puncturing a second elastomeric member, the second elastomeric member defining a boundary of the second chamber, such that a portion of the air within the second chamber is conveyed via the needle to volume outside of the medicament container. In other embodiments, the air from the first chamber can be conveyed to a volume outside of the medicament container.

Although the medicament containers, fill methods and methods of air venting and/or purging have been described herein as being associated with an autoinjector, in other embodiments, any of the medicament containers, fill methods and methods of air venting and/or purging described herein can be used in any suitable medicament delivery device. For example, in some embodiments, a medicament container similar to the medicament container 3200 described above can be included in a pen injector, an inhaler, an infusion device or a transdermal delivery device.

In some embodiments, a method includes actuating an energy storage member configured to produce a force on a portion of a medicament container. The portion can be, for example, a plunger (or elastomeric member) that is movable within the medicament container. In other embodiments, the force can be exerted on a portion of the medicament container such that the portion deforms to reduce a volume within which a medicament is stored. The application of the force is such that the volume is reduced, thereby compressing and/or conveying air from the volume to a volume outside of the medicament container. In this manner, any residual air within the medicament volume can be purged without the need for the user to manually apply a purge force and/or independent from the orientation of the medicament container.

What is claimed is:

1. An apparatus, comprising:
   a medicament container configured to be movably coupled to a carrier of a medicament delivery device, the carrier including a needle;
   a first elastomeric member disposed within a proximal end portion of the medicament container;
   a second elastomeric member disposed within the medicament container, the first elastomeric member, a first portion of the medicament container and the second elastomeric member collectively defining, at least in part, a medicament volume; and
   a stopper coupled to a distal end portion of the medicament container, the second elastomeric member, a second portion of the medicament container and the stopper collectively defining, at least in part, a vent volume, the stopper having a first retention portion and a second retention portion, the first retention portion configured to engage a first portion of the carrier to limit movement of the medicament container relative to the carrier when the medicament container is in a first position relative to the carrier, the second retention portion configured to engage a second portion of the carrier to limit movement of the medicament container relative to the carrier when the medicament container is in a second position relative to the carrier, the stopper configured to fluidically isolate the needle from the vent volume when the medicament container is in the first position, the needle is disposed through a portion of the stopper to fluidically couple the vent volume to the needle when the medicament container is in the second position, the needle is disposed through a portion of the second elastomeric member to fluidically couple the medicament volume to the needle when the medicament container is in a third position relative to the carrier.

2. The apparatus of claim 1, wherein:
   the stopper defines a needle volume within which the needle is disposed when the medicament container is in the first position; and
   the first retention portion and the first portion of the carrier collectively form a substantially fluid-tight seal such that the needle volume is fluidically isolated from a volume outside of the medicament container when the medicament container is in the first position.

3. The apparatus of claim 1, wherein at least one of the first retention portion or the first portion of the carrier is configured to deform when the medicament container moves from the first position to the second position.

4. The apparatus of claim 1, wherein at least one of the second retention portion or the second portion of the carrier is configured to deform when the medicament container moves from the second position to the third position relative to the carrier.

5. The apparatus of claim 1, wherein at least one of the second elastomeric member or the medicament container defines a flow path between the medicament volume and the vent volume such that when a force is exerted on the first elastomeric member, a gas within the medicament volume flows into the vent volume via the flow path.

6. The apparatus of claim 1, wherein the medicament container defines a bypass, the second elastomeric member disposed within the medicament container such that when a force is exerted on the first elastomeric member, a gas within the medicament volume flows into the vent volume via the bypass.

7. The apparatus of claim 1, wherein the medicament volume includes a medicament selected from the group consisting of adalimumab, atropine, buprenorphine, certolizumab, cetirizine, diazepam, diphenhydramine, epinephrine, etanercept, exenatide, glucagon, haloperidol, hydroxyzine, insulin, ketorolac, lixisenatide, lorazepam, methotrexate, midazolam, obidoxime chloride, pralidoxime chloride, and combinations thereof.

8. The apparatus of claim 1, wherein:
   the first retention portion and the first portion of the carrier collectively form a substantially fluid-tight seal such that a needle volume is fluidically isolated from a volume outside of the medicament container when the medicament container is in the first position; and
   the second retention portion is within the volume outside of the medicament container.

9. The apparatus of claim 1, wherein:
   the first retention portion is formed by an inner surface of the stopper; and
   the second retention portion is formed by an outer surface of the stopper.

10. The apparatus of claim 1, wherein the first retention portion is longitudinally spaced apart from the second retention portion.

11. An apparatus, comprising:
    a medicament container configured to be movably coupled to a carrier of a medicament delivery device, the carrier including a needle;
    a first elastomeric member disposed within a proximal end portion of the medicament container;
    a second elastomeric member disposed within the medicament container, the first elastomeric member, a first portion of the medicament container and the second elastomeric member collectively defining, at least in part, a medicament volume; and
    a stopper coupled to a distal end portion of the medicament container, the second elastomeric member, a second portion of the medicament container and the stopper collectively defining, at least in part, a vent volume, a retention portion of the stopper configured to engage a portion of the carrier to limit movement of the medicament container relative to the carrier when the medicament container is in a first position relative to the carrier, the stopper defining a needle volume that is fluidically isolated from the vent volume and within which the needle is disposed when the medicament container is in the first position, the retention portion and the portion of the carrier collectively forming a substantially fluid-tight seal such that the needle volume is fluidically isolated from a volume outside of the medicament container when the medicament container is in the first position, the needle being disposed through a portion of the stopper to fluidically couple the vent volume to the needle when the medicament container is in a second position relative to the carrier, the needle being disposed through a portion of the second elastomeric member to fluidically couple the medicament volume to the needle when the medicament container is in a third position relative to the carrier.

12. The apparatus of claim 11, wherein at least one of the second elastomeric member or the medicament container defines a flow path between the medicament volume and the vent volume such that when a force is exerted on the first elastomeric member, a gas within the medicament volume flows into the vent volume via the flow path.

13. The apparatus of claim 11, wherein at least one of the retention portion of the stopper or the portion of the carrier is configured to deform when the medicament container moves from the first position to the second position.

14. The apparatus of claim 11, wherein:
the portion of the carrier is a first portion;
the retention portion of the stopper is a first retention portion; and
the stopper has a second retention portion configured to engage a second portion of the carrier to limit movement of the medicament container relative to the carrier when the medicament container is in the second position relative to the carrier.

15. The apparatus of claim 11, wherein the medicament container defines a bypass, the second elastomeric member disposed within the medicament container such that when a force is exerted on the first elastomeric member, a gas within the medicament volume flows into the vent volume via the bypass.

16. An apparatus, comprising:
a medicament container configured to be movably coupled to a carrier of a medicament delivery device, the carrier including a needle;
a first elastomeric member disposed within a proximal end portion of the medicament container;
a second elastomeric member disposed within the medicament container, the first elastomeric member, a first portion of the medicament container and the second elastomeric member collectively defining, at least in part, a medicament volume; and
a stopper coupled to a distal end portion of the medicament container, the second elastomeric member, a second portion of the medicament container and the stopper collectively defining, at least in part, a vent volume, the stopper having a first retention portion and a second retention portion, the first retention portion is formed by an inner surface of the stopper and is configured to engage a first portion of the carrier to limit movement of the medicament container relative to the carrier when the medicament container is in a first position relative to the carrier, the second retention portion is formed by an outer surface of the stopper and is configured to engage a second portion of the carrier to limit movement of the medicament container relative to the carrier when the medicament container is in a second position relative to the carrier.

* * * * *

UNITED STATES PATENT AND TRADEMARK OFFICE
CERTIFICATE OF CORRECTION

PATENT NO. : 9,522,235 B2  Page 1 of 1
APPLICATION NO. : 13/827582
DATED : December 20, 2016
INVENTOR(S) : Eric S. Edwards et al.

It is certified that error appears in the above-identified patent and that said Letters Patent is hereby corrected as shown below:

In the Specification

Column 1, Line 11: the phrase "May, 22, 2012" should be -- May 22, 2012 --

Column 3, Line 25: the phrase "along the $X_3$-$X_3$" should be -- along the line $X_3$-$X_3$ --

Column 36, Line 21: the phrase "force on the refraction spring" should be -- force on the retraction spring --

Signed and Sealed this
Eleventh Day of April, 2017

Michelle K. Lee
*Director of the United States Patent and Trademark Office*